(12) United States Patent
Baumann et al.

(10) Patent No.: US 7,923,450 B2
(45) Date of Patent: *Apr. 12, 2011

(54) MODULATORS FOR AMYLOID BETA

(75) Inventors: Karlheinz Baumann, Efringen-Kirchen (DE); Alexander Flohr, Loerrach (DE); Erwin Goetschi, Reinach BL (CH); Helmut Jacobsen, Schopfheim (DE); Synese Jolidon, Blauen (CH); Thomas Luebbers, Loerrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/348,370

(22) Filed: Jan. 5, 2009

(65) Prior Publication Data

US 2009/0181965 A1    Jul. 16, 2009

(30) Foreign Application Priority Data

Jan. 11, 2008   (EP) .................................... 08150173

(51) Int. Cl.
*A61K 31/517* (2006.01)
*A61K 31/519* (2006.01)
*A61K 31/4365* (2006.01)
*A61K 31/426* (2006.01)
*C07D 471/04* (2006.01)
*C07D 401/10* (2006.01)
*C07D 277/82* (2006.01)

(52) U.S. Cl. .............. 514/264.11; 514/266.23; 514/301; 514/367; 544/279; 546/272.7; 548/161

(58) Field of Classification Search .................. None
See application file for complete search history.

(56) References Cited

U.S. PATENT DOCUMENTS

| 2003/0176454 | A1 | 9/2003 | Yamada et al. |
| 2006/0004013 | A1 | 1/2006 | Kimura et al. |
| 2007/0117798 | A1 | 5/2007 | Kimura et al. |
| 2007/0117839 | A1 | 5/2007 | Kimura et al. |
| 2007/0219181 | A1 | 9/2007 | Kimura et al. |
| 2008/0280948 | A1 | 11/2008 | Baumann et al. |
| 2009/0163485 | A1 | 6/2009 | Knust et al. |
| 2009/0181965 | A1 | 7/2009 | Baumann et al. |
| 2009/0215759 | A1 | 8/2009 | Baumann et al. |

FOREIGN PATENT DOCUMENTS

| EP | 0233461 | 8/1987 |
| EP | 1950211 | 7/2008 |
| EP | 2019093 | 1/2009 |
| WO | WO 94/04487 | 3/1994 |
| WO | 9965884 | 12/1999 |
| WO | 0025780 | 5/2000 |
| WO | 0027842 | 5/2000 |
| WO | 0078731 | 12/2000 |
| WO | 0147897 | 7/2001 |
| WO | 0187845 | 11/2001 |
| WO | 03002561 | 1/2003 |
| WO | 03040141 | 5/2003 |
| WO | 2004046118 | 6/2004 |
| WO | 2004069185 | 8/2004 |
| WO | 2004087699 | 10/2004 |
| WO | WO 2004/110350 | 12/2004 |
| WO | 2005013996 | 2/2005 |
| WO | WO 2005/115990 | 12/2005 |
| WO | 2006058905 | 6/2006 |
| WO | 2006111549 | 10/2006 |
| WO | WO 2006/112550 | 10/2006 |
| WO | WO 2006/112551 | 10/2006 |
| WO | 2007053452 | 5/2007 |
| WO | WO 2007/058304 | 5/2007 |
| WO | WO 2007/058305 | 5/2007 |
| WO | WO 2007/102580 | 9/2007 |
| WO | WO 2007/117607 | * 10/2007 |
| WO | WO 2007/135969 | 11/2007 |
| WO | WO 2007/135970 | 11/2007 |
| WO | WO 2007/139149 | 12/2007 |
| WO | 2008006103 | 1/2008 |
| WO | WO 2008/013213 | 1/2008 |
| WO | 2008065626 | 6/2008 |
| WO | 2008107096 | 9/2008 |
| WO | 2008138753 | 11/2008 |
| WO | 2009032861 | 3/2009 |

OTHER PUBLICATIONS

Dorwald F. A. Side Reactions in Organic Synthesis, 2005, Wiley: VCH, Weinheim. Preface and Chap. 1 included.*
Kubinyi, ed. 3D QSAR in Drug Design: Ligand-Protein Interactions and Molecular Similarity, vol. 2-3, Springer, 1998, 800 pages, relevant pages attached.*
Weggen et al., Nature, 414 (2001) pp. 212-216.
Morihara et al., J. Neurochem. 83 (2002) pp. 1009-1012.
Jantzen et al., J. Neuroscience 22 (2002) pp. 226-254.
Takahashi et al., J. Biol. Chem. 278 (2003) pp. 18644-18670.
Beher et al., J. Biol. Chem. 279 (2004) pp. 43419-43426.

(Continued)

*Primary Examiner* — Rebecca L Anderson
*Assistant Examiner* — Alicia L Otton
(74) *Attorney, Agent, or Firm* — George W. Johnston; Patricia S. Rocha-Tramaloni; Kimberly J. Prior

(57) ABSTRACT

The invention relates to compounds of formula

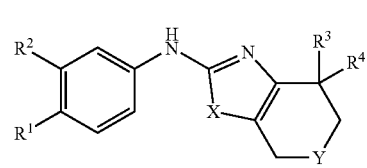

wherein $R^1$, $R^2$, $R^3$, $R^4$, X and Y are as defined herein and to pharmaceutically active acid addition salts thereof. The compounds can be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

14 Claims, No Drawings

OTHER PUBLICATIONS

Lleo et al., Nature Med. 10 (2004) pp. 1065-1066.
Kukar et al., Nature Med. 11 (2005) pp. 545-550.
Perretto et al., J. Med. Chem. 48 (2005) pp. 5705-5720.
Clarke et al., J. Biol. Chem. 281 (2006) pp. 31279-31289.
Stock et al., Bioorg. Med. Chem. Lett. vol. 16 (2006) pp. 2219-2223.
Narlawar et al., J. Med. Chem. vol. 49 (2006) pp. 7588-7591.
Mcphee et al. J. Med. Chem. Soc. vol. 66 p. 1132 (1944).
Yang et al., J. Org. Chem. vol. 67(21) p. 7429 (2002).
Siegel, Annu. Rev. Psychol., vol. 55, pp. 125-148 (2004).
Delecea et al., Proc. Natl. Acad. Sci. USA, vol. 95, pp. 322-327 (1998).
Sakurai et al, Cell, vol. 92, pp. 573-585 (1998).
Sakurai, Regulatory Peptides, vol. 126, pp. 3-10 (2005).
Peyron et al., J. Neurosci., vol. 18, pp. 9996-10015 (1998).
Nambu et al., Brain Res., vol. 18, pp. 243-260 (1999).
Chemelli et al., Cell, vol. 98, pp. 437-451 (1999).
Lin et al., Cell, vol. 98, pp. 365-376 (1999).
Nishino et al., Lancet, vol. 355, pp. 39-40 (2000).
Peyron et al., Nature Medicine, vol. 6, pp. 991-997 (2000).
Mignot et al., Sleep, vol. 11, pp. 1012-1020 (1997).
McPhee et al., J. Med. Chem. Soc., vol. 66, p. 1132 (1944).
Yang et al., J. Org, Chem., vol. 67(21), p. 7429 (2002).
Dorwald F. A., Side Reactions in Organic Synthesis 2005, Wiley, VCH Weinheim Preface & Chapter 1 included (pp. 1-16).
Kubinyi, 3D QSAR in Drug Design: Ligand Protein Interactions & Molecular Similarity, vol. 2-3, Springer, 1998, 800 pgs. relevant pages attached (pp. 243-244).
Piper et al., Eur. J. Neuroscience, vol. 12, pp. 726-730 (2000).
Sakamoto et al, Regul Pept., vol. 118, pp. 183-191 (2004).
Ida et al, Biochem. Biophys. Res. Comm., vol. 270, pp. 318-323 (2000).
Kuru et al., Neuroreport, vol. 11, pp. 977-1980 (2000).
Winsky Sommerer et al., J. Neuroscience, vol. 24, pp. 11439-11448 (2004).
Chang et al., Neurosci. Res., vol. 56, pp. 356-362 (2006).
Suzuki et al., Brain Research, vol. 1044, pp. 116-121 (2005).
Digby et al., J Endocrinol., vol. 191, pp. 129-136 (2006).
Cai et al., Expert Opin. Ther. Patents, vol. 16(5), pp. 631-646 (2006).
Dhar T G et al., Bioorg. & Med. Chem. Ltrs., vol. 12(12), pp. 3125-3128 (2002), Abstract XP002522864.
Paul et al., J. Med. Chem., vol. 36(19), pp. 2716-2725 (1099) Abstract XP002522865.
Malherbe et al., Mol. Pharmacol., vol. 64, pp. 823-832 (2003).
Bingham et al., Current Opinion in Drug Discovery & Development, vol. 9(5), pp. 551-559 (2006).
Bourgin et al. J. Neurosci., vol. 20(20), pp. 7760-7765 (2000).
Smith et al., Neurosci. Lett., vol. 341(3), pp. 256-258 (2003).
Office Action mailed Sep. 30, 2009, in copending U.S. Appl. No. 12/334,559, filed Dec. 15, 2008.
Office Action mailed May 20, 2010, in copending U.S. Appl. No. 12/334,559, filed Dec. 15, 2008.
Office Action mailed Jun. 28, 2010, in copending U.S. Appl. No. 12/114,852, filed May 5, 2008.
International Search Report issued May 15, 2009, in PCT/EP2008/067273, filed Dec. 11, 2008.
International Search Report issued Oct. 8, 2008, in PCT/EP2008/055290, filed Apr. 30, 2008.
International Search Report issued Apr. 22, 2009, in PCT/EP2009/051613, filed Feb. 12, 2009.

\* cited by examiner

MODULATORS FOR AMYLOID BETA

PRIORITY TO RELATED APPLICATIONS(S)

This application claims the benefit of European Patent Application No. 08150173.6, filed Jan. 11, 2008, which is hereby incorporated by reference in its entirety.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has loose substrate specificity and may cleave further membrane proteins unrelated to APP and Notch.

The γ-secretase activity is absolutely required for the production of Aβ peptides. This has been shown both by genetic means, i.e., ablation of the presenilin genes and by low-molecular-weight inhibitory compounds. Since according to the amyloid hypothesis for AD the production and deposition of Aβ is the ultimate cause for the disease, it is thought that selective and potent inhibitors of γ-secretase will be useful for the prevention and treatment of AD.

An alternative mode of treatment is the modulation of the γ-secretase activity which results in a selective reduction of the Aβ42 production. This will result in to an increase of shorter Aβ isoforms, such as Aβ38, Aβ37 or others, which have reduced capability for aggregation and plaque formation, and hence less neurotoxic. Compounds which show this effect on modulating γ-secretase activity include certain non-steroidal anti-inflammatory drugs (NSAIDs) and related analogues (Weggen et al. Nature, 414 (2001) 212-16).

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

SUMMARY OF THE INVENTION

The invention provides compounds of formula I

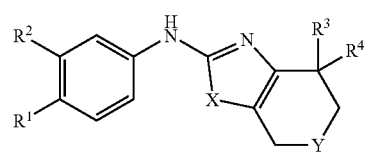

I $R^1$ is —C(O)O-lower alkyl, cyano or is hetaryl; hetaryl is a five- or six membered heteraryl group, optionally substituted by R';
R' is halogen, lower alkyl, lower alkyl substituted by halogen, lower alkoxy or lower alkoxy substituted by halogen;
$R^2$ is hydrogen, lower alkoxy, lower alkyl, halogen or cyano;
$R^3$ is —(CH$_2$)$_n$—C(O)O-lower alkyl, lower alkyl, lower alkoxy, hydroxy, —O—Si(CH$_3$)$_2$-lower alkyl, —C(O)—N(lower alkyl)$_2$, —O—S(O)$_2$-lower alkyl, C$_{3-7}$-cycloalkyl, S(O)$_2$-aryl, heterocyclyl, —C(O)-heterocyclyl, aryl or hetaryl, wherein aryl or hetaryl rings are optionally substituted by one or more R';
$R^4$ is hydrogen, lower alkyl, hydroxy or CH$_2$CN;
X is S or —N=C(R$^5$)—;
$R^5$ is hydrogen, lower alkyl or hydroxy,
Y is a bond, —O—, —CH$_2$—, —CH$_2$—CH$_2$—,

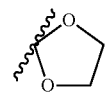

or —N(R)—;
R is hydrogen, lower alkyl, C(O)O-lower alkyl, C(O)-lower alkyl, S(O)$_2$-lower alkyl, or benzyl; and
n is 0 or 1;
or pharmaceutically active acid addition salts thereof.

The invention also provides all forms of optically pure enantiomers, racemates or diastereomeric mixtures for compounds of formula I.

The invention further provides pharmaceutical compositions containing compounds of formula I per se, and their pharmaceutically acceptable salts. The invention provides methods for the manufacture of the compounds and compositions of the invention.

Compounds of formula I are modulators for amyloid beta and thus, they can be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

The term "lower alkoxy substituted by halogen" denotes an alkoxy group as defined above wherein at least one hydrogen atom is replaced by halogen, for example $OCF_3$, $OCHF_2$, $OCH_2F$, $OCH_2CF_3$, $OCH_2CH_2CF_3$, $OCH_2CF_2CF_3$ and the like.

The term "halogen" denotes chlorine, iodine, fluorine and bromine.

The term "$C_{3-7}$-cycloalkyl" denotes a saturated cyclic alkyl ring, having from 3 to 7 carbon ring atoms, for example, cyclopropyl, cyclopentyl or cyclohexyl.

As used herein, the term "five-membered heteraryl group" denotes a heteroaryl group, containing two or three heteroatoms, selected from the group consisting of N, S and O, for example oxazol-5-yl, [1,2,4]triazol-1-yl, imidazol-1-yl, pyrazol-4-yl, thiazo-5-yl, [1,2,4]oxadiazol-5-yl or [1,3,4]-oxadiazol-2-yl. Preferred are the imidazol-1-yl, pyrazol-4-yl, thiazo-5-yl or oxazol-5-yl groups.

As used herein, the term "six-membered heteraryl group" denotes a heteroaryl group, containing one to three nitrogen atoms, for example pyridyl, pyramidyl or pyridazyl. Preferred are the pyrid-4-yl, pyrimid-6-yl or pyridaz-4-yl groups. Most preferred are the pyrid-4-yl or pyrimid-6-yl groups.

The term "aryl" denotes an aromatic mono or bicyclic carbon ring system, for example phenyl or naphthyl.

The term "heterocyclyl" denotes a monocyclic or bicyclic ring comprising from 1 to 9 carbon atoms as ring members, with the other remaining ring member atoms being selected from one or more O, N and S. Preferred heterocyclyl groups are 5 or 6 membered heterocycloalkyl groups. Examples are of such groups include piperidine, piperazine, morpholine, pyrrolidin, pyrrolidin-2-one, imidazolidin-2-one, tetrahydro-furan, thiomorpholine, thiomorpholine-1-oxide, thiomorpholinel-1,1-dioxide, 1-H-benzoimidazole, 1,3-dihydro-benzolimidazole-2-one, tetrahydro-pyrane, andor 1,3-dimethyl-1,3-dihydro-benzoimidazol-2-one as well as those groups specifically illustrated by the examples herein below.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

Preferred is a compound of formula

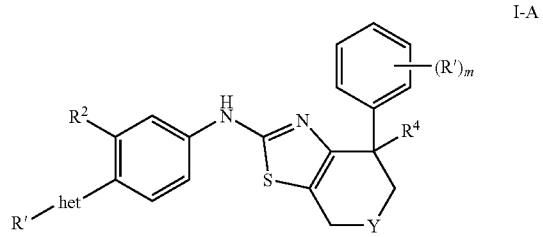

I-A wherein
het is a five- or six membered heteraryl group;
R' is hydrogen, halogen, lower alkyl, lower alkyl substituted by halogen, lower alkoxy or lower alkoxy substituted by halogen;
$R^2$ is hydrogen, lower alkoxy, hydroxy, lower alkyl, halogen or cyano;
$R^4$ is hydrogen, lower alkyl, hydroxy or $CH_2CN$;
Y is a bond, —O—, —$CH_2$—, —$CH_2$—$CH_2$—,

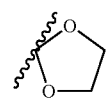

or —N(R)—;
R is hydrogen, lower alkyl, C(O)O-lower alkyl, C(O)-lower alkyl, $S(O)_2$-lower alkyl, or benzyl; and
m is 0, 1, or 2;
or a pharmaceutically active acid addition salt thereof Preferred compounds from formula I-A are those, wherein Y is —$CH_2$—, for example the following compounds
(3-methoxy-4-oxazol-5-yl-phenyl)-(4-phenyl-4,5,6,7-tetrahydro-benzothiazol-2-yl)-amine;
[3-fluoro-4-(4-methyl-imidazol-1-yl)-phenyl]-(4-phenyl-4,5,6,7-tetrahydro-benzothiazol-2-yl)-amine;
[3-methoxy-4-(4-methyl-imidazol-1-yl)-phenyl]-(4-phenyl-4,5,6,7-tetrahydro-benzothiazol-2-yl)-amine;
[3-methoxy-4-(4-methyl-imidazol-1-yl)-phenyl]-[4-(2-methoxy-phenyl)-4,5,6,7-tetrahydro-benzothiazol-2-yl]-amine;
[3-methoxy-4-(4-methyl-imidazol-1-yl)-phenyl]-[4-(4-methyl-3-trifluoromethyl-phenyl)-4,5,6,7-tetrahydro-benzothiazol-2-yl]-amine;
[3-methoxy-4-(4-methyl-imidazol-1-yl)-phenyl]-[4-(4-trifluoromethoxy-phenyl)-4,5,6,7-tetrahydro-benzothiazol-2-yl]-amine;
[4-(2,5-difluoro-phenyl)-4,5,6,7-tetrahydro-benzothiazol-2-yl]-[3-methoxy-4-(4-methyl-imidazol-1-yl)-phenyl]-amine;
[4-(2,5-dimethyl-phenyl)-4,5,6,7-tetrahydro-benzothiazol-2-yl]-[3-methoxy-4-(4-methyl-imidazol-1-yl)-phenyl]-amine;

[4-(2-chloro-phenyl)-4,5,6,7-tetrahydro-benzothiazol-2-yl]-[3-methoxy-4-(4-methyl-imidazol-1-yl)-phenyl]-amine;
[4-(3-fluoro-4-methyl-phenyl)-4,5,6,7-tetrahydro-benzothiazol-2-yl]-[3-methoxy-4-(4-methyl-imidazol-1-yl)-phenyl]-amine;
[4-(4-chloro-3-trifluoromethyl-phenyl)-4,5,6,7-tetrahydro-benzothiazol-2-yl]-[3-methoxy-4-(4-methyl-imidazol-1-yl)-phenyl]-amine;
[4-(4-methyl-imidazol-1-yl)-phenyl]-(4-phenyl-4,5,6,7-tetrahydro-benzothiazol-2-yl)-amine;
{4-(4-chloro-phenyl)-2-[3-methoxy-4-(4-methyl-imidazol-1-yl)-phenylamino]-4,5,6,7-tetrahydro-benzothiazol-4-yl}-acetonitrile;
2-(4-methyl-imidazol-1-yl)-5-(4-phenyl-4,5,6,7-tetrahydro-benzothiazol-2-ylamino)-benzonitrile;
[4-(2,4-dichloro-phenyl)-4,5,6,7-tetrahydro-benzothiazol-2-yl]-[3-methoxy-4-(4-methyl-imidazol-1-yl)-phenyl]-amine;
[4-(2,5-dichloro-phenyl)-4,5,6,7-tetrahydro-benzothiazol-2-yl]-[3-methoxy-4-(4-methyl-imidazol-1-yl)-phenyl]-amine;
[4-(3,5-dichloro-phenyl)-4,5,6,7-tetrahydro-benzothiazol-2-yl]-[3-methoxy-4-(4-methyl-imidazol-1-yl)-phenyl]-amine;
[4-(3,5-difluoro-phenyl)-4,5,6,7-tetrahydro-benzothiazol-2-yl]-[3-methoxy-4-(4-methyl-imidazol-1-yl)-phenyl]-amine;
[4-(3,5-trifluoromethyl-phenyl)-4,5,6,7-tetrahydro-benzothiazol-2-yl]-[3-methoxy-4-(4-methyl-imidazol-1-yl)-phenyl]-amine;
[3-methoxy-4-(4-methyl-imidazol-1-yl)-phenyl]-(4-methyl-4-phenyl-4,5,6,7-tetrahydro-benzothiazol-2-yl)-amine;
[3-fluoro-4-(4-methyl-imidazol-1-yl)-phenyl]-[4-(4-methyl-3-trifluoromethyl-phenyl)-4,5,6,7-tetrahydro-benzothiazol-2-yl]-amine;
[4-(2-chloro-phenyl)-4,5,6,7-tetrahydro-benzothiazol-2-yl]-[3-fluoro-4-(4-methyl-imidazol-1-yl)-phenyl]-amine;
[3-fluoro-4-(4-methyl-imidazol-1-yl)-phenyl]-[4-(2-methoxy-phenyl)-4,5,6,7-tetrahydro-benzothiazol-2-yl]-amine;
[4-(2,4-dichloro-phenyl)-4,5,6,7-tetrahydro-benzothiazol-2-yl]-[3-fluoro-4-(4-methyl-imidazol-1-yl)-phenyl]-amine;
2-(4-methyl-imidazol-1-yl)-5-(4-phenyl-4,5,6,7-tetrahydro-benzothiazol-2-ylamino)-phenol;
[4-(2-methyl-oxazol-5-yl)-phenyl]-(4-phenyl-4,5,6,7-tetrahydro-benzothiazol-2-yl)-amine;
[3-methoxy-4-(1-methyl-1H-pyrazol-4-yl)-phenyl]-(4-phenyl-4,5,6,7-tetrahydro-benzothiazol-2-yl)-amine;
[3-methoxy-4-(2-methyl-thiazol-5-yl)-phenyl]-(4-phenyl-4,5,6,7-tetrahydro-benzothiazol-2-yl)-amine;
[4-(2,4-dimethyl-thiazol-5-yl)-3-methoxy-phenyl]-(4-phenyl-4,5,6,7-tetrahydro-benzothiazol-2-yl)-amine;
(4-phenyl-4,5,6,7-tetrahydro-benzothiazol-2-yl)-(4-pyridin-4-yl-phenyl)-amine;
[4-(2-ethyl-oxazol-5-yl)-phenyl]-(4-phenyl-4,5,6,7-tetrahydro-benzothiazol-2-yl)-amine;
[4-(2,4-dimethyl-oxazol-5-yl)-phenyl]-(4-phenyl-4,5,6,7-tetrahydro-benzothiazol-2-yl)-amine; and
[4-(3-methyl-[1,2,4]thiadiazol-5-yl)-phenyl]-(4-phenyl-4,5,6,7-tetrahydro-benzothiazol-2-yl)-amine.

Further preferred compounds from formula I-A are those, wherein Y is —N(R)—, for example the following compounds
[5-benzyl-7-(2-chloro-phenyl)-4,5,6,7-tetrahydro-thiazolo[5,4-c]pyridin-2-yl]-[3-methoxy-4-(4-methyl-imidazol-1-yl)-phenyl]-amine and
[5-benzyl-7-(4-chloro-3-fluorophenyl)-4,5,6,7-tetrahydro-thiazolo[5,4-c]pyridin-2-yl]-[3-methoxy-4-(4-methyl-imidazol-1-yl)-phenyl]-amine.

Preferred are further compounds of formula

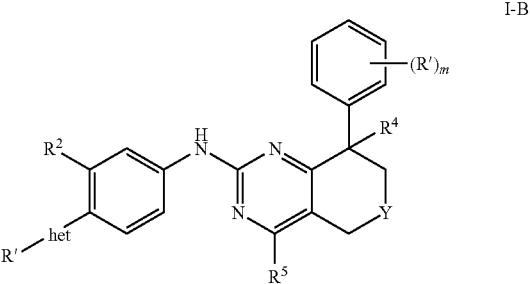

I-B wherein
het is a five- or six membered heteraryl group;
R' is hydrogen, halogen, lower alkyl, lower alkyl substituted by halogen, lower alkoxy or lower alkoxy substituted by halogen;
$R^2$ is hydrogen, lower alkoxy, hydroxy, lower alkyl, halogen or cyano;
$R^4$ is hydrogen, lower alkyl, hydroxy or $CH_2CN$;
$R^5$ is hydrogen, lower alkyl or hydroxy,
Y is a bond, —O—, —CH$_2$—, —CH$_2$—CH$_2$—, or —N(R)—;
R is hydrogen, lower alkyl, C(O)O-lower alkyl, C(O)-lower alkyl, S(O)$_2$-lower alkyl, or benzyl; and
m is 0, 1, or 2;
or a pharmaceutically active acid addition salt thereof Preferred compounds from formula I-B are those, wherein Y is —CH$_2$—, for example the following compounds
[3-fluoro-4-(4-methyl-imidazol-1-yl)-phenyl]-(8-phenyl-5,6,7,8-tetrahydro-quinazolin-2-yl)-amine;
[3-methoxy-4-(4-methyl-imidazol-1-yl)-phenyl]-(8-phenyl-5,6,7,8-tetrahydro-quinazolin-2-yl)-amine;
[8-(4-chloro-phenyl)-5,6,7,8-tetrahydro-quinazolin-2-yl]-[3-methoxy-4-(4-methyl-imidazol-1-yl)-phenyl]-amine;
[3-fluoro-4-(4-methyl-imidazol-1-yl)-phenyl]-[8-(4-fluoro-phenyl)-5,6,7,8-tetrahydro-quinazolin-2-yl]-amine;
2-[3-methoxy-4-(4-methyl-imidazol-1-yl)-phenylamino]-8-pyridin-3-yl-5,6,7,8-tetrahydro-quinazolin-8-ol;
[3-methoxy-4-(4-methyl-imidazol-1-yl)-phenyl]-(8-pyridin-2-yl-5,6,7,8-tetrahydro-quinazolin-2-yl)-amine; and
[3-methoxy-4-(4-methyl-imidazol-1-yl)-phenyl]-[8-(3,4,5-trifluoro-phenyl)-5,6,7,8-tetrahydro-quinazolin-2-yl]-amine.

Further preferred compounds from formula I-B are those, wherein Y is —N(R)—, for example the following compounds
2-[3-methoxy-4-(4-methyl-imidazol-1-yl)-phenylamino]-8-phenyl-7,8-dihydro-5H-pyrido[4,3-d]pyrimidine-6-carboxylic acid tert.-butyl ester;
[3-methoxy-4-(4-methyl-imidazol-1-yl)-phenyl]-(8-phenyl-5,6,7,8-tetrahydro-pyrido[4,3-d]pyrimidin-2-yl)-amine hydrochloride;

1-{2-[3-methoxy-4-(4-methyl-imidazol-1-yl)-phenylamino]-8-phenyl-7,8-dihydro-5H-pyrido[4,3-d]pyrimidin-6-yl}-ethanone;
(6-ethyl-8-phenyl-5,6,7,8-tetrahydro-pyrido[4,3-d]pyrimidin-2-yl)-[3-methoxy-4-(4-methyl-imidazol-1-yl)-phenyl]-amine; and
(6-isopropyl-8-phenyl-5,6,7,8-tetrahydro-pyrido[4,3-#d!]pyrimidin-2-yl)-[3-methoxy-4-(4-methyl-imidazol-1-yl)-phenyl]-amine.

The present compounds of formula I and their pharmaceutically acceptable salts can be prepared by methods known in the art, for example, by processes described below, which processes comprise a) reacting a compound of formula

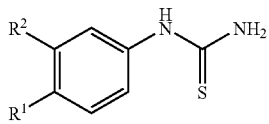

II with a compound of formula

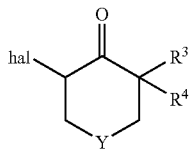

III to obtain a compound of formula

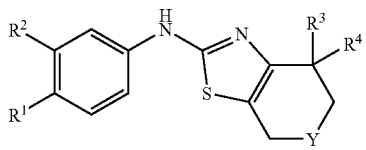

I-A-1 wherein the substituents have the meaning as described above or, b) reacting a compound of formula

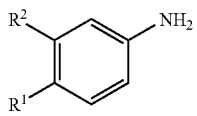

IV with a compound of formula

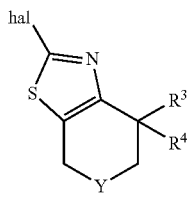

V to obtain a compound of formula

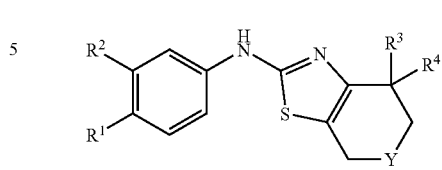

I-A-1 wherein the substituents have the meaning as described above or, c) reacting a compound of formula

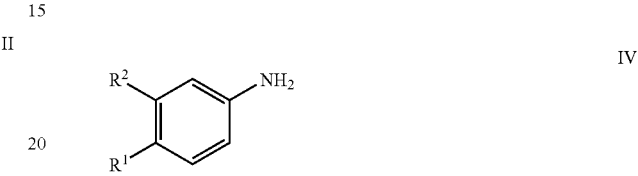

IV with a compound of formula

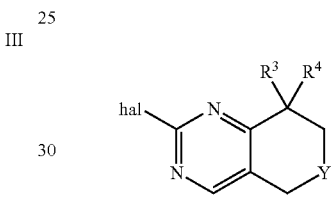

VI to obtain a compound of formula

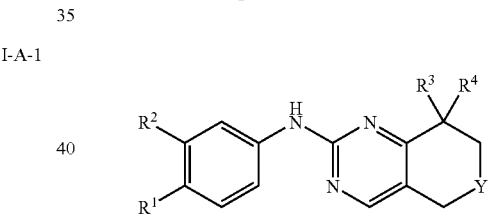

I-B-1 wherein the substituents have the meaning as described above or, d) reacting a compound of formula

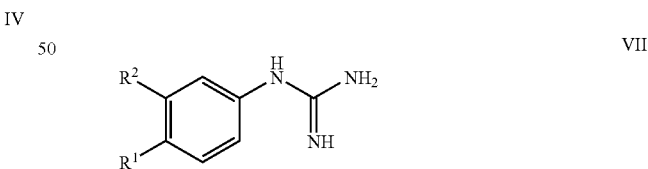

VII with a compound of formula

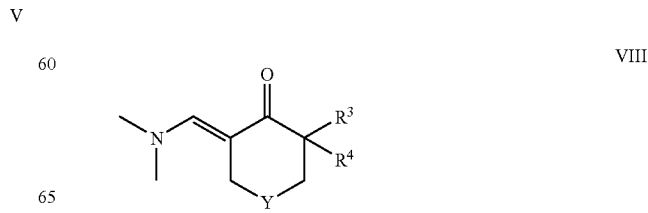

VIII to obtain a compound of formula

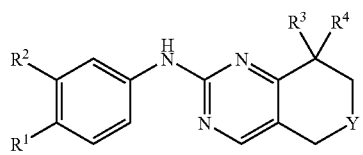

wherein the substituents have the meaning as described above and, if desired, converting the compounds obtained into pharmaceutically acceptable acid addition salts.

The detailed description can be found below and in Examples 1-97.

The preparation of compounds of formula I of the present invention can be carried out in sequential or convergent synthetic routes. Syntheses of the compounds of the invention are shown in the following schemes 1 to 6. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

The aniline respectively the thiourea, or respectively the guanidine, which can be used as starting materials for the preparation of compounds of formula I can be prepared as described in the following schemes:

$R^1$ is a hetaryl group and PG is a N-protecting group, such as tert-butoxycarbonyl (Boc) group. Nucleophilic substitution at room temperature or elevated temperature (e.g reflux or under pressure using a microwave oven) under neutral or basic conditions in the presence of a base (like e.g. potassium carbonate etc.) neat or in a polar solvent (like e.g. THF or DMSO etc.) of a substituted 4-nitro-phenyl halide IX with a 5-membered heteroaromatic ring (like e.g. imidazol, preferred is 5-methyl imidazol) yields the nitro derivative X which is reduced either under catalytic conditions (like e.g. 10% carbon on palladium) with hydrogen in a solvent (like e.g. ethanol or ethyl acetate) or with a metal (like e.g. iron) or metal salt (like e.g. stannous chloride) in a polar solvent (like e.g. acetic acid or tetrahydrofuran) to the aniline derivative IV. Alternatively the nitro derivative X can be prepared by Heck reaction of a suitable halide IX (hal is e.g. iodine or bromine) with a suitable hetaryl group $R^1H$ (like e.g. a thiazole) under catalytic conditions (like e.g. palladium(0) catalysis) under heating (e.g. in a microwave oven) in a polar solvent (like e.g. methanol) and in the presence of a base (like e.g. potassium fluoride). The halide IX can be also coupled to a hetary group via Suzuki (with a hetaryl boronic acid derivative like e.g. 1-methyl-4-(4,4,5,5-tetramethyl-1,3,2-dioxaborolan-2-yl)-1H-pyrazole) or Stille coupling (with a hetaryl tin compound) under palladium(0) catalysis in the presence of a base. These transformations also can be performed on other intermediates or on the final products bearing a halide instead of an hetaryl group. Alternatively aniline IV can be prepared from the corresponding N-protected 4-halo-aniline XI and the 5-membered heteroaromatic ring under catalytic conditions (like e.g. palladium(0) or copper(II) catalysis) after subsequent deprotection. The aniline IV can be converted to the thiourea TI either by treatment with a thiophosgene derivative (like e.g. 1,1'-thiocarbonyldi-2(1H)-pyridone) and subsequent aminolysis or by treatment with an acyl isothiocyanate (like e.g. benzoyl isothiocyanate) and subsequent hydrolysis. The guanidine VII can be prepared from aniline IV by reaction with cyanamide under acidic conditions (e.g. hydrochloric acid or nitric acid) in a protic solvent (like ethanol) or by treatment with a carboxamidine derivative like 3,5-dimethyl-pyrazole-1-carboxamidine, 2-methyl-isothiourea or sulfphoguanidine in polar or apolar medium with or without a base.

Scheme 1

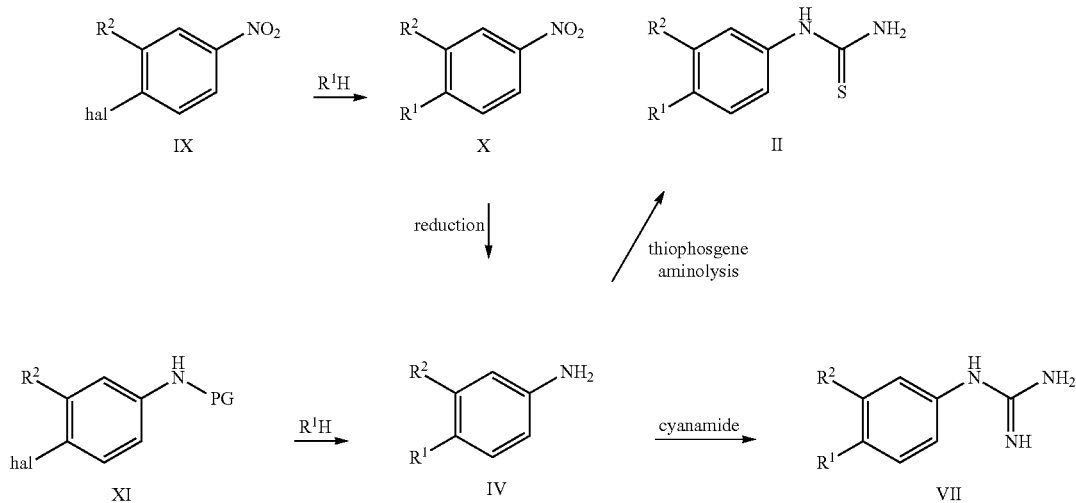

Scheme 2

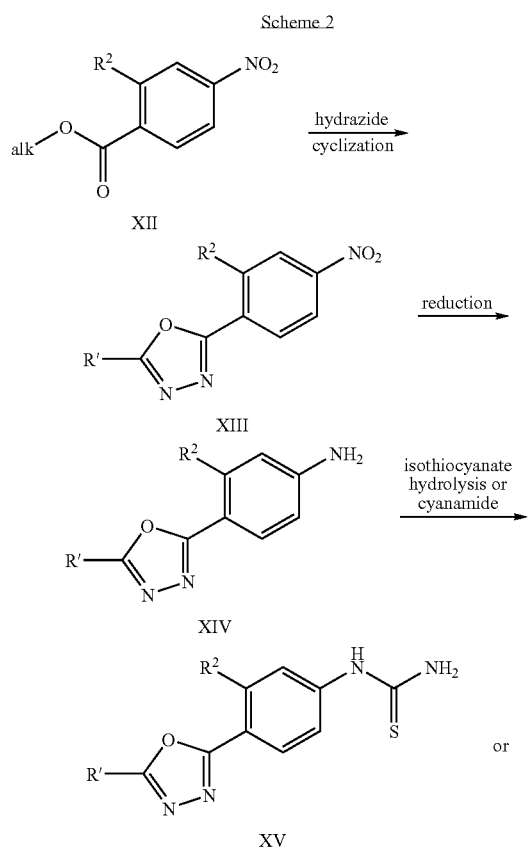

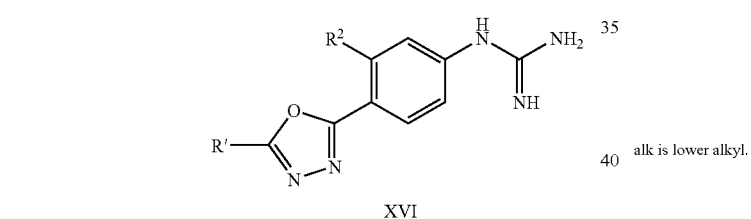

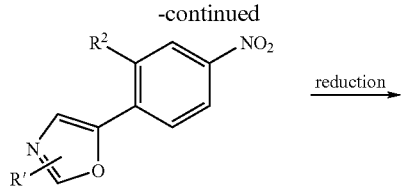

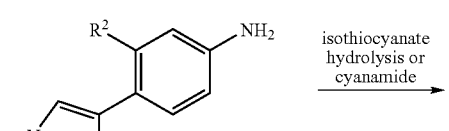

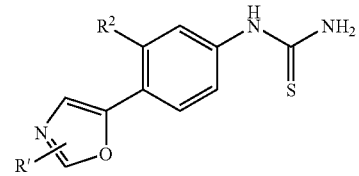

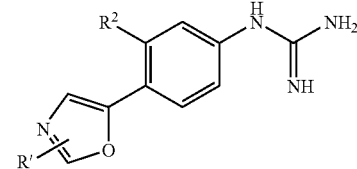

alk is lower alkyl.

Other heterocyclic anilines like the oxadiazole derivative XIII can be prepared from the corresponding esters XII by conversion to the acylated hydrazide and subsequent cyclization to the oxadiazol XIII. Treatment of the aldehyded XVII with TosMIC (tosylmethyl isocyanide) yields the oxazol XVIII. Reduction of XIII respectively XVIII to the anilines XIV and XIX and subsequent conversion with isothiocyanate derivative and hydrolysis or with cyanamide yields the thioureas XV and XX respectively the guanidines XVI and XXI.

Scheme 3

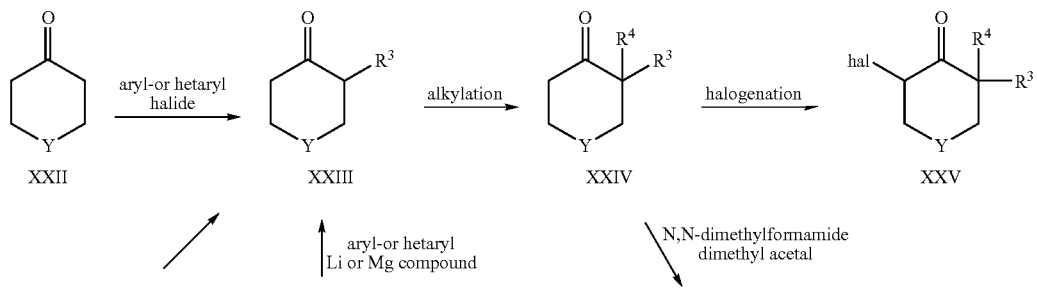

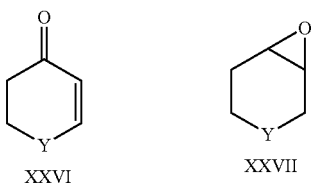

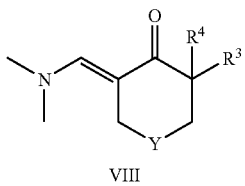

The 2-aryl ketones XXIII can be prepared from the ketone XXII by direct arylation with an aryl halide under basic conditions (e.g. NaOtBu) and Pd(0)-catalysis or through arylation of the beta-ketoester XXVI with an aryl halide under Pd(0) catalysis or with an hypervalent iodoaryl derivate and subsequent decarboxylation. Ketone XXIII can be also prepared by the addition of an aryl lithium species under lewis acid catalysis or of an aryl magnesium derivative from the epoxide XXVII and subsequent oxidation of the alcohol to the ketone. Optional alkylation of the ketone yields XXIV. The alpha-halo-ketones XXV can be prepared from the corresponding ketones XXIV through halogenation with either elemental halogen or a halide transferring agent (like e.g. NXS etc.). Preparation of the enamine VIII can be achieved by reaction with an aminal of DMF (like N,N-diemethylformamide diemthyl acetal or the Bredereck's reagent (tert.-butoxy-bis(dimethylamino)methane)).

Scheme 4

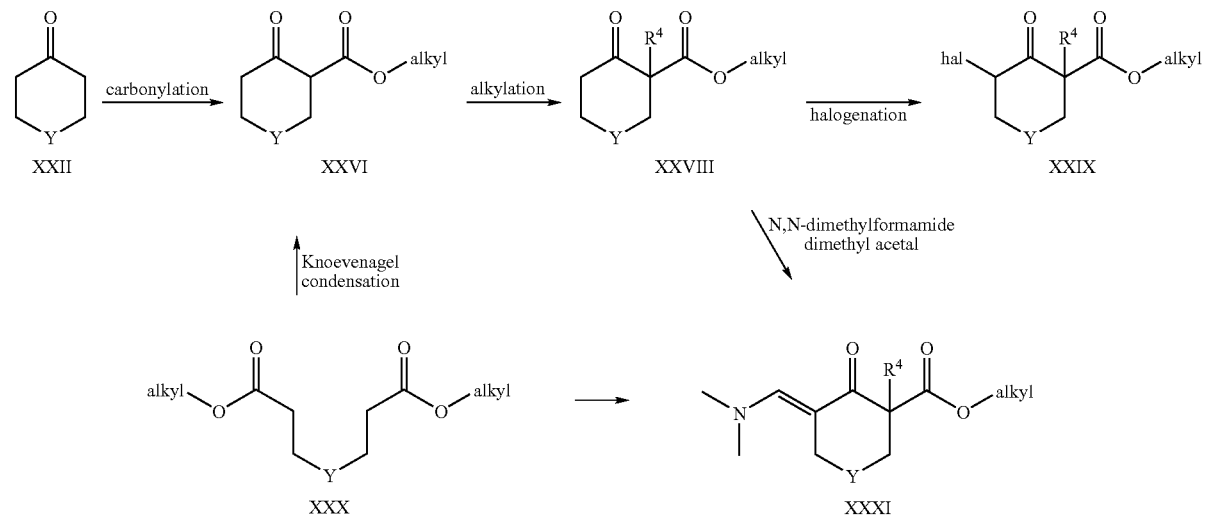

The beta-keto esters XXVI can be prepared from the ketone XXII by direct carboxylation with dimethyl carbonate, Mander's reagent or similar reagents or from the diester XXX by Knoevenagel condensation. This ester XXVI can be converted by optional alkylation to compound XXVIII and to the alpha-halo-ketones XXIX and to the enamines XXXI as described in scheme 3.

Scheme 5

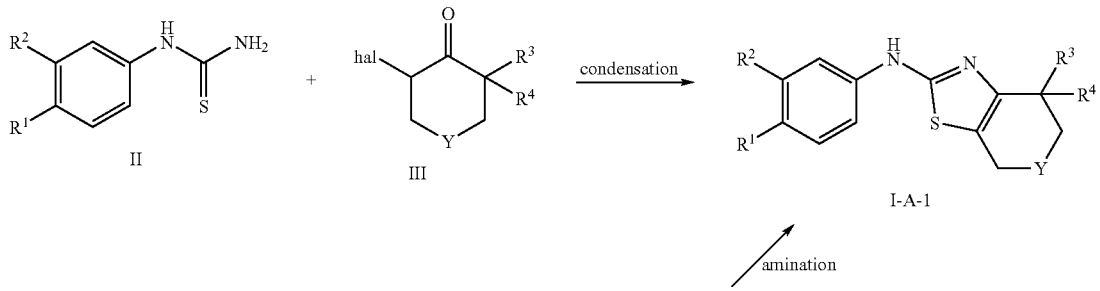

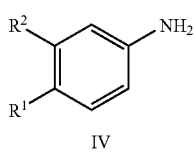 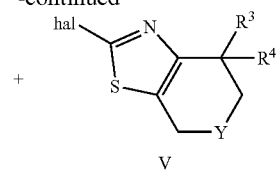

IV + V

Condensation of the thiourea II with the alpha-halo-ketones III in an inert solvent (like e.g. ethanol) at room temperature or elevated temperature in the presence or absence of a base (like e.g. potassium carbonate or Hünigs base) yields the aminothiazoles I-A-1. Alternatively compounds of structure I-A-1 can also be prepared through direct amination of a suitable 2-halo-thiazole V with the aniline IV in the presence of a catalyst and a ligand (like e.g. palladium(O) and a phosphine ligand or copper(II) and a phenanthrene ligand).

After incubation for 22 hrs at 37° C., 5% CO2, 50 μl supernatant was transferred into round-bottom 96-well polypropylene plates for detection of Aβ42. 50 μl assay buffer (50 mM Tris/Cl, pH 7.4, 60 mM NaCl, 0.5% BSA, 1% TWEEN 20) was added to the wells followed by the addition of 100 μl of detection antibody (ruthenylated Aβ42-specific antibody BAP15 0.0625 μg/mL in assay buffer). 50 μl of a premix of capture antibody (biotinylated 6E10 antibody, 1 μg/mL) and Steptavidin-coated magnetic beads (Dynal M-280, 0.125 mg/mL) were preincubated for 1 hr at room Scheme 6

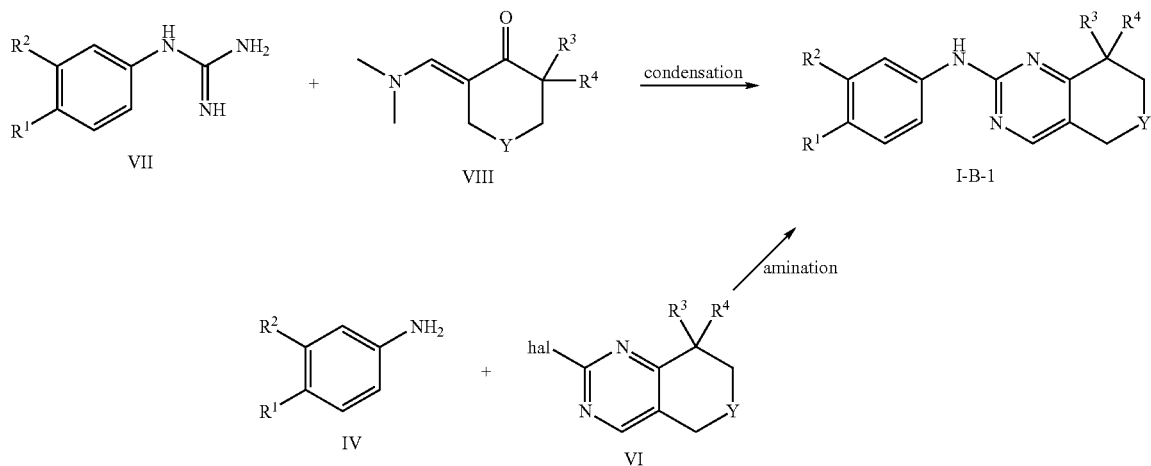

Condensation of the guanidine VII with the enamine VIII in a polar or unpolar solvent at room temperature or at elevated temperatures in the presence or without a base yields the pyrimidine I-B-1. Alternatively compounds of structure I-B-1 can be prepared by coupling the aniline IV with a suitable 2-halo-pyrimidine VI under thermal or under Pd(0)-catalyzed conditions. The compounds were investigated in accordance with the test given hereinafter.

Description of γ-Secretase Assay

Cellular γ-Secretase Assay

Human neuroglioma H4 cells overexpressing human APP were plated at 30,000 cells/well/200 μl in 96-well plates in IMDM media containing 10% FCS, 0.2 mg/l Hygromycin B and incubated for 2 h at 37° C., 5% CO2 prior to adding test compounds.

Compounds for testing were dissolved in 100% Me$_2$SO yielding in a 10 mM stock solution. Typically 12 μl of these solutions were further diluted in 1000 μl of IMDM media (w/o FCS,). Sub sequential 1:1 dilutions gave a ten point dose response curve. 100 μl of each dilution was added to the cells in 96-well plates. Appropriate controls using vehicle only and reference compound were applied to this assay. The final concentration of Me$_2$SO was 0.4%.

temperature before adding the assay plates. Assay plates were incubated on a shaker for 3 hrs at room temperature and finally read in the Bioveris M8 Analyser according to the manufacturer's instructions (Bioveris).

Toxicity of compounds was monitored by a cell viability test of the compound-treated cells using a calorimetric assay (CellTiter 96TM AQ assay, Promega) according to the manufacturer's instructions. Briefly, after removal of 50 μl cell culture supernatant for detection of Aβ42, 20 μl of 1× MTS/PES solution was added to the cells and incubated for 30 min at 37° C., 5% CO$_2$. Optical density was then recorded at 490 nm.

$EC_{50}$ values for inhibition of Aβ42 secretion were calculated by nonlinear regression fit analysis using XLfit 4.0 software (IDBS).

The preferred compounds show a $EC_{50}$<0.5 (μM). In the list below are described the data to γ-secretase inhibition for some compounds of the invention:

| Example No. | $EC_{50}$ in vitro (μM) |
| --- | --- |
| 1 | 0.30 |
| 5 | 0.05 |

-continued

| Example No. | EC$_{50}$ in vitro (μM) |
|---|---|
| 6 | 0.04 |
| 7 | 0.11 |
| 9 | 0.10 |
| 10 | 0.10 |
| 12 | 0.16 |
| 13 | 0.12 |
| 14 | 0.07 |
| 15 | 0.09 |
| 16 | 0.09 |
| 18 | 0.13 |
| 19 | 0.26 |
| 21 | 0.12 |
| 23 | 0.07 |
| 24 | 0.07 |
| 25 | 0.1 |
| 26 | 0.08 |
| 27 | 0.07 |
| 28 | 0.12 |
| 29 | 0.1 |
| 30 | 0.30 |
| 32 | 0.26 |
| 33 | 0.43 |
| 35 | 0.34 |
| 36 | 0.46 |
| 38 | 0.13 |
| 39 | 0.48 |
| 40 | 0.27 |
| 41 | 0.34 |
| 42 | 0.50 |
| 44 | 0.32 |
| 50 | 0.38 |
| 60 | 0.5 |
| 66 | 0.21 |
| 68 | 0.13 |
| 69 | 0.25 |
| 71 | 0.47 |
| 80 | 0.45 |
| 83 | 0.45 |
| 91 | 0.24 |
| 92 | 0.252 |
| 93 | 0.212 |
| 94 | 0.32 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of the γ-secretase, such as of Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Example 1

(3-Methoxy-4-oxazol-5-yl-phenyl)-(4-phenyl-4,5,6,7-tetrahydro-benzothiazol-2-yl)-amine

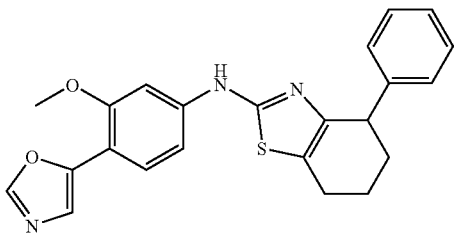

a) (3-Methoxy-4-oxazol-5-yl-phenyl)-thiourea

3-Methoxy-4-(1,3-oxazol-5-yl)-aniline (200 mg, 1.05 mmol) was dissolved in tetrahydrofuran (9 mL). At room temperature under an atmosphere of nitrogen benzoylisothiocyanate (190 mg, 1.10 mmol) was added. The reaction was stirred at room temperature for 4 hours. The solvent was evaporated under reduced pressure and the residue was dissolved in methanol (13.5 mL). Potassium carbonate (436 mg, 3.16 mmol) dissolved in water (6.8 mL) was added over 10 minutes. The reaction was stirred over night at room temperature under an atmosphere of nitrogen. A solid precipitated. The solvent was evaporated under reduced pressure; the solid was filtered off and washed thoroughly with water. The product was dried at high vacuum to yield the title compound (253 mg, 97%) as a yellow solid. MS ISP (m/e): 248.3 (100) [(M+H)$^+$]. $^1$H NMR (DMSO-D$_6$, 300 MHz): δ (ppm)=9.88 (s, 1H), 8.39 (s, 1H), 7.90-7.20 (br s, 2H), 7.62 (d, 1H), 7.48 (br s, 2H), 7.08 (d, 1H), 3.92 (s, 3H).

b) (3-Methoxy-4-oxazol-5-yl-phenyl)-(4-phenyl-4,5,6,7-tetrahydro-benzothiazol-2-yl)-amine A suspension of (3-methoxy-4-oxazol-5-yl-phenyl)-thiourea (74.8 mg, 0.3 mmol) and of 2-bromo-6-phenyl-cyclohexanone (75.9 mg, 0.3 mmol, preparation: WO9404487) in ethanol (4 mL) was heated over night to reflux under an atmosphere of nitrogen. After cooling to room temperature the solvent was evaporated under reduced pressure and the residue was purified on silica gel using dichloromethane/methanol (19:1 v/v) as eluent to yield the title compound (101 mg, 83%) as an off-white foam. MS ISP (m/e): 404.5 (100) [(M+H)$^+$]. $^1$H NMR (DMSO-D$_6$, 300 MHz): δ (ppm)=10.29 (s, 1H), 8.31 (s, 1H), 7.66 (s, 1H), 7.50 (d, 1H), 7.46-7.51 (m, 3H), 7.09-7.31 (m, 3H), 6.83 (s, 1H), 4.00 (m, 1H), 3.46 (s, 3H), 2.73 (m, 2H), 2.12 (m, 1H), 1.70-1.94 (m, 3H).

Example 2

(4-Phenyl-4,5,6,7-tetrahydro-benzothiazol-2-yl)-(4-[1,2,4]triazol-1-yl-phenyl)-amine

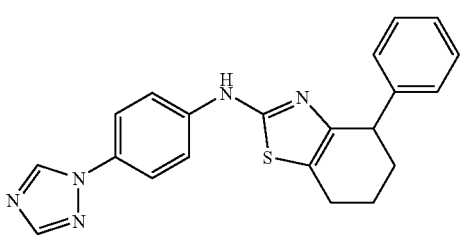

A suspension of 4-(1,2,4-triazol-1-yl)phenylthiourea (109.6 mg, 0.5 mmol) and of 2-bromo-6-phenyl-cyclohexanone (253.1 mg, 1.00 mmol) in ethanol (4 mL) was heated for two days to reflux under an atmosphere of nitrogen. After cooling to room temperature the solvent was evaporated under reduced pressure and the residue was treated with dichloromethane, diethyl ether and heptane. The product precipitated as a solid and was filtered off to yield the title compound (120 mg, 64%) as a pale-brown solid. MS ISP (m/e): 374.3 (100) [(M+H)$^+$]. $^1$H NMR (DMSO-D$_6$, 300 MHz): δ (ppm)=10.4 (s, 1H), 9.38 (s, 1H), 8.29 (s, 1H), 8.02 (d, 2H), 7.56 (d, 2H), 7.30 (t, 2H), 7.10-7.19 (m, 5H), 4.00 (m, 1H), 2.72 (m, 2H), 2.14 (m, 1.70-1.89 (m, 3H).

Example 3

4-(4-Phenyl-4,5,6,7-tetrahydro-benzothiazol-2-ylamino)-benzoic acid methyl ester

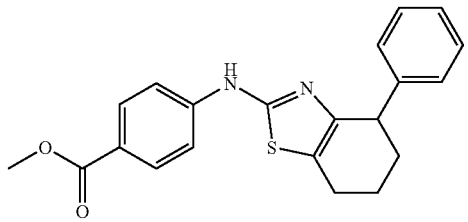

A suspension of 1-(4-ethoxycarbonylphenyl)-2-thiourea (105 mg, 0.5 mmol) and of 2-bromo-6-phenyl-cyclohexanone (253.1 mg, 1.00 mmol) in ethanol (4 mL) was heated for two days to reflux under an atmosphere of nitrogen. After cooling to room temperature the solvent was evaporated under reduced pressure and the residue was dissolved in dichloromethane. The product was precipitated with diethyl ether and heptane as an oil, which was purified on silica gel with dichloromethane as eluent to yield the title compound (120 mg, 63%) as a pale-yellow solid. $^1$H NMR (DMSO-D$_6$, 300 MHz): δ (ppm)=10.42 (s, 1H), 7.77 (d, 2H), 7.50 (d, 2H), 7.28 (t, 2H), 7.27 (t, 1H), 7.12 (d, 2H), 4.23 (q, 2H), 4.06 (m, 1H), 2.73 (m, 2H), 2.12 (m, 1H), 1.70-1.90 (m, 3H), 1.27 (t, 3H).

Example 4

[3-Methoxy-4-(4-methyl-imidazol-1-yl)-phenyl]-[4-(4-trifluoromethoxy-phenyl)-4,5,6,7-tetrahydro-benzothiazol-2-yl]-amine

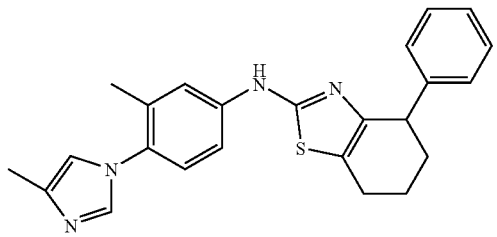

a) 4-Methyl-1-(2-methyl-4-nitro-phenyl)-1H-imidazole

A mixture of 2-chloro-5-nitro-toluene (2.0 g, 12 mmol), of 4-methylimidazole (1.0 g, 12 mmol) and of cesium carbonate (5.7 g, 17.5 mmol) in acetonitrile (20 mL) was refluxed overnight. The reaction mixture was cooled, quenched by addition of water and extracted with ethyl acetate. The solvent was removed under reduced pressure and the crude material was purified by column chromatography on silica gel using ethyl acetate as eluent to yield the title compound (1.27 g, 50%) as a slightly brownish solid. MS ISP (m/e): 218.3 (100) [(M+H)$^+$].

b) 3-Methyl-4-(4-methyl-imidazol-1-yl)-phenylamine

A mixture of 4-methyl-1-(2-methyl-4-nitro-phenyl)-1H-imidazole (1.26 g, 5.8 mmol) and of stannous chloride dehydrate (6.81 g, 30.2 mmol) in ethyl acetate (40 mL) and ethanol (20 mL) was stirred for 1 hour at 70° C. The reaction mixture was quenched by addition of water, neutralized with sodium hydrogen carbonate and extracted with ethyl acetate. The organic layer was dried over sodium sulfate, filtered and concentrated under reduced pressure to give the crude title compound (1.08 g, 99%) as a yellowish gum. MS ISP (m/e): 188.4 (100) [(M+H)$^+$].

c) 3-Methyl-4-(4-methyl-imidazol-1-yl)-phenyl]-thiourea

A solution of 3-methyl-4-(4-methyl-imidazol-1-yl)-phenylamine (1.07 g, 5.7 mmol) in tetrahydrofuran (40 mL) was treated with benzylisothiocyanate (0.98 g, 6.0 mmol) and stirred 1 hour at room temperature. The reaction mixture was concentrated under reduced pressure and carefully neutralized by addition of an aqueous solution of 2M aqueous potassium carbonate solution. After stirring for 1 hour at room temperature, the methanol was removed under reduced pressure; the resulting crystals were filtered off and dried to give the crude title compound (1.06 g, 75%) as a slightly brownish solid. MS ISP (m/e): 247.1 (100) [(M+H)$^+$].

d) [3-Methoxy-4-(4-methyl-imidazol-1-yl)-phenyl]-[4-(4-trifluoromethoxy-phenyl)-4,5,6,7-tetrahydro-benzothiazol-2-yl]-amine A suspension of 3-methyl-4-(4-methyl-imidazol-1-yl)-phenyl]-thiourea (30.2 mg, 0.12 mmol) and of 2-bromo-6-phenyl-cyclohexanone (56.0 mg, 0.22 mmol) in ethanol (2 mL) was heated over night to reflux under an atmosphere of nitrogen. After cooling to room temperature the solvent was evaporated under reduced pressure and the residue was purified on silica gel using dichloromethane then dichloromethane/methanol (19:1 v/v) as eluent to yield the title compound (40 mg, 82%) as an off-white foam. MS ISP (m/e): 401.3 (100) [(M+H)$^-$]. $^1$H NMR (DMSO-D$_6$, 300 MHz): δ (ppm)=10.11 (s, 1H), 7.55 (s, 1H), 7.39 (s, 1H), 7.28-7.45 (m, 4H), 7.10-7.20 (m, 2H), 7.08 (d, 1H), 6.96 (s, 1H), 4.03 (m, 1H), 2.20 (m, 2H), 2.13 (s, 3H), 1.98 (s, 3H), 1.79 (m, 2H), 1.13 (m, 2H).

Example 5

[3-Fluoro-4-(4-methyl-imidazol-1-yl)-phenyl]-(4-phenyl-4,5,6,7-tetrahydro-benzothiazol-2-yl)-amine

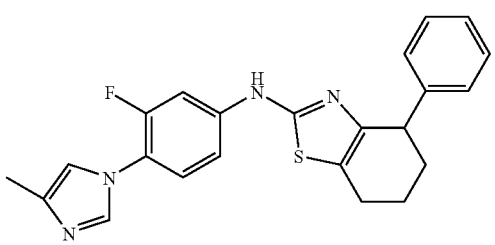

a) 1-(2-Fluoro-4-nitro-phenyl)-4-methyl-1H-imidazole 3,4-Difluoronitrobenzene (7.97 g, 50 mmol), 2-methylimidazole (4.51 g, 55 mmol) and N,N-diisopropylethylamine (16.16 g, 125 mmol) were dissolved in acetonitrile (80 mL) and the reaction was heated to reflux for 24 hours under an atmosphere of nitrogen. The solvent was evaporated under reduced pressure and the residue was crystallized from a mixture of ethyl acetate and heptane to yield the title compound (4.66 g, 42%) as a pale-yellow solid. MS ISP (m/e): 222.1 (100) [(M+H)$^+$]. $^1$H NMR (DMSO-D$_6$, 300 MHz): δ (ppm)=8.42 (d, 1H), 8.21 (d, 1H), 8.11 (s, 1H), 7.95 (t, 1H), 7.43 (s, 1H), 2.19 (s, 3H).

b) 3-Fluoro-4-(4-methyl-imidazol-1-yl)-phenylamine 1-(2-Fluoro-4-nitro-phenyl)-4-methyl-1H-imidazole (4.66 g, 21.1 mmol) was dissolved in a mixture of methanol (25 mL) and tetrahydrofuran (100 mL). The solution was cooled to 0° C. under an atmosphere of nitrogen. Ammonium formiate (6.64 g, 105 mmol) and 10% palladium on charcoal (0.24 g) were added and the mixture was stirred at ambient temperature for 18 hours. It was filtered through celite. The celite was washed with methanol and the filtrate was evaporated under reduced pressure to dryness. The residue was partitioned between ethyl acetate and 10% aqueous sodium bicarbonate solution. The organic layer was separated, washed with brine, dried over sodium sulfate and the solvent was evaporated under reduced pressure to yield the title compound (3.89 g, 97%) as a yellow solid. $^1$H NMR (DMSO-D$_6$, 300 MHz): δ (ppm)=7.62 (s, 1H), 7.12 (t, 1H), 7.01 (s, 1H), 6.41-6.51 (m, 2H), 5.64 (br s, 2H), 2.13 (s, 3H).

c) [3-Fluoro-4-(4-methyl-imidazol-1-yl)-phenyl]-thiourea

3-Fluoro-4-(4-methyl-imidazol-1-yl)-phenylamine (956 mg, 5 mmol) was dissolved in tetrahydrofuran (50 mL). Benzoyl isocyanate (897 mg, 5.5 mmol) was added and the reaction was stirred at room temperature for two hours. The solvent was removed under reduced pressure and the residue was suspended in methanol (75 mL). Potassium carbonate (2073 mg, 15 mmol) dissolved in water (38 mL) was added drop wise to the suspension. The reaction was stirred at room temperature over night to yield a solution. The solvent was removed under reduced pressure and the residue was suspended in water, filtered off, washed with water and diethyl ether. The product was dissolved in tetrahydrofuran, the solvent was removed under reduced pressure and the residue was dried under reduced pressure to yield the title compound (1280 mg, 100%) as an off-white solid. MS ISP (m/e): 251.1 (100) [(M+H)+]. $^1$H NMR (DMSO-D$_6$, 300 MHz): δ (ppm)=9.98 (s, 1H), 7.84 (s, 1H), 7.82 (d, 1H), 7.52 (t, 1H), 7.29 (d, 1H), 7.20 (s, 1H), 2.16 (s, 3H).

d) [3-Fluoro-4-(4-methyl-imidazol-1-yl)-phenyl]-(4-phenyl-4,5,6,7-tetrahydro-benzothiazol-2-yl)-amine A suspension of [3-fluoro-4-(4-methyl-imidazol-1-yl)-phenyl]-thiourea (125 mg, 0.50 mmol) and of 2-bromo-6-phenyl-cyclohexanone (253 mg, 1.00 mmol) in ethanol (4 mL) was stirred at room temperature for 30 minutes and then heated for two days to reflux under an atmosphere of nitrogen. After cooling to room temperature the solvent was evaporated under reduced pressure and the residue was purified on silica gel using dichloromethane and then dichloromethane/methanol (19:1 v/v) as eluent to yield the title compound (200 mg, 99%) as a white solid. MS ISP (m/e): 405.4 (100) [(M+H)+]. $^1$H NMR (DMSO-D$_6$, 300 MHz): δ (ppm)=10.40 (s, 1H), 7.73 (s, 1H), 7.67 (d, 1H), 7.38 (t, 1H), 7.32 (t, 2H), 7.10-7.21 (m, 4H), 4.04 (m, 1H), 2.70 (m, 2H), 2.13 (s, 3H), 2.11 (m, 1H), 1.70-1.89 (m, 3H).

Example 6

[3-Methoxy-4-(4-methyl-imidazol-1-yl)-phenyl]-(4-phenyl-4,5,6,7-tetrahydro-benzothiazol-2-yl)-amine

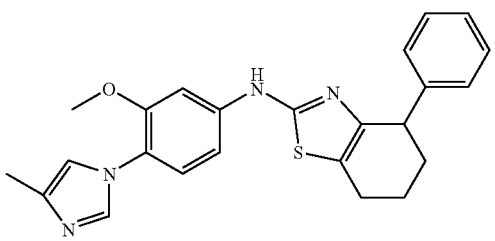

a) 1-(2-Methoxy-4-nitro-phenyl)-4-methyl-1H-imidazole

A solution of 2-chloro-5-nitroanisol (187 mg, 1 mmol), of 4-methylimidazol (335 mg, 4 mmol) and of potassium hydroxide (99 mg, 1.5 mmol) in DMSO (0.86 mL) was stirred for 5 hours at 80° under an atmosphere of nitrogen. After cooling to room temperature the reaction was poured onto ice/water. A precipitation was formed and the suspension was stirred for 15 minutes. The solid was filtered off, washed with water, dissolved in dichloromethane, dried over sodium sulfate, filtered and the solvent was evaporated under reduced pressure to yield a yellow solid. The crude product was purified on silica gel using dichloromethane/methanol (19:1 v/v) as eluent to yield the title compound (106 mg, 45%) as a pale-yellow solid. Alternatively the product can be also crystallized from the crude material from diethyl ether. MS ISP (m/e): 234.3 (100) [(M+H)+]. $^1$H NMR (CDCl$_3$, 300 MHz): δ (ppm)=7.97 (d, 1H), 7.96 (s, 1H), 7.83 (s, 1H), 7.42 (d, 1H), 7.00 (s, 1H), 4.00 (s, 3H), 2.31 (s, 3H).

b) 3-Methoxy-4-(4-methyl-imidazol-1-yl)-phenylamine 1-(2-Methoxy-4-nitro-phenyl)-4-methyl-1H-imidazole (2520 mg, 10.8 mmol) dissolved in ethanol (110 mL) was stirred under an atmosphere of hydrogen at room temperature for 3½ hours in the presence of 10% palladium on charcoal (252 mg). The catalyst was filtered off and washed with ethanol. The solvent of the filtrate was evaporated under reduced pressure. The crude product was purified on silica gel using dichloromethane/methanol (19:1 v/v) as eluent. The fraction containing the product was suspended in diethyl ether, stirred for 15 minutes, filtered and dried to yield the title compound (1719 mg, 78%) as a yellow solid. MS ISP (m/e): 204.3 (100) [(M+H)+]. $^1$H NMR (CDCl$_3$, 300 MHz): δ (ppm)=7.48 (s, 1H), 6.91 (d, 1H), 6.88 (s, 1H), 6.35 (s, 1H), 6.17 (d, 1H), 3.68 (s, 3H), 2.11 (s, 3H).

c) 1-(4-Isothiocyanato-2-methoxy-phenyl)-4-methyl-1H-imidazole

A solution of 3-methoxy-4-(4-methyl-imidazol-1-yl)-phenylamine (203 mg, 1 mmol) and of 1,1'-thiocarbonyldi-2(1H)-pyridone (263 mg, 1.1 mmol) in dichloromethane (10 mL) was stirred at room temperature over night to yield an orange solution. The reaction was concentrated under reduced pressure to ¼ of its volume and directly purified on silica gel using dichloromethane/methanol (95:5 v/v) as eluent to yield the title compound (230 mg, 94%) as a yellow oil, which solidifies on standing. MS ISP (m/e): 246.3 (100) [(M+H)+]. $^1$H NMR (CDCl$_3$, 300 MHz): δ (ppm)=7.67 (s, 1H), 7.21 (d, 1H), 6.91-6.86 (m, 3H), 3.86 (s, 3H), 2.29 (s, 3H).

d) [3-Methoxy-4-(4-methyl-imidazol-1-yl)-phenyl]-thiourea 1-(4-Isothiocyanato-2-methoxy-phenyl)-4-methyl-1H-imidazole (227 mg, 0.93 mmol) was dissolved in tetrahydrofuran (2.3 mL). At 0° C. under stirring ammonia gas was bubbled through the solution for 5 minutes. A solid precipitated. The suspension was stirred at room temperature over night. The solvent was evaporated under reduced pressure and the residue was stirred with diethyl ether for 30 minutes. The solid was filtered off and dried to yield the title compound (170 mg, 70%) as a pale-yellow solid. MS ISP (m/e): 263.3 (100) [(M+H)+]. $^1$H NMR (DMSO-D$_6$, 300 MHz): δ (ppm)=9.84 (s, 1H), 7.90-7.20 (br s, 2H), 7.71 (s, 1H), 7.46 (s, 1H), 7.28 (d, 1H), 7.07 (s, 1H), 7.03 (d, 1H), 3.79 (s, 3H), 2.15 (s, 3H).

e) [3-Methoxy-4-(4-methyl-imidazol-1-yl)-phenyl]-(4-phenyl-4,5,6,7-tetrahydro-benzothiazol-2-yl)-amine A suspension of [3-methoxy-4-(4-methyl-imidazol-1-yl)-phenyl]-thiourea (131.2 mg, 0.5 mmol) and of 2-bromo-6-phenyl-cyclohexanone (139.2 mg, 0.55 mmol) in ethanol (5 mL) was stirred at room temperature over the weekend. A clear yellow solution was obtained which was heated over night to reflux under an atmosphere of nitrogen. After cooling to room temperature the solvent was evaporated under reduced pressure and the residue was purified by column chromatography on silica gel using dichloromethane/methanol (19:1 v/v) as eluent to yield the title compound (110 mg, 53%) as a white solid. MS ISP (m/e): 417.5 (100) [(M+H)+]. $^1$H NMR (DMSO-D$_6$, 300 MHz): δ (ppm)=10.19 (s, 1H), 7.66 (s, 1H), 7.57 (s, 1H), 7.27 (t, 2H), 7.11-7.18 (m, 4H), 6.95 (s, 1H), 6.71 (d, 1H), 3.98 (m, 1H), 3.34 (s, 3H), 2.73 (m, 2H), 2.14 (m, 1H), 2.10 (s, 3H), 1.70-1.91 (m, 3H).

Example 7

[3-Methoxy-4-(4-methyl-imidazol-1-yl)-phenyl]-[4-(2-methoxy-phenyl)-4,5,6,7-tetrahydro-benzothiazol-2-yl]-amine

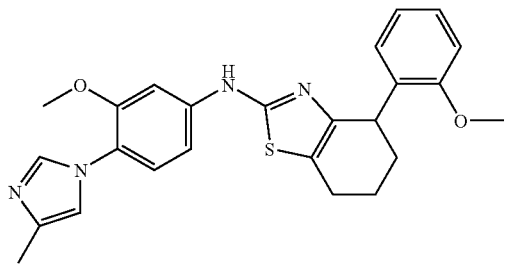

a) 2-Bromo-6-(2-methoxy-phenyl)-cyclohexanone 2-(2-Methoxy-phenyl)-cyclohexanone (51 mg, 0.27 mmol) was dissolved in chloroform (1 mL). To this solution bromine (45.4 mg, 0.28 mmol) in chloroform (0.5 mL) was added drop wise at room temperature. The reaction was stirred for 3 hours at room temperature and the solvent was removed under reduced pressure to yield the crude title compound (49 mg) which was used directly in the next step without further purification.

b) [3-Methoxy-4-(4-methyl-imidazol-1-yl)-phenyl]-[4-(2-methoxy-phenyl)-4,5,6,7-tetrahydro-benzothiazol-2-yl]-amine A suspension of [3-methoxy-4-(4-methyl-imidazol-1-yl)-phenyl]-thiourea (43 mg, 0.16 mmol) and of crude 2-bromo-6-phenyl-cyclohexanone (49 mg, 0.17 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (15 mg, 21%) as a yellow gum. MS ISP (m/e): 447.3 (100) [(M+H)$^+$]. $^1$H NMR (CDCl$_3$, 300 MHz): δ (ppm)=7.59 (s, 1H), 7.29 (s, 1H), 7.07-7.18 (m, 2H), 6.82-6.88 (m, 4H), 6.65 (d, 1H), 4.49 (m, 1H), 3.84 (s, 3H), 3.57 (s, 3H), 2.89 (m, 2H), 2.88 (s, 3H), 2.14 (m, 1H), 1.70-1.91 (m, 3H).

Example 8

[3-Methoxy-4-(4-methyl-imidazol-1-yl)-phenyl]-[4-(3-methoxy-phenyl)-4-propyl-4,5,6,7-tetrahydro-benzothiazol-2-yl]-amine

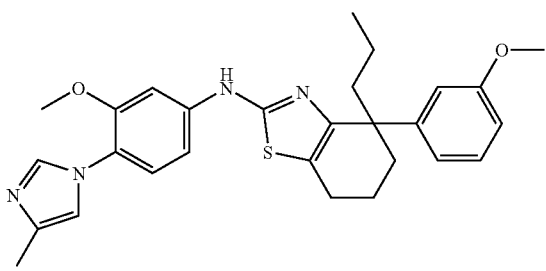

a) 6-Bromo-2-(3-methoxy-phenyl)-2-propyl-cyclohexanone 2-(3-Methoxy-phenyl)-2-propyl-cyclohexanone (100 mg, 0.41 mmol) was dissolved in chloroform (1 mL). To this solution bromine (68.1 mg, 0.43 mmol) in chloroform (0.5 mL) was added drop wise at −11° C. The reaction was stirred at 5° C. for 1½ hours, at room temperature for 1 hour and at 50° C. for 1 hour. The solvent was removed under reduced pressure to yield the crude title compound (126 mg) which was used directly in the next step without further purification.

b) [3-Methoxy-4-(4-methyl-imidazol-1-yl)-phenyl]-[4-(3-methoxy-phenyl)-4-propyl-4,5,6,7-tetrahydro-benzothiazol-2-yl]-amine A suspension of [3-methoxy-4-(4-methyl-imidazol-1-yl)-phenyl]-thiourea (100 mg, 0.38 mmol) and of crude 6-bromo-2-(3-methoxy-phenyl)-2-propyl-cyclohexanone (126 mg, 0.39 mmol) in ethanol (5 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (5 mg, 3%) as a yellow solid. MS ISP (m/e): 489.3 (100) [(M+H)$^-$]. $^1$H NMR (CDCl$_3$, 300 MHz): δ (ppm)=7.64 (s, 1H), 7.58 (d, 1H), 7.12-7.19 (m, 2H), 6.68-6.89 (m, 5H), 3.76 (s, 6H), 2.67 (m, 2H), 2.29 (s, 3H), 1.05-2.16 (m, 8H), 0.89 (t, 3H).

Example 9

[3-Methoxy-4-(4-methyl-imidazol-1-yl)-phenyl]-[4-(4-methyl-3-trifluoromethyl-phenyl)-4,5,6,7-tetrahydro-benzothiazol-2-yl]-amine

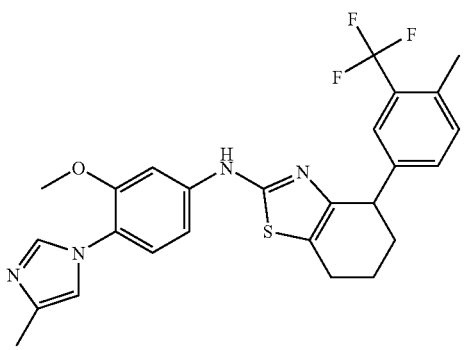

a) 6-Bromo-2-(4-methyl-3-trifluoromethyl-phenyl)-cyclohexanone 2-(4-Methyl-3-trifluoromethyl-phenyl)-cyclohexanone (50 mg, 0.20 mmol) was dissolved in chloroform (1 mL). To this solution bromine (32.7 mg, 0.21 mmol) in chloroform (0.5 mL) was added drop wise at room temperature. The reaction was stirred for 1½ hours at room temperature. The solvent was removed under reduced pressure to yield the title compound (70 mg) which was used directly in the next step without further purification.

b) [3-Methoxy-4-(4-methyl-imidazol-1-yl)-phenyl]-[4-(4-methyl-3-trifluoromethyl-phenyl)-4,5,6,7-tetrahydro-benzothiazol-2-yl]-amine A suspension of [3-methoxy-4-(4-methyl-imidazol-1-yl)-phenyl]-thiourea (52 mg, 0.20 mmol) and of crude 6-bromo-2-(4-methyl-3-trifluoromethyl-phenyl)-cyclohexanone (70 mg, 0.21 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (17 mg, 15%) as a pale-brown oil. MS ISP (m/e): 499.0 (100) [(M+H)$^+$]. $^1$H NMR (CDCl$_3$, 300 MHz): δ (ppm)=7.64 (s, 1H), 7.42 (s, 1H), 7.33 (s, 1H), 7.20 (s, 2H), 7.09 (d, 1H), 6.82 (s, 1H), 6.65 (d, 1H), 4.04 (m, 1H), 3.52 (s, 3H), 2.77 (m, 2H), 2.44 (s, 3H), 2.29 (s, 3H), 2.22 (m, 1H), 1.78-2.03 (m, 3H).

Example 10

[3-Methoxy-4-(4-methyl-imidazol-1-yl)-phenyl]-[4-(4-trifluoromethoxy-phenyl)-4,5,6,7-tetrahydro-benzothiazol-2-yl]-amine

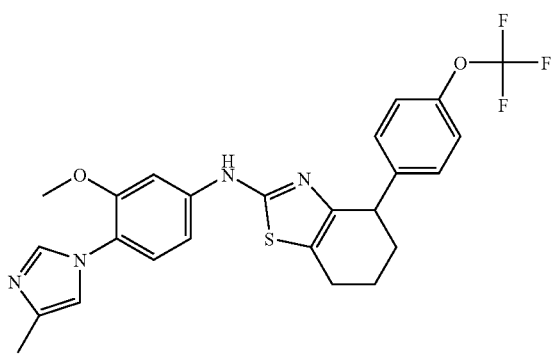

a) 6-Bromo-2-(4-trifluoromethoxyl-phenyl)-cyclohexanone 2-(4-Trifluoromethoxyl-phenyl)-cyclohexanone (53 mg, 0.21 mmol) was dissolved in chloroform (1 mL). To this solution bromine (34.4 mg, 0.22 mmol) in chloroform (0.5 mL) was added drop wise at room temperature. The reaction was stirred for 1½ hours at room temperature. The solvent was removed under reduced pressure to yield the crude title compound (65 mg) which was used directly in the next step without further purification.

b) [3-Methoxy-4-(4-methyl-imidazol-1-yl)-phenyl]-[4-(4-trifluoromethoxy-phenyl)-4,5,6,7-tetrahydro-benzothiazol-2-yl]-amine A suspension of [3-methoxy-4-(4-methyl-imidazol-1-yl)-phenyl]-thiourea (48 mg, 0.18 mmol) and of crude 6-bromo-2-(4-trifluoromethoxyl-phenyl)-cyclohexanone (65 mg, 0.19 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (16 mg, 17%) as a pale-brown oil. MS ISP (m/e): 501.0 (100) [(M+H)$^+$]. $^1$H NMR (CDCl$_3$, 300 MHz): δ (ppm)=7.61 (s, 1H), 7.35 (s, 1H), 7.08-7.20 (m, 4H), 6.82 (s, 1H), 6.65 (d, 1H), 4.06 (m, 1H), 3.56 (s, 3H), 2.75 (m, 2H), 2.28 (s, 3H), 2.25 (m, 1H), 1.77-1.98 (m, 3H).

Example 11

[3-Chloro-4-(4-methyl-imidazol-1-yl)-phenyl]-(4-phenyl-4,5,6,7-tetrahydro-benzothiazol-2-yl)-amine

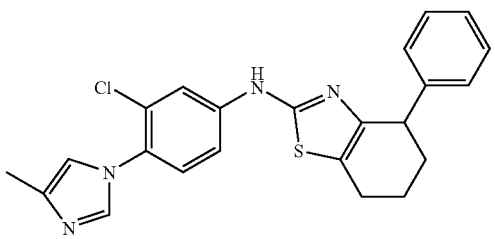

a) 1-(2-Chloro-4-nitro-phenyl)-4-methyl-1H-imidazole

The title compound was prepared from 3,4-dichloronitrobenzene and 4-methylimidazole using in analogous manner the procedure described in example 4a). Chromatography on silica gel using ethyl acetate as eluent gave the title compound as a slightly greenish solid in 64% yield. MS ISP (m/e): 238.0/240.2 (100/40) [(M+H)$^+$].

b) 3-Chloro-4-(4-methyl-imidazol-1-yl)-phenylamine

The compound was prepared from 1-(2-chloro-4-nitro-phenyl)-4-methyl-1H-imidazole and stannous chloride dehydrate using in analogous manner the procedure described in example 4b). The crude compound was obtained as an orange solid in 99% yield and was used without further purification in the next step. MS ISP (m/e): 208.0/210.1 (100/43) [(M+H)$^+$].

c) 3-Chloro-4-(4-methyl-imidazol-1-yl)-phenyl]-thiourea

The compound was prepared from 3-chloro-4-(4-methyl-imidazol-1-yl)-phenylamine and benzylisothiocyanate using in analogous manner the procedure described in example 4c). The crude product was obtained as a yellowish solid in 79% yield and was used without further purification in the next step. MS ISP (m/e): 267.1/269.1 (100/38) [(M+H)$^+$].

d) [3-Chloro-4-(4-methyl-imidazol-1-yl)-phenyl]-(4-phenyl-4,5,6,7-tetrahydro-benzothiazol-2-yl)-amine A suspension of [3-chloro-4-(4-methyl-imidazol-1-yl)-phenyl]-thiourea (66.7 mg, 0.25 mmol) and of 2-bromo-6-phenyl-cyclohexanone (63.3 mg, 0.25 mmol) in ethanol (4 mL) was stirred at room temperature for 30 minutes and then heated for two days to reflux under an atmosphere of nitrogen. After cooling to room temperature the solvent was evaporated under reduced pressure and the residue was purified on silica gel with dichloromethane and then with dichloromethane/methanol (19:1 v/v) as eluent to yield the title compound (50 mg, 48%) as a pale-brown solid. MS ISP (m/e): 421.0/422.2 (100/38) [(M+H)$^+$]. $^1$H NMR (DMSO-D$_6$, 300 MHz): δ (ppm)=10.38 (s, 1H), 8.31 (s, 1H), 7.82 (s, 1H), 7.60 (s, 1H), 7.46-7.10 (m, 7H), 6.98 (s, 1H), 4.03 (m, 1H), 2.72 (m, 2H), 2.13 (s, 3H), 2.11 (m, 1H), 1.70-1.90 (m, 3H).

Example 12

[4-(2,5-Difluoro-phenyl)-4,5,6,7-tetrahydro-benzothiazol-2-yl]-[3-methoxy-4-(4-methyl-imidazol-1-yl)-phenyl]-amine

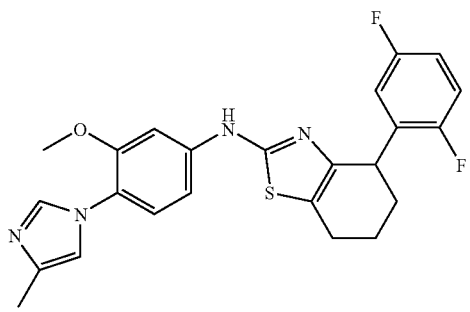

a) 6-Bromo-2-(2,5-difluoro-phenyl)-cyclohexanone 2-(2,5-Difluoro-phenyl)-cyclohexanone (51 mg, 0.24 mmol) was dissolved in chloroform (1 mL). To this solution bromine (40.7 mg, 0.26 mmol) in chloroform (0.5 mL) was added drop wise at room temperature. The reaction was stirred for 1½ hours at room temperature. The solvent was removed under reduced pressure to yield the cude title compound (73 mg) which was used directly in the next step without further purification.

b) [4-(2,5-Difluoro-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (63 mg, 0.24 mmol) and of crude 6-bromo-2-(2,5-difluoro-phenyl)-cyclohexanone (73 mg, 0.25 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (53 mg, 49%) as an off-white solid. MS ISP (m/e): 453.3 (100) [(M+H)$^+$]. $^1$H NMR (CDCl$_3$, 300 MHz): δ (ppm)=7.88 (s, 1H), 7.50 (s, 1H), 7.09 (d, 1H), 6.99 (m, 1H), 6.80-6.88 (m, 2H), 6.75 (d, 1H), 6.67 (m, 1H), 4.35 (m, 1H), 3.59 (s, 3H), 2.76 (m, 2H), 2.37 (s, 3H), 2.22 (m, 1H), 1.70-1.98 (m, 3H).

Example 13

[4-(2,5-Dimethyl-phenyl)-4,5,6,7-tetrahydro-benzothiazol-2-yl]-[3-methoxy-4-(4-methyl-imidazol-1-yl)-phenyl]-amine

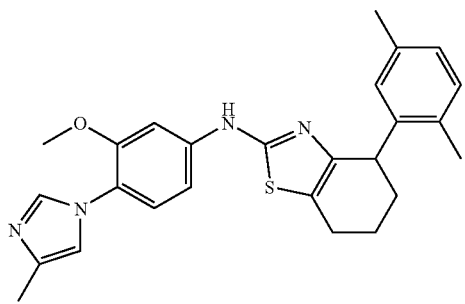

a) 6-Bromo-2-(2,5-dimethyl-phenyl)-cyclohexanone 2-(2,5-Dimethyl-phenyl)-cyclohexanone (51 mg, 0.25 mmol) was dissolved in chloroform (1 mL). To this solution bromine (42.3 mg, 0.27 mmol) in chloroform (0.5 mL) was added drop wise at room temperature. The reaction was stirred for 1½ hours at room temperature. The solvent was removed under reduced pressure to yield the crude title compound (81 mg) which was used directly in the next step without further purification.

b) [4-(2,5-Dimethyl-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (72 mg, 0.27 mmol) and of crude 6-bromo-2-(2,5-dimethyl-phenyl)-cyclohexanone (81 mg, 0.29 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (11 mg, 9%) as an off-white solid. MS ISP (m/e): 445.3 (100) [(M+H)$^+$]. $^1$H NMR (CDCl$_3$, 300 MHz): δ (ppm)=7.60 (s, 1H), 7.35 (s, 1H), 7.09 (d, 1H), 7.03 (d, 1H), 2.34 (s, (d, 1H), 6.82 (s, 1H), 6.69 (s, 1H), 6.62 (d, 1H), 4.21 (m, 1H), 3.53 (s, 3H), 2.78 (m, 2H), 2.34 (s, 3H), 2.28 (s, 3H), 2.23 (s, 3H), 2.15 (m, 1H), 1.75-2.05 (m, 3H).

Example 14

[4-(2-Chloro-phenyl)-4,5,6,7-tetrahydro-benzothiazol-2-yl]-[3-methoxy-4-(4-methyl-imidazol-1-yl)-phenyl]-amine

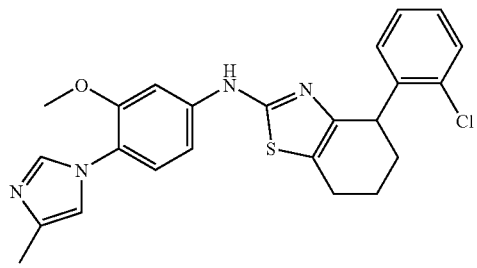

a) 6-Bromo-2-(2-chloro-phenyl)-cyclohexanone 2-(2-Chloro-phenyl)-cyclohexanone (51 mg, 0.25 mmol) was dissolved in chloroform (1 mL). To this solution bromine (42.3 mg, 0.27 mmol) in chloroform (0.5 mL) was added drop wise at room temperature. The reaction was stirred for 1½ hours at room temperature. The solvent was removed under reduced pressure to yield the crude title compound (81 mg) which was used directly in the next step without further purification.

b) [4-(2-Chloro-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (69 mg, 0.26 mmol) and of crude 6-bromo- 2-(2-chloro-phenyl)-cyclohexanone (79 mg, 0.28 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (55 mg, 46%) as an off-white solid. $^1$H NMR (CDCl$_3$, 300 MHz): δ (ppm)=7.77 (s, 1H), 7.46 (s, 1H), 7.35 (m, 1H), 7.13 (m, 2H), 7.08 (d, 1H), 6.96 (m, 1H), 6.85 (s, 1H), 6.68 (d, 1H), 4.53 (m, 1H), 3.54 (s, 3H), 2.77 (m, 2H), 2.33 (s, 3H), 2.24 (m, 1H), 1.80-1.99 (m, 3H).

Example 15

[4-(3-fluoro-4-methyl-phenyl)-4,5,6]-tetrahydro-benzothiazol-2-yl]-[3-methoxy-4-(4-methyl-imidazol-1-yl)-phenyl]-amine

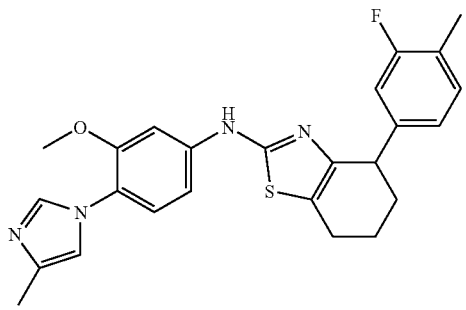

a) 6-Bromo-2-(3-fluoro-4-methyl-phenyl)-cyclohexanone 2 (3 fluoro-4-methyl-phenyl)-cyclohexanone (51 mg, 0.25 mmol) was dissolved in chloroform (1 mL). To this solution bromine (41.5 mg, 0.27 mmol) in chloroform (0.5 mL) was added drop wise at room temperature. The reaction was stirred for 1½ hours at room temperature. The solvent was removed under reduced pressure to yield the title compound (74 mg) which was used directly in the next step without further purification.

b) [4-(3-fluoro-4-methyl-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)phenyl]-thiourea (65 mg, 0.25 mmol) and of crude 6-bromo-2-(3-fluoro-4-methyl-phenyl)-cyclohexanone (74 mg, 0.26 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (9 mg, 8%) as an off-white solid. MS ISP (m/e): 449.2 (100) [(M+H)$^+$]. $^1$H NMR (CDCl$_3$, 300 MHz): (ppm)=7.66 (s, 1H), 7.36 (s, 1H), 7.09 (t, 2H), 6.83-6.88 (m, 2H), 6.79 (d, 1H), 6.64 (d, 1H), 3.99 (m, 1H), 3.58 (s, 3H), 2.75 (m, 2H), 2.30 (s, 3H), 2.22 (s, 3H), 2.20-2.35 (m, 1H), 1.78-2.05 (m, 3H).

Example 16

[4-(4-Chloro-3-trifluoromethyl-phenyl)-4,5,6,7-tetrahydro-benzothiazol-2-yl]-[3-methoxy-4-(4-methyl-imidazol-1-yl)-phenyl]-amine

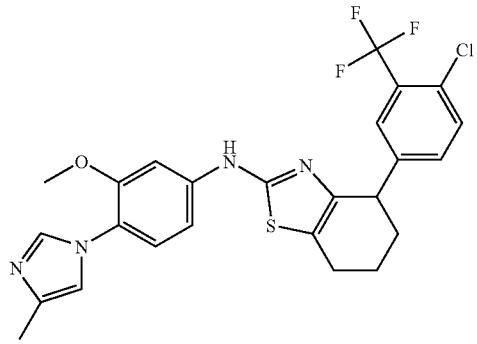

a) 6-Bromo-2-(4-chloro-3-trifluoromethyl-phenyl)-cyclohexanone 2-(4-Chloro-3-trifluoromethyl-phenyl)-cyclohexanone (50 mg, 0.18 mmol) was dissolved in chloroform (1 mL). To this solution bromine (30.3 mg, 0.19 mmol) in chloroform (0.5 mL) was added drop wise at room temperature. The reaction was stirred for 1½ hours at room temperature. The solvent was removed under reduced pressure to yield the crude title compound (53 mg) which was used directly in the next step without further purification.

b) [4-(4-Chloro-3-trifluoromethyl-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (39 mg, 0.15 mmol) and of crude 6-bromo-2-(4-chloro-3-trifluoromethyl-phenyl)-cyclohexanone (53 mg, 0.16 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (22 mg, 29%) as a yellow gum. MS ISP (m/e): 518.8/520.9 (100/36) [(M+H)$^+$]. $^1$H NMR (CDCl$_3$, 300 MHz): δ (ppm)=7.62 (s, 1H), 7.56 (s, 1H), 7.41 (d, 2H), 7.30 (s, 1H), 7.10 (d, 1H), 6.83-6.89 (m, 2H), 6.67 (d, 1H), 4.05 (m, 1H), 3.55 (s, 3H), 2.75 (m, 2H), 2.29 (s, 3H), 2.22 (m, 1H), 1.78-2.05 (m, 3H).

Example 17

[4-(4-Chloro-phenyl)-4,5,6,7-tetrahydro-benzothiazol-2-yl]-[3-methoxy-4-(4-methyl-imidazol-1-yl)-phenyl]-amine

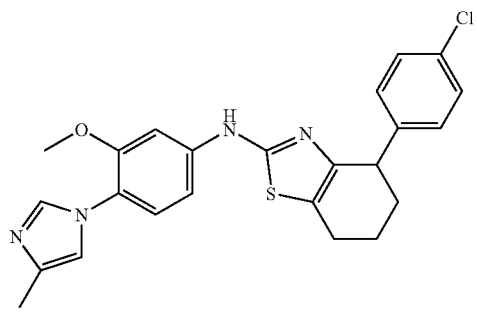

a) 6-Bromo-2-(4-chloro-phenyl)-cyclohexanone 2-(4-Chloro-phenyl)-cyclohexanone (51 mg, 0.24 mmol) was dissolved in chloroform (1 mL). To this solution bromine (41.0 mg, 0.26 mmol) in chloroform (0.5 mL) was added drop wise at room temperature. The reaction was stirred for 1½ hours at room temperature. The solvent was removed under reduced pressure to yield the crude title compound (74 mg) which was used directly in the next step without further purification.

b) [4-(4-Chloro-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (50 mg, 0.19 mmol) and of crude 6-bromo-2-(4-chloro-phenyl)-cyclohexanone (74 mg, 0.26 mmol) in ethanol (2 mL) was heated to reflux under an atmosphere of nitrogen for 2 days. After cooling to room temperature the solvent was evaporated under reduced pressure and the residue was purified by column chromatography on silica gel using dichloromethane/methanol (19:1 v/v) as eluent to yield the title compound (16 mg, 19%) as a brown gum. $^1$H NMR (DMSO-D$_6$, 300 MHz): δ (ppm)=10.37 (s, 1H), 7.79 (s, 1H), 7.68 (d, 1H), 7.66 (s, 2H), 7.50 (d, 1H), 7.26 (d, 1H), 7.17 (d, 1H), 7.03 (s, 1H), 3.80 (m, 1H), 3.80 (s, 3H), 2.87 (m, 2H), 2.18 (m, 2H), 2.14 (s, 3H), 1.90 (m, 2H).

Example 18

[4-(4-Methyl-imidazol-1-yl)-phenyl]-(4-phenyl-4,5,6,7-tetrahydro-benzothiazol-2-yl)-amine

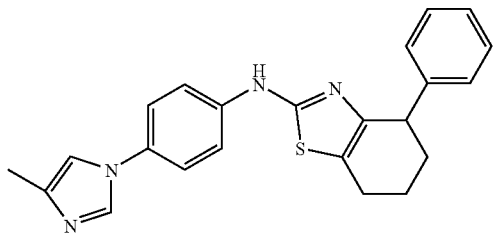

a) [4-(4-Methyl-imidazol-1-yl)-phenyl]-thiourea

The compound was prepared from 4-(4-methyl-imidazol-1-yl)-phenylamine (1000 mg, 5.8 mmol) and benzoylisocyanate (989 mg, 6.1 mmol) using in analogous manner the procedure described in example 6d) to yield the title compound as a pale-brown solid (1270 mg, 95%). MS ISP (m/e): 216.1 (100) [(M−NH$_3$+H)$^+$], 232.7 (70) [(M+H)$^+$].

b) [4-(4-Methyl-imidazol-1-yl)-phenyl]-(4-phenyl-4,5,6,7-tetrahydro-benzothiazol-2-yl)-amine A suspension of [4-(4-methyl-imidazol-1-yl)-phenyl]-thiourea (29.2 mg, 0.13 mmol) and of 2-bromo-6-phenyl-cyclohexanone (65.5 mg, 0.26 mmol) in ethanol (2 mL) was stirred at room temperature for 30 minutes and then heated for two days to reflux under an atmosphere of nitrogen. After cooling to room temperature the solvent was evaporated under reduced pressure and the residue was purified on silica gel using dichloromethane then dichloromethane/methanol (19:1 v/v) as eluent to yield the title compound (50 mg, 100%) as an colourless oil. MS ISP (m/e): 387.4 (100) [(M+H)$^+$]. $^1$H NMR (DMSO-D$_6$, 300 MHz): δ (ppm)=10.12 (s, 1H), 7.95 (s, 1H), 7.52 (d, 2H), 7.39 (d, 2H), 7.29 (m, 3H), 7.11-7.20 (m, 3H), 4.02 (m, 1H), 2.71 (m, 2H), 2.13 (s, 3H), 2.12 (m, 1H), 1.70-1.94 (m, 3H).

Example 19

{4-(4-Chloro-phenyl)-2-[3-methoxy-4-(4-methyl-imidazol-1-yl)-phenylamino]-4,5,6,7-tetrahydro-benzothiazol-4-yl}-acetonitrile

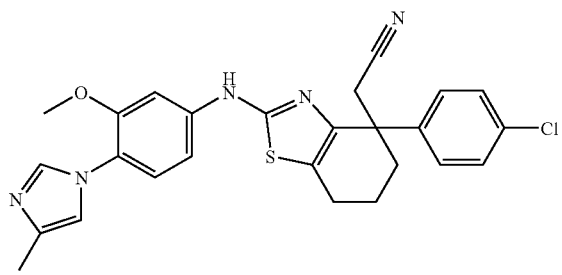

a) [3-Bromo-1-(4-chloro-phenyl)-2-oxo-cyclohexyl]-acetonitrile 1-(4-Chloro-phenyl)-2-oxo-cyclohexyl-acetonitrile (100 mg, 0.40 mmol) was dissolved in chloroform (1 mL). To this solution bromine (67.7 mg, 0.42 mmol) in chloroform (0.5 mL) was added drop wise at −11° C. The reaction was stirred for 1½ hours at 5° C., then for 1 hours t room temperature and finally for 1 hour at 50° C. The solvent was removed under reduced pressure and the residue was purified by column chromatography on silica gel using dichloromethane as eluent to yield the title compound (104 mg, 79%) as colourless oil. NMR (CDCl$_3$, 300 MHz): δ (ppm)=7.44 (d, 2H), 7.13 (d, 2H), 4.62 (dd, 1H), 2.99 (m, 2.80 (s, 2H), 2.58 (m, 1H), 2.14 (m, 1H), 1.92 (m, 3H).

b) {4-(4-Chloro-phenyl)-2-[3-methoxy-4-(4-methyl-imidazol-1-yl)-phenylamino]-4,5,6,7-tetrahydro-benzothiazol-4-yl}-acetonitrile A suspension of [3-methoxy-4-(4-methyl-imidazol-1-yl)-phenyl]-thiourea (40.2 mg, 0.15 mmol) and of [3-bromo-1-(4-chloro-phenyl)-2-oxo-cyclohexyl]-acetonitrile (50.0 mg, 0.15 mmol) in ethanol (2 mL) was heated to reflux under an atmosphere of nitrogen for 2 days. After cooling to room temperature the solvent was evaporated under reduced pressure and the residue was purified by column chromatography on silica gel using dichloromethane/methanol/concentrated aqueous NH4OH solution (9:1:0.1 v/v/v) as eluent to yield the title compound (74 mg, 99%) as a yellow gum. $^1$H NMR (CDCl$_3$, 300 MHz): δ (ppm)=7.62 (s, 1H), 7.56 (s, 1H), 7.37 (s, 1H), 7.28 (d, 2H), 7.16 (d, 2H), 6.89 (s, 1H), 3.76 (s, 3H), 3.19 (d, 1H), 3.03 (d, 1H), 2.72 (m, 2H), 2.30 (s, 3H), 2.19 (m, 1H), 1.89 (m, 2H), 1.60 (m, 1H).

Example 20

5-[4-(4-Chloro-phenyl)-4-cyanomethyl-4,5,6,7-tetrahydro-benzothiazol-2-ylamino]-2-(4-methyl-imidazol-1-yl)-benzonitrile

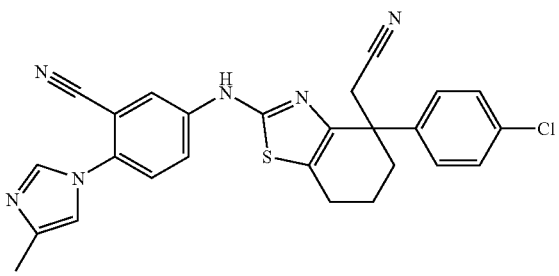

a) 2-(4-Methyl-imidazol-1-yl)-5-nitro-benzonitrile

A suspension of 3-cyano-4-fluoronitrobenzene (831 mg, 5 mmol), of 4-methylimidazol (821 mg, 10 mmol) and of potassium carbonate (1382 mg, 10 mmol) in acetonitrile (10 mL) was stirred over the weekend at room temperature. The solvent was evaporated and the residue was partitioned between ethyl acetate and 1N aqueous NaOH solution. The aqueous layer was extracted with ethyl acetate. The combined organic layers were washed with brine, dried over sodium sulfate, filtered and the solvent was evaporated under reduced pressure. The crude product was crystallized from ethanol/water to yield the title compound (650 mg, 57%) as an off-white solid. $^1$H NMR (DMSO-D$_6$, 300 MHz): δ (ppm)=8.95 (s, 1H), 8.62 (d, 1H), 8.16 (s, 1H), 7.93 (d, 1H), 7.49 (s, 1H), 2.21 (s, 3H).

b) 5-Amino-2-(4-methyl-imidazol-1-yl)-benzonitrile 2-(4-Methyl-imidazol-1-yl)-5-nitro-benzonitrile (650 mg, 2.84 mmol) dissolved in ethyl acetate (10 mL) was hydrogenated under an atmosphere of hydrogen at room temperature for 5 hours in the presence of 10% palladium on charcoal (150 mg). The catalyst was filtered off and washed with ethyl acetate. The solvent of the filtrate was evaporated under reduced pressure and dried to yield the title compound (450 mg, 80%) as a yellow solid. MS ISP (m/e): 199.1 (100) [(M+H)$^+$]. $^1$H NMR (DMSO-D$_6$, 300 MHz): δ (ppm)=7.72 (s, 1H), 7.23 (d, 1H), 7.10 (s, 1H), 6.96 (s, 1H), 6.91 (d, 1H), 2.15 (s, 3H).

c) [3-Cyano-4-(4-methyl-imidazol-1-yl)-phenyl]-thiourea

To a solution of 5-amino-2-(4-methyl-imidazol-1-yl)-benzonitrile (450 mg, 2.27 mmol) in tetrahydrofuran (22 mL) benzoylisocyanate (407 mg, 2.5 mmol) was added and the reaction was stirred at room temperature for 2 hours. The solvent was evaporated under reduce pressure and the residue was suspended in methanol (22 mL). A solution of potassium carbonate (941 mg, 6.8 mmol) in water (16.5 mL) was added drop wise to the suspension. The reaction was stirred at room temperature over night to yield a solution, which was concentrated under reduced pressure. The residue was suspended in water, filtered, washed with water and diethyl ether. The solid was several times suspended in tetrahydrofuran; the solvent was evaporated under reduced pressure and dried under vacuum to yield the title compound (480 mg, 82%) as a pale-yellow solid. MS ISP (m/e): 241.1 (100) [(M–NH$_3$+H)$^+$], 258.0 (85) [(M+H)$^+$]. $^1$H NMR (DMSO-D$_6$, 300 MHz): δ (ppm)=10.24 (br s, 1H), 8.22 (s, 1H), 7.92 (s, 1H), 7.87 (d, 1H), 7.57 (d, 1H), 7.28 (s, 1H), 2.18 (s, 3H).

d) 5-[4-(4-Chloro-phenyl)-4-cyanomethyl-4,5,6,7-tetrahydro-benzothiazol-2-ylamino]-2-(4-methyl-imidazol-1-yl)-benzonitrile A suspension of [3-cyano-4-(4-methyl-imidazol-1-yl)-phenyl]-thiourea (39.4 mg, 0.15 mmol) and of [3-bromo-1-(4-chloro-phenyl)-2-oxo-cyclohexyl]-acetonitrile (50.0 mg, 0.15 mmol) in ethanol (2 mL) was heated to reflux under an atmosphere of nitrogen for 2 days. After cooling to room temperature the solvent was evaporated under reduced pressure and the residue was purified by column chromatography on silica gel using dichloromethane/methanol/concentrated aqueous NH4OH solution (9:1:0.1 v/v/v) as eluent to yield the title compound (34 mg, 46%) as a yellow gum. $^1$H NMR (CDCl$_3$, 300 MHz): δ (ppm)=8.41 (s, 1H), 7.95 (s, 1H), 7.89 (d, 1H), 7.69 (s, 1H), 7.31 (t, 2H), 7.12 (d, 2H), 7.00 (d, 1H), 3.23 (d, 1H), 3.02 (d, 1H), 2.73 (m, 2H), 2.31 (s, 3H), 2.17 (m, 1H), 1.88 (m, 2H), 1.60 (m, 1H).

Example 21

2-(4-Methyl-imidazol-1-yl)-5-(4-phenyl-4,5,6,7-tetrahydro-benzothiazol-2-ylamino)-benzonitrile

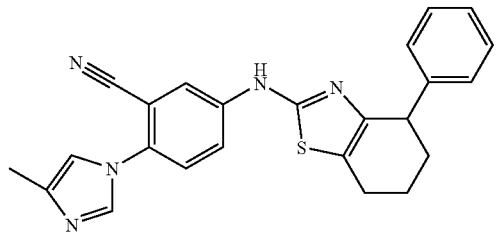

A suspension of [3-cyano-4-(4-methyl-imidazol-1-yl)-phenyl]-thiourea (64.3 mg, 0.25 mmol) and of 2-bromo-6-phenyl-cyclohexanone (63.3 mg, 0.25 mmol) in ethanol (2 mL) was heated to reflux under an atmosphere of nitrogen for 2 days. After cooling to room temperature the solvent was evaporated under reduced pressure. The residue was suspended in dichloromethane/diethyl ether. The precipitated solid was filtered off, washed with diethyl ether and dried under reduced pressure to yield the title compound (90 mg, 88%) as a pale-brown solid. MS ISP (m/e): 412.2 (100) [(M+H)$^+$]. $^1$H NMR (DMSO-D$_6$, 300 MHz): δ (ppm)=10.75 (s, 1H), 9.31 (s, 1H), 8.16 (s, 1H), 7.78 (m, 2H), 7.65 (d, 1H), 7.30 (t, 2H), 7.17 (m, 3H), 4.08 (m, 1H), 2.75 (m, 2H), 2.34 (s, 3H), 2.15 m, 2H), 1.76 (m, 2H).

Example 22

2-[3-Methoxy-4-(4-methyl-imidazol-1-yl)-phenylamino]-4,5,6,7-tetrahydro-benzothiazole-4-carboxylic acid ethyl ester

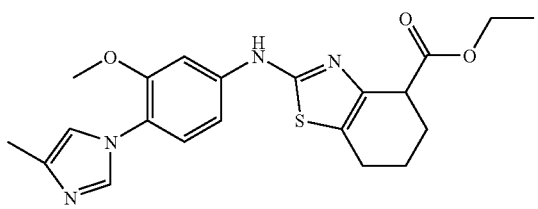

a) 2-Bromo-6-(carbethoxy)-cyclohexanone

2-Carbethoxy-cyclohexanone (5.0 g, 29.4 mmol) was dissolved in diethyl ether (30 mL). To this solution bromine (4.93 g, 30.8 mmol) was added drop wise at room temperature. The reaction was stirred for 1 hour at room temperature, quenched with water and the layers were separated. The organic layer was washed with aqueous thiosulfate solution and brine, dried over sodium sulfate and filtered. The solvent was removed under reduced pressure to yield the crude title compound (7.48 g, 100%) which was used directly in the next step without further purification. $^1$H NMR (CDCl$_3$, 300 MHz): δ (ppm)=4.94 (t, 1H), 4.20 (q, 1H), 2.37 (dt, 1H), 2.25 (m, 1H), 2.09 (m, 2H), 1.74 (m, 2H), 1.24 (t, 3H).

b) 2-[3-Methoxy-4-(4-methyl-imidazol-1-yl)-phenylamino]-4,5,6,7-tetrahydro-benzothiazole-4-carboxylic acid ethyl ester A suspension of [3-methoxy-4-(4-methyl-imidazol-1-yl)-phenyl]-thiourea (131 mg, 0.50 mmol) and of 2-bromo-6-(carbethoxy)-cyclohexanone (137 mg, 0.55 mmol) in ethanol (5 mL) was stirred at room temperature for 2 days and then heated to reflux under an atmosphere of nitrogen over night. After cooling to room temperature the solvent was evaporated under reduced pressure and the residue was purified by column chromatography on silica gel using dichloromethane/methanol (19:1 v/v) as eluent to yield the title compound (180 mg, 87%) as a white solid. MS ISP (m/e): 413.3 (100) [(M+H)$^+$]. $^1$H NMR (DMSO-D$_6$, 300 MHz): δ (ppm)=10.28 (s, 1H), 7.66 (d, 1H), 7.64 (s, 1H), 7.21 (d, 1H), 7.11 (d, 1H), 7.01 (s, 1H), 4.10 (q, 2H), 3.76 (s, 3H), 3.66 (m, 1H), 2.62 (m, 2H), 2.14 (s, 3H), 1.68-2.09 (m, 4H), 1.19 (t, 3H).

Example 23

[5-Benzyl-7-(2-chloro-phenyl)-4,5,6,7-tetrahydro-thiazolo[5,4-c]pyridin-2-yl]-[3-(4-methyl-imidazol-1-yl)-phenyl]-amine

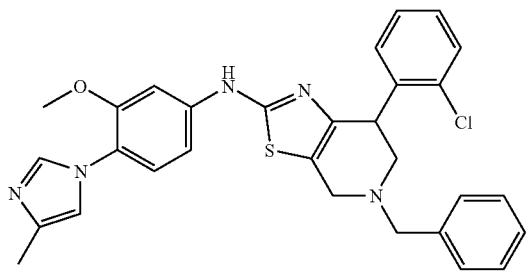

a) 5-Bromo-1-benzyl-3-(2-chloro-phenyl)-piperidin-4-one hydrobromide

Benzyl-3-(2-chloro-phenyl)-piperidin-4-one (100 mg, 0.33 mmol) was dissolved in chloroform (1 mL). To this solution bromine (66 mg, 0.35 mmol) in chloroform (0.5 mL) was added drop wise at −11° C. The reaction was stirred for 1½ hours at 5° C., for 1 hour at room temperature and for 1 hours at 50° C. The solvent was removed under reduced pressure to yield the crude title compound (163 mg) which was used directly in the next step without further purification.

b) [5-Benzyl-7-(2-chloro-phenyl)-4,5,6,7-tetrahydro-thiazolo[5,4-c]pyridin-2-yl]-[3-methoxy-4-(4-methyl-imidazol-1-yl)-phenyl]-amine A suspension of [3-methoxy-4-(4-methyl-imidazol-1-yl)-phenyl]-thiourea (100 mg, 0.38 mmol) and of crude 6-bromo-2-(2-chloro-phenyl)-cyclohexanone hydrobromide (163 mg, 0.36 mmol) in ethanol (5 mL) was heated to reflux under an atmosphere of nitrogen for 2 days. N,N-diisopropyl ethyl amine (49 mg, 0.38 mmol) was added and the reaction was heated to reflux over night. After cooling to room temperature the solvent was evaporated under reduced pressure and the residue was treated with dichloromethane/methanol/concentrated aqueous NH4OH solution (9:1:0.1 v/v/v). The precipitate was filtered off and the filtrate was concentrated under reduced pressure. The residue was purified by reversed preparative HPLC using acetonitril/water (0.1% formic acid) to yield the title compound (6 mg, 3%) as a yellow solid. MS ISP (m/e): 541.9/543.9 (100/35) [(M+H)$^+$]. $^1$H NMR (CDCl$_3$, 300 MHz): δ (ppm)=7.60 (s, 1H), 7.37 (m, 2H), 7.26 (m, 5H), 7.09-7.18 (m, 4H), 6.82 (s, 1H), 6.66 (d, 1H), 4.70 (m, 1H), 3.74 (m, 3H), 3.60 (s, 3H), 3.19 (dd, 1H), 2.81 (dd, 1H), 2.28 (s, 2H).

Example 24

[5-Benzyl-7-(4-chloro-3-fluorophenyl)-4,5,6,7-tetrahydro-thiazolo[5,4-c]pyridin-2-yl]-[3-methoxy-4-(4-methyl-imidazol-1-yl)-phenyl]-amine

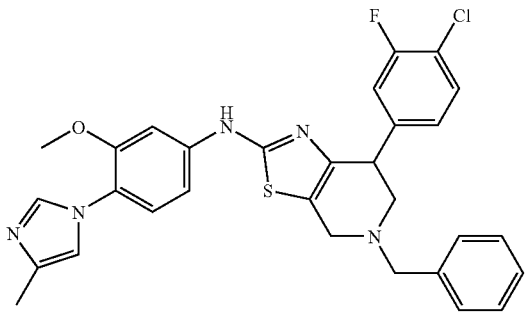

a) 5-Bromo-1-benzyl-3-(4-chloro-3-fluorophenyl)-piperidin-4-one hydrobromide Benzyl-3-(4-chloro-3-fluorophenyl)-piperidin-4-one (100 mg, 0.33 mmol) was dissolved in chloroform (1 mL). To this solution bromine (53 mg, 0.33 mmol) in chloroform (0.5 mL) was added drop wise at −11° C. The reaction was stirred for 1½ hours at 5° C., for 1 hour at room temperature and for 1 hours at 50° C. The solvent was removed under reduced pressure to yield the crude title compound (147 mg) which was used directly in the next step without further purification.

b) [5-Benzyl-7-(4-chloro-3-fluorophenyl)-4,5,6,7-tetrahydro-thiazolo[5,4-c]pyridin-2-yl]-[methoxy-4-(4-methyl-imidazol-1-yl)-phenyl]-amine A suspension of [3-methoxy-4-(4-methyl-imidazol-1-yl)-phenyl]-thiourea (100 mg, 0.38 mmol) and of crude 6-bromo-2-(4-chloro-3-fluorophenyl)-cyclohexanone hydrobromide (147 mg, 0.31 mmol) in ethanol (5 mL) was heated to reflux under an atmosphere of nitrogen for 2 days. N,N-diisopropyl ethyl amine (49 mg, 0.38 mmol) was added and the reaction was heated to reflux over night. After cooling to room temperature the solvent was evaporated under reduced pressure and the residue was treated with dichloromethane/methanol/concentrated aqueous NH4OH solution (9:1:0.1 v/v/v). The precipitate was filtered off and the filtrate was concentrated under reduced pressure. The residue was purified by reversed preparative HPLC using acetonitril/water (0.1% formic acid) to yield the title compound (12 mg, 6%) as a yellow solid. MS ISP (m/e): 559.8/561.8 (100/45) [(M+H)$^+$]. $^1$H NMR (CDCl$_3$, 300 MHz): δ (ppm)=7.70 (s, 1H), 7.29 (m, 7H), 7.12 (s, 1H), 7.09 (s, 1H), 7.03 (d, 1H), 6.82 (s, 1H), 6.72 (d, 1H), 4.08 (m, 1H), 3.73 (m, 3H), 3.66 (s, 1H), 3.58 (d, 1H), 3.12 (dd, 1H), 2.73 (dd, 1H), 2.29 (s, 3H).

Example 25

[4-(2,4-Dichloro-phenyl)-4,5,6,7-tetrahydro-benzothiazol-2-yl]-[3-methoxy-4-(4-methyl-imidazol-1-yl)-phenyl]-amine

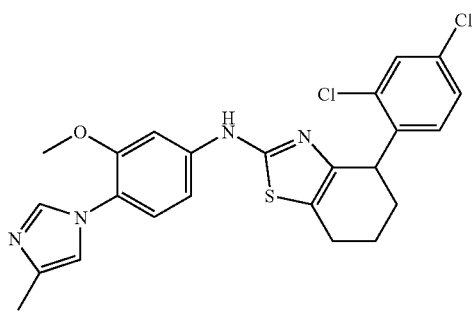

a) 2-Bromo-6-(2,4-dichloro-phenyl)-cyclohexanone 2-(2,4-Dichloro-phenyl)-cyclohexanone (50 mg, 0.21 mmol) was dissolved in chloroform (1 mL). To this solution bromine (34.5 mg, 0.22 mmol) in chloroform (0.5 mL) was added drop wise at room temperature. The reaction was stirred for 1½ hours at room temperature. The solvent was removed under reduced pressure to yield the crude title compound (79 mg) which was used directly in the next step without further purification.

b) [4-(2,4-Dichloro-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (62 mg, 0.24 mmol) and of crude 2-bromo-6-(2,4-dichloro-phenyl)-cyclohexanone (79 mg, 0.25 mmol) in ethanol (2 mL) was heated to reflux under an atmosphere of nitrogen for 3 days. After cooling to room temperature the solvent was evaporated under reduced pressure and the residue was purified by reversed preparative HPLC using acetonitril/water (0.1% formic acid) to yield the title compound (43 mg, 37%) as an off-white solid. MS ISP (m/e): 485.3/487.3 (100/73) [(M+H)$^+$]. $^1$H NMR (CDCl$_3$, 300 MHz): δ (ppm)=8.00 (s, 1H), 7.47 (s, 1H), 7.39 (s, 1H), 7.11 (m, 2H), 6.89 (m, 2H), 6.75 (d, 1H), 4.47 (m, 1H), 3.60 (s, 3H), 2.76 m, 2H), 2.38 (s, 3H), 2.22 (m, 1H), 1.86 (m, 3H).

Example 26

[4-(2,5-Dichloro-phenyl)-4,5,6,7-tetrahydro-benzothiazol-2-yl]-[3-methoxy-4-(4-methyl-imidazol-1-yl)-phenyl]-amine

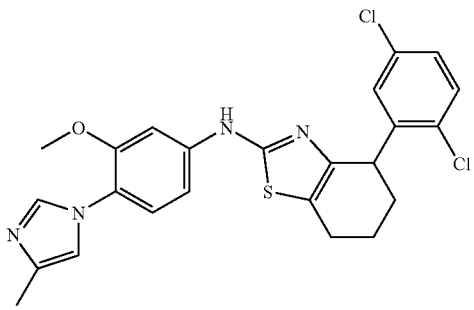

a) 2-Bromo-6-(2,5-dichloro-phenyl)-cyclohexanone 2-(2,5-Dichloro-phenyl)-cyclohexanone (50 mg, 0.21 mmol) was dissolved in chloroform (1 mL). To this solution bromine (34.5 mg, 0.22 mmol) in chloroform (0.5 mL) was added drop wise at room temperature. The reaction was stirred for 1½ hours at room temperature. The solvent was removed under reduced pressure to yield the crude title compound (78 mg) which was used directly in the next step without further purification.

b) [4-(2,5-Dichloro-phenyl)-4,5,6,7-tetrahydro-benzothiazol-2-yl]-[3-methoxy-4-(4-methyl-imidazol-1-yl)-phenyl]-amine A suspension of 3-methoxy-4-(4-methyl-imidazol-1-yl)-phenyl]-thiourea (61 mg, 0.23 mmol) [and of crude 2-bromo-6-(2,5-dichloro-phenyl)-cyclohexanone (78 mg, 0.24 mmol) in ethanol (2 mL) was heated to reflux under an atmosphere of nitrogen for 3 days. After cooling to room temperature the solvent was evaporated under reduced pressure and the residue was purified by reversed preparative HPLC using acetonitril/water (0.1% formic acid) to yield the title compound (55 mg, 49%) as an off-white solid. MS ISP (m/e): 485.3/487.3 (100/72) [(M+H)$^+$]. $^1$H NMR (CDCl$_3$, 300 MHz): δ (ppm)=7.73 (s, 1H), 7.38 (s, 1H), 7.28 (d, 1H), 7.12 (d, 2H), 6.93 (s, 1H), 6.85 (s, 1H), 6.72 (d, 1H), 4.48 (m, 1H), 3.62 (s, 3H), 2.76 m, 2H), 2.32 (s, 3H), 2.23 (m, 1H), 1.86 (m, 3H).

Example 27

[4-(3,5-Dichloro-phenyl)-4,5,6,7-tetrahydro-benzothiazol-2-yl]-[3-methoxy-4-(4-methyl-imidazol-1-yl)-phenyl]-amine

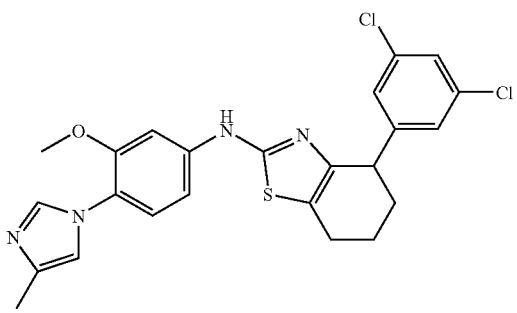

a) 2-Bromo-6-(3,5-dichloro-phenyl)-cyclohexanone 2-(3,5-Dichloro-phenyl)-cyclohexanone (50 mg, 0.21 mmol) was dissolved in chloroform (1 mL). To this solution bromine (34.5 mg, 0.22 mmol) in chloroform (0.5 mL) was added drop wise at room temperature. The reaction was stirred for 1½ hours at room temperature. The solvent was removed under reduced pressure to yield the crude title compound (75 mg) which was used directly in the next step without further purification.

b) [4-(3,5-Dichloro-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (58 mg, 0.22 mmol) and of crude 2-bromo-6-(3,5-dichloro-phenyl)-cyclohexanone (75 mg, 0.23 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (30 mg, 28%) as a yellow solid. MS ISP (m/e): 485.3/487.3 (100/72) [(M+H)$^+$]. $^1$H NMR (CDCl$_3$, 300 MHz): δ (ppm)=7.64 (s, 1H), 7.35 (s, 1H), 7.20 (s, 1H), 7.11 (d, 1H), 7.04 (s, 2H), 6.84 (s, 1H), 6.69 (d, 1H), 3.98 (m, 1H), 3.63 (s, 3H), 2.75 (m, 2H), 2.30 (s, 3H), 2.22 (m, 1H), 1.83 (m, 3H).

Example 28

[4-(3,5-Difluoro-phenyl)-4,5,6,7-tetrahydro-benzothiazol-2-yl]-[3-methoxy-4-(4-methyl-imidazol-1-yl)-phenyl]-amine

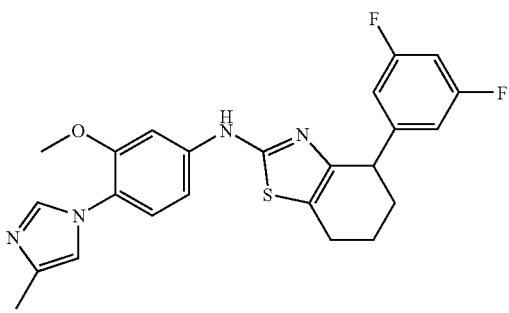

a) 2-Bromo-6-(3,5-difluoro-phenyl)-cyclohexanone 2-(3,5-Difluoro-phenyl)-cyclohexanone (50 mg, 0.24 mmol) was dissolved in chloroform (1 mL). To this solution bromine (39.9 mg, 0.25 mmol) in chloroform (0.5 mL) was added drop wise at room temperature. The reaction was stirred for 1½ hours at room temperature. The solvent was removed under reduced pressure to yield the crude title compound (78 mg) which was used directly in the next step without further purification.

b) [4-(3,5-Difluoro-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (68 mg, 0.26 mmol) and of crude 2-bromo-6-(3,5-difluoro-phenyl)-cyclohexanone (78 mg, 0.27 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (40 mg, 34%) as a yellow solid. $^1$H NMR (CDCl$_3$, 300 MHz): δ (ppm)=7.70 (s, 1H), 7.41 (s, 1H), 7.10 (d, 1H), 6.85 (s, 1H), 6.67-6.73 (m, 4H), 4.03 (m, 1H), 3.62 (s, 3H), 2.75 (m, 2H), 2.31 (s, 3H), 2.22 (m, 1H), 1.84 (m, 3H).

Example 29

[4-(3,5-Trifluoromethyl-phenyl)-4,5,6,7-tetrahydro-benzothiazol-2-yl]-[3-methoxy-4-(4-methyl-imidazol-1-yl)-phenyl]-amine

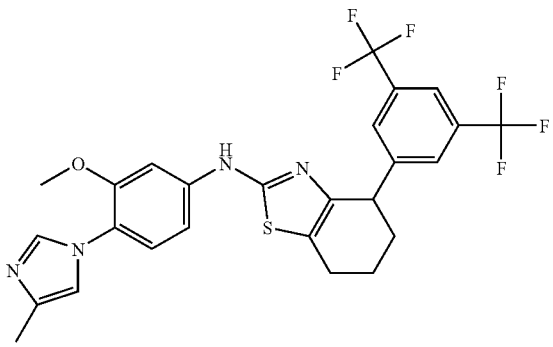

a) 2-Bromo-6-(3,5-trifluoromethyl-phenyl)-cyclohexanone 2-(3,5-Trifluoromethyl-phenyl)-cyclohexanone (51 mg, 0.16 mmol) was dissolved in chloroform (1 mL). To this solution bromine (27.6 mg, 0.17 mmol) in chloroform (0.5 mL) was added drop wise at room temperature. The reaction was stirred for 1½ hours at room temperature. The solvent was removed under reduced pressure to yield the crude title compound (66 mg) which was used directly in the next step without further purification.

b) [4-(3,5-Trifluoromethyl-phenyl)-4,5,6,7-tetrahydro-benzothiazol-2-yl]-[3-methoxy-4-(4-methyl-imidazol-1-yl)-phenyl]-amine A suspension of [3-methoxy-4-(4-methyl-imidazol-1-yl)-phenyl]-thiourea (42 mg, 0.16 mmol) and of crude 2-bromo-6-(3,5-trifluoromethyl-phenyl)-cyclohexanone (66 mg, 0.17 mmol) in ethanol (2 mL) was heated to reflux under an atmosphere of nitrogen for 2 days. After cooling to room temperature the solvent was evaporated under reduced pressure and the residue was purified by reversed preparative HPLC using acetonitril/water (0.1% formic acid) to yield the title compound (40 mg, 45%) as a yellow solid. MS ISP (m/e): 553.3 (100) [(M+H)$^+$]. $^1$H NMR (CDCl$_3$, 300 MHz): δ (ppm)=7.73 (s, 1H), 7.61 (m, 3H), 7.25 (s, 1H), 7.11 (d, 1H), 6.83 (s, 1H), 6.71 (d, 1H), 4.18 (m, 1H), 3.53 (s, 3H), 2.81 (m, 2H), 2.28 (s, 3H), 2.28 (m, 1H), 1.85 (m, 3H).

Example 30

[3-Methoxy-4-(4-methyl-imidazol-1-yl)-phenyl]-(4-methyl-4-phenyl-4,5,6,7-tetrahydro-benzothiazol-2-yl)-amine

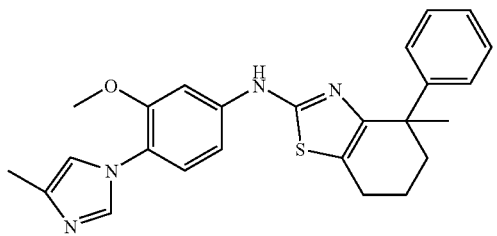

a) 6-Bromo-2-methyl-2-phenyl-cyclohexanone

A solution of 2-methyl-2-phenyl-cyclohexanone (0.94 g, 5.0 mmol) in chloroform (12 mL) at −5° C. was treated via rapid dropwise addition with a solution of bromine (0.26 mL, 5.1 mmol) in chloroform (6 mL) so as the reaction temperature maintaining below 5° C. The solution was kept at 0° C. for 2 h when the red color had disappeared. The mixture was concentrated under reduced pressure to give the crude title compound (1.35 g, 100%) as a brown oil which was used directly in the next step. MS ISP (m/e): 267.3 [(M+H)$^+$]. $^1$H NMR (DMSO-D$_6$, 300 MHz): δ (ppm)=7.22-7.42 (m, 3H), 7.13 (d, 2H), 4.70 (dd, 1H), 2.75 (m, 1H), 2.52 (m, 1H), 1.7-2.4 (m, 4H), 1.36 (s, 3H).

b) [3-Methoxy-4-(4-methyl-imidazol-1-yl)-phenyl]-(4-methyl-4-phenyl-4,5,6,7-tetrahydro-benzothiazol-2-yl)-amine The title compound was prepared from [3-methoxy-4-(4-methyl-imidazol-1-yl)-phenyl]-thiourea (0.45 g, 1.72 mmol) and 6-bromo-2-methyl-2-phenyl-cyclohexanone (0.69 g, 2.6 mmol) using in analogous manner the procedure described in example 1b). Obtained as an off-white solid (0.29 g, 39%). MS ISP (m/e): 431.4 [(M+H)$^+$]. mp 123-126° C.

Example 31

[3-Fluoro-4-(4-methyl-imidazol-1-yl)-phenyl]-(4-methyl-4-phenyl-4,5,6,7-tetrahydro-benzothiazol-2-yl)-amine

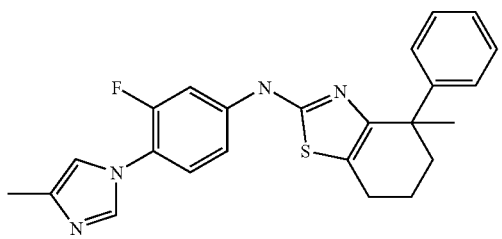

The title compound was prepared from [3-fluoro-4-(4-methyl-imidazol-1-yl)-phenyl]-thiourea (90 mg, 0.36 mmol) and crude 6-bromo-2-methyl-2-phenyl-cyclohexanone (0.29 g, ca. 1.1 mmol) using in analogous manner the procedure described in example 1b). Obtained as a light-brown solid (65 mg, 43%). MS (ISP) 419.3 [(M+H)$^+$]. mp 160-164° C.

Example 32

[3-Fluoro-4-(4-methyl-imidazol-1-yl)-phenyl]-[4-(4-methyl-3-trifluoromethyl-phenyl)-4,5,6,7-tetrahydro-benzothiazol-2-yl]-amine

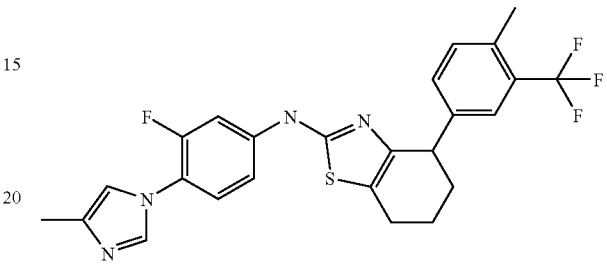

a) 2-(3-Methyl-4-trifluoromethyl-phenyl)-cyclohexanone 2-(4-Methyl-3-trifluoromethyl-phenyl)-cyclohexanol (1.91 g; 7.4 mmol) was oxidized with Dess-Martin periodane using in analogous manner the procedure described in example 62b) to give the title compound (1.80 g, 95%) as a pale-yellow oil. MS EI (m/e): 256.1 [M$^+$].

b) 2-Bromo-6-(3-methyl-4-trifluoromethyl-phenyl)-cyclohexanone 6-(3-Methyl-4-trifluoromethyl-phenyl)-cyclohexanone (128 mg, 0.5 mmol) was brominated using in analogous manner the procedure described in example 30a) to give crude title compound (181 mg) as a brown oil which was used directly in the next step. MS ISP (m/e): 352.1 [(M+NH$_4$)$^+$].

c) [3-Fluoro-4-(4-methyl-imidazol-1-yl)-phenyl]-[4-(4-methyl-3-trifluoromethyl-phenyl)-4,5,6,7-tetrahydro-benzothiazol-2-yl]-amine The title compound was prepared from [3-fluoro-4-(4-methyl-imidazol-1-yl)-phenyl]-thiourea (45 mg, 0.18 mmol) and crude 2-bromo-6-(3-methyl-4-trifluoromethyl-phenyl)-cyclohexanone (181 mg, ca. 0.5 mmol) using in analogous manner the procedure described in example 1b). Obtained as a light-yellow solid (70 mg, 80%). MS ISP (m/e): 487.3 [(M+H)$^+$]; mp 160-163° C.

Example 33

[4-(2-Chloro-phenyl)-4,5,6,7-tetrahydro-benzothiazol-2-yl]-[3-fluoro-4-(4-methyl-imidazol-1-yl)-phenyl]-amine

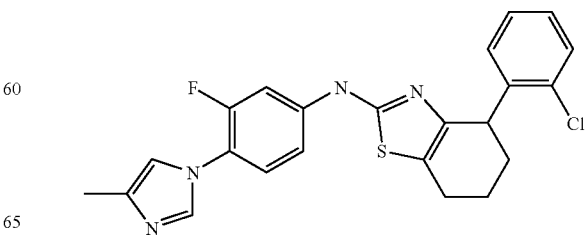

a) 2-Bromo-6-(2-chloro-phenyl)-cyclohexanone 2-(2-Chloro-phenyl)-cyclohexanone (104 mg, 0.5 mmol) was brominated using in analogous manner the procedure described in example 30a) to give crude title compound (145 mg) as a light-brown oil which was used directly in the next step. MS ISP (m/e): 304.0 [(M+NH$_4$)$^+$].

b) 4-(2-Chloro-phenyl)-4,5,6,7-tetrahydro-benzothiazol-2-yl]-[3-fluoro-4-(4-methyl-imidazol-1-yl)-phenyl]-amine The title compound was prepared from [3-fluoro-4-(4-methyl-imidazol-1-yl)-phenyl]-thiourea (45 mg, 0.18 mmol) and 6-bromo-2-(2-chloro-phenyl)-cyclohexanone (145 mg, ca. 0.5 mmol) using in analogous manner the procedure described in example 1b). Obtained as a light-brown solid (68 mg, 76%). MS ISP (m/e): 439.1 [(M+H)$^+$]. mp 204-206° C.

Example 34

[3-Fluoro-4-(4-methyl-imidazol-1-yl)-phenyl]-[4-(4-trifluoromethoxy-phenyl)-4,5,6,7-tetrahydro-benzothiazol-2-yl]-amine

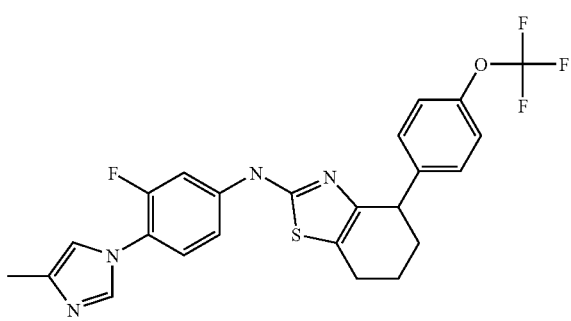

a) 2-Bromo-6-(4-trifluoromethoxy-phenyl)-cyclohexanone 2-(4-Trifluoromethoxy-phenyl)-cyclohexanone (129 mg, 0.5 mmol) was brominated using in analogous manner the procedure described in example 30a) to give crude title compound (170 mg) as a brown oil which was used directly in the next step. MS ISP (m/e): 356 [(M+NH$_4$)$^+$].

b) [3-Fluoro-4-(4-methyl-imidazol-1-yl)-phenyl]-[4-(4-trifluoromethoxy-phenyl)-4,5,6,7-tetrahydro-benzothiazol-2-yl]-amine The title compound was prepared from [3-fluoro-4-(4-methyl-imidazol-1-yl)-phenyl]-thiourea (45 mg, 0.18 mmol) and crude 6-bromo-2-(4-trifluoromethoxy-phenyl)-cyclohexanone (170 mg, ca. 0.5 mmol) using in analogous manner the procedure described in example 1b). Obtained as a light-brown solid (57 mg, 65%). MS ISP (m/e): 489.0 [(M+H)$^+$]. mp 148-151° C.

Example 35

[3-Fluoro-4-(4-methyl-imidazol-1-yl)-phenyl]-[4-(2-methoxy-phenyl)-4,5,6,7-tetrahydro-benzothiazol-2-yl]-amine

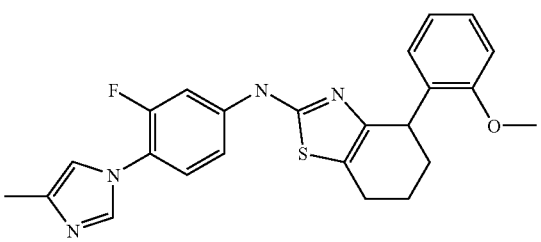

a) 2-Bromo-6-(2-methoxy-phenyl)-cyclohexanone 2-(2-methoxy-phenyl)-cyclohexanone (102 mg, 0.5 mmol) was brominated using in analogous manner the procedure described in example 30a) to give crude title compound (153 mg) as a brown oil which was used directly in the next step. MS ISP (m/e): 283.1 [(M+H)$^+$].

b) [3-Fluoro-4-(4-methyl-imidazol-1-yl)-phenyl]-[4-(2-methoxy-phenyl)-4,5,6,7-tetrahydro-benzothiazol-2-yl]-amine The title compound was prepared from [3-fluoro-4-(4-methyl-imidazol-1-yl)-phenyl]-thiourea (45 mg, 0.18 mmol) and crude 2-bromo-6-(2-methoxy-phenyl)-cyclohexanone (153 mg, 0.50 mmol) using in analogous manner the procedure described in example 1b). Obtained as a light-yellow solid (14 mg, 18%). MS ISP (m/e): 435.4 [(M+H)$^+$]. mp 227-230° C.

Example 36

[4-(2,4-Dichloro-phenyl)-4,5,6,7-tetrahydro-benzothiazol-2-yl]-[3-fluoro-4-(4-methyl-imidazol-1-yl)-phenyl]-amine

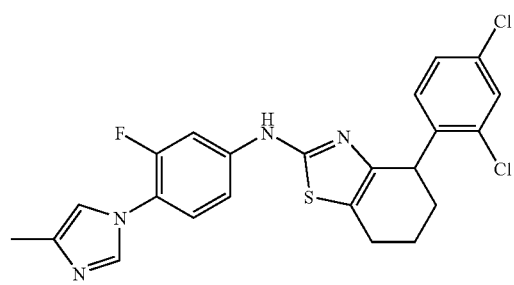

a) 2-Bromo-6-(2,4-dichloro-phenyl)-cyclohexanone 2-(2,4-Dichloro-phenyl)-cyclohexanone (250 mg, 1.03 mmol) was brominated using in analogous manner the procedure described in example 30a) to give crude title compound (350 mg) as a brown solid which was used directly in the next step.

b) [4-(2,4-Dichloro-phenyl)-4,5,6,7-tetrahydro-benzothiazol-2-yl]-[3-fluoro-4-(4-methyl-imidazol-1-yl)-phenyl]-amine The title compound was prepared from [3-fluoro-4-(4-methyl-imidazol-1-yl)-phenyl]-thiourea (109 mg, 0.44 mmol) and crude 2-bromo-6-(2,4-dichloro-phenyl)-cyclohexanone (350 mg, ca. 0.5 mmol) using in analogous manner the procedure described in example 1b). Obtained as a light-brown solid (118 mg, 57%). MS ISP (m/e): 473.1 [(M+H)+]. mp 136-139° C.

Example 37

[3-Methoxy-4-(5-methyl-[1,3,4]oxadiazol-2-yl)-phenyl]-(4-phenyl-4,5,6,7-tetrahydro-benzothiazol-2-yl)-amine

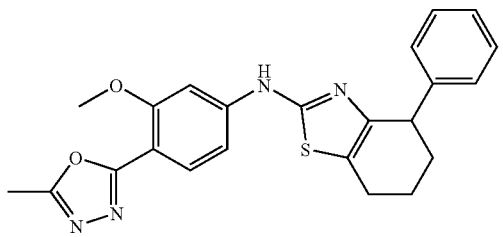

a) 2-Methoxy-4-(4-phenyl-4,5,6,7-tetrahydro-benzothiazol-2-ylamino)-benzoic acid hydrazide To a suspension of 4-(4-phenyl-4,5,6,7-tetrahydro-benzothiazol-2-ylamino)-benzoic acid methyl ester (200 mg, 0.50 mmol) in ethanol (4 mL) was added hydrazine hydrate (0.6 mL) and the mixture was stirred for 7 hours at 90° C. The formed white precipitate was filtered off, washed with ethanol and dried to yield the title compound (130 mg, 65%) as a white solid which was used without further purification in the next step. mp 297-299° C. MS ISP (m/e): 393.5 (100) (M−H)−.

b) 3-Methoxy-4-(5-methyl-[1,3,4]oxadiazol-2-yl)-phenyl]-(4-phenyl-4,5,6,7-tetrahydro-benzothiazol-2-yl)-amine At room temperature, acetic anhydride (108 μL) was added to a suspension of 2-methoxy-4-(4-phenyl-4,5,6,7-tetrahydro-benzothiazol-2-ylamino)-benzoic acid hydrazide (130 mg, 0.33 mmol) in dimethylformamide (5 mL). The mixture was stirred for 40 hours and evaporated to dryness. The residue was taken up in 10% w/w (3 mL) phosphorous pentoxide in methanesulfonic acid (prepared by mixing 5 g phosphorous pentoxide and 30 mL methanesulfonic acid and stirring for 2 h at 90° C.) and stirred for 18 hours. The mixture was poured into 75 ml water, neutralized to pH 5-6 with 32% aqueous sodium hydroxide and the precipitate filtered off. The solid was dissolved in ethyl acetate (30 mL), washed four times with water and once with brine, dried with magnesium sulfate and concentrated in vacuo, affording the title compound (69 mg, 65%) as an off-white solid. NMR (CDCl3, 300 MHz): δ (ppm)=7.74 (d, 1H), 7.61 (d, 1H), 7.31-7.15 (m, 5H), 6.82 (dd, 1H), 4.03 (m, 1H), 3.34 (m, 3H), 2.73 (m, 2H), 2.50 (m, 3H), 2.14 (m, 1H), 1.79 (m, 3H). MS ISP (m/e): 419.1 (100) (M+H)+.

Example 38

[3-Fluoro-4-(4-methyl-imidazol-1-yl)-phenyl]-(8-phenyl-5,6,7,8-tetrahydro-quinazolin-2-yl)-amine

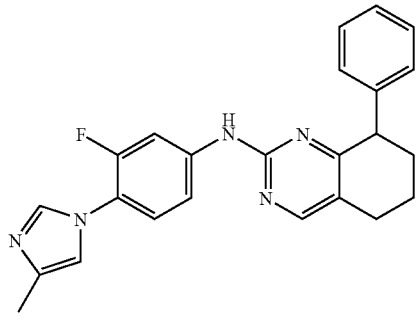

a) 2-[1-Dimethylamino-meth-(Z)-ylidene]-6-phenyl-cyclohexanone

A mixture of 2-phenylcyclohexanone (871 mg, 5.0 mmol) and of tert.-butoxy-bis(dimethylamino)methane (90%, 1.5 mL, 7 mmol) was stirred at 110° C. for 75 min. The reaction was evaporated to dryness under reduced pressure to give the crude title compound (1.16 g, 100%) as a red oil which was used directly in the next step without further purification. MS ISP (m/e): 230.2 (100) [(M+H)+].

b) N-[3-fluoro-4-(4-methyl-imidazol-1-yl)-phenyl]-guanidine nitrate salt

A suspension of 3-fluoro-4-(4-methyl-imidazol-1-yl)-phenylamine (500 mg, 2.62 mmol), of 50% aqueous cyanamide (249 mg, 2.96 mmol) and of 65% aqueous nitric acid (253 mg, 2.62 mmol) in ethanol (2.6 mL) was heated over night to reflux under an atmosphere of nitrogen. The same amounts of cyanamide and nitric acid were added and the mixture was heated to reflux over the weekend. Again the same initial amount of cynamide and nitric acid were added and the reaction was heated to reflux for 2 days. After standing for 1 day at room temperature the precipitated solid was filtered off and washed with ethanol to yield the title compound (280 mg, 36%) as an off-white solid. MS ISP (m/e): 234.1 (100) [(M+H)+]. 1H NMR (DMSO-D6, 300 MHz): δ (ppm)=9.82 (br s, 1H), 7.90 (s, 1H), 7.67 (t, 1H), 7.56 (s, 4H), 7.43 (d, 1H), 7.25 (s, 1H), 7.21 (d, 1H), 2.18 (s, 1H).

c) [3-Fluoro-4-(4-methyl-imidazol-1-yl)-phenyl]-(8-phenyl-5,6,7,8-tetrahydro-quinazolin-2-yl)-amine To a suspension of N-[3-fluoro-4-(4-methyl-imidazol-1-yl)-phenyl]-guanidine nitrate salt (100 mg, 0.34 mmol) and crude 2-[1-dimethylamino-meth-(Z)-ylidene]-6-phenyl-cyclohexanone (174 mg, 0.76 mmol) in ethanol (2 mL) was added triethyl amine (159 mg, 1.58 mmol). The mixture was heated to reflux under an atmosphere of nitrogen for 2 days. After cooling to room temperature the solvent was evaporated under reduced pressure and the residue was the residue was purified by column chromatography on silica gel using dichloromethane/methanol (19:1 v/v) as eluent to yield the title compound (33 mg, 24%) as a yellow gum. MS ISP (m/e): 400.3 (100) [(M+H)+]. $^1$H NMR (DMSO-D$_6$, 300 MHz): δ (ppm)=9.78 (s, 1H), 8.37 (s, 1H), 7.74 (d, 1H), 7.72 (s, 1H), 7.09-7.33 (m, 8H), 4.11 (t, 1H), 2.74 (m, 2H), 2.14 (s, 3H), 1.69-1.95 (m, 3H).

Example 39

[3-Methoxy-4-(4-methyl-imidazol-1-yl)-phenyl]-(8-phenyl-5,6,7,8-tetrahydro-quinazolin-2-yl)-amine

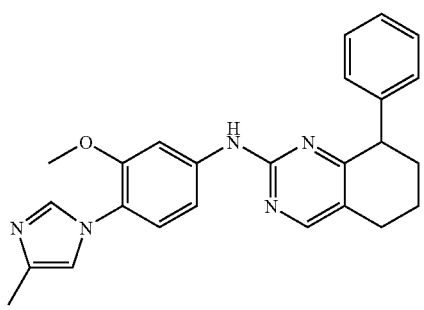

a) N-[3-Methoxy-4-(4-methyl-imidazol-1-yl)-phenyl]-guanidine dinitrate salt

To a solution of 3-methoxy-4-(4-methyl-imidazol-1-yl)-phenylamine (5.08 g (25.0 mmol) in ethanol (25 mL) was added at room temperature cyanamide (3.15 g (75 mmol) dissolved in water (3.2 mL) and then 37% aqueous hydrochloric acid solution (4.9 g (50 mmol). The solution was heated for 3 hours to reflux. Additional cyanamide (2.1 g) in water (2.1 mL) and 37% aq hydrochloric acid solution (2.8 mL) were added and the mixture was heated to reflux for another 2 hours. At room temperature 65% aqueous nitric acid (3.5 mL, 50 mmol) was added. The reaction was stirred for 30 minute at room temperature and the formed precipitate was filtered off, washed with ethanol and diethyl ether. The solid was dried under reduced pressure at room temperature to yield the title compound (5.42 g, 58%) as a white solid. MS ISP (m/e): 246.1 (100) [(M+H)+]. $^1$H NMR (DMSO-D$_6$, 300 MHz): δ (ppm)=10.17 (s, 1H), 9.34 (s, 1H), 8.40 (br s, 2H), 7.67 (br s, 4H), 7.63 (d, 1H), 7.21 (s, 1H), 6.99 (d, 1H), 3.88 (s, 3H), 2.35 (s, 3H).

b) [3-Methoxy-4-(4-methyl-imidazol-1-yl)-phenyl]-(8-phenyl-5,6,7,8-tetrahydro-quinazolin-2-yl)-amine To a suspension of N-[3-methoxy-4-(4-methyl-imidazol-1-yl)-phenyl]-guanidine dinitrate salt (74.3 mg, 0.20 mmol) and of crude 2-[1-dimethylamino-meth-(Z)-ylidene]-6-phenyl-cyclohexanone (137.6 mg, 0.60 mmol) in ethanol (2 mL) was added triethyl amine (40.5 mg, 0.40 mmol). The mixture was heated to reflux under an atmosphere of nitrogen over night. After cooling to room temperature the solvent was evaporated under reduced pressure and the residue was purified twice by column chromatography on silica gel using dichloromethane/methanol (19:1 v/v) as eluent to yield the title compound (44 mg, 53%) as a pale-yellow solid. MS ISP (m/e): 412.3 (100) [(M+H)+]. $^1$H NMR (DMSO-D$_6$, 300 MHz): δ (ppm)=9.54 (s, 1H), 8.36 (s, 1H), 7.70 (d, 1H), 7.57 (s, 1H), 7.38 (t, 2H), 7.20 (t, 1H), 7.02-7.14 (m, 4H), 6.94 (s, 3H), 4.13 (t, 1H), 3.37 (s, 3H), 2.73 (m, 2H), 2.18 (m, 1H), 2.11 (s, 3H), 1.65-1.89 (m, 3H).

Example 40

2-[3-Methoxy-4-(4-methyl-imidazol-1-yl)-phenylamino]-8-phenyl-7,8-dihydro-5H-pyrido[4,3-d]pyrimidine-6-carboxylic acid tert.-butyl ester

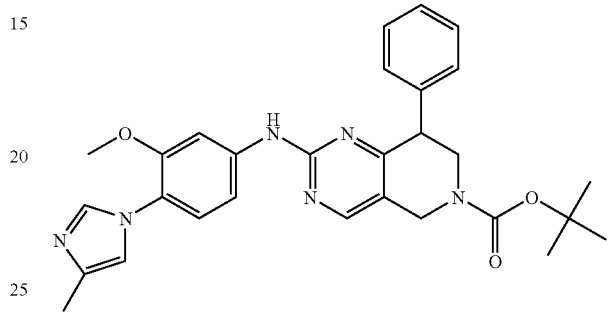

a) 3-[1-Dimethylamino-meth-(Z)-ylidene]-4-oxo-5-phenyl-piperidine-1-carboxylic acid tert.-butyl ester A mixture of 1-boc-3-phenyl-piperidin-4-one (100 mg, 0.35 mmol) and tert.-butoxy-bis(dimethylamino)methane (94 mg, 0.48 mmol) was stirred at 110° C. for 2 hours. The reaction was evaporated to dryness, treated twice with toluene and evaporated under reduced pressure to dryness to yield the title compound (215 mg, 188%) as a brown oil which was used directly in the next step without further purification. MS ISP (m/e): 331.4 (79) [(M+H)+], 275.1 (100) [(M-isubutene +H)+].

b) 2-[3-Methoxy-4-(4-methyl-imidazol-1-yl)-phenylamino]-8-phenyl-7,8-dihydro-5H-pyrido[4,3-d]pyrimidine-6-carboxylic acid tert.-butyl ester To a suspension of N-[3-methoxy-4-(4-methyl-imidazol-1-yl)-phenyl]-guanidine dinitrate salt (107 mg, 0.29 mmol) and of crude of 3-[1-dimethylamino-meth-(Z)-ylidene]-4-oxo-5-phenyl-piperidine-1-carboxylic acid tert.-butyl ester (214 mg, 0.65 mmol) in ethanol (3 mL) was added triethyl amine (136 mg, 1.35 mmol). The mixture was heated to reflux under an atmosphere of nitrogen for 2 days. After cooling to room temperature the solvent was evaporated under reduced pressure and the residue was purified by column chromatography on silica gel using dichloromethane/methanol (19:1 v/v) as eluent to yield the title compound (84 mg, 57%) as a brown gum. MS ISN (m/e): 511.7 (100) [(M−H)−]. $^1$H NMR (DMSO-D$_6$, 300 MHz): δ (ppm)=9.74 (s, 1H), 8.52 (s, 1H), 7.74 (s, 1H), 7.59 (s, 1H), 7.09-7.30 (m, 7H), 4.82 & 4.34 (2 br m, 1H), 4.18 (t, 1H), 3.98 & 3.68 (2 br m, 3H), 3.47 (s, 3H), 2.12 (s, 3H), 1.13 (br s, 9H).

Example 41

[3-Methoxy-4-(4-methyl-imidazol-1-yl)-phenyl]-(8-phenyl-5,6,7,8-tetrahydro-pyrido[4,3-d]pyrimidin-2-yl)-amine hydrochloride

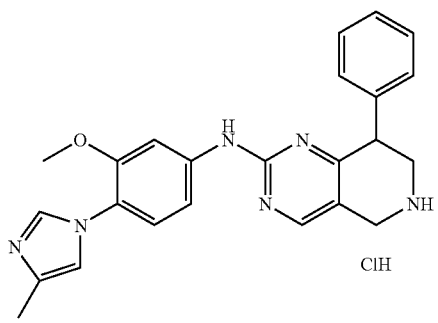

To a solution of 2-[3-methoxy-4-(4-methyl-imidazol-1-yl)-phenylamino]-8-phenyl-7,8-dihydro-5H-pyrido[4,3-d]pyrimidine-6-carboxylic acid tert.-butyl ester (75 mg, 0.15 mmol) in dichloromethane (1.5 mL) was added at 0° C. 2M hydrogene chloride (0.73 mL) in diethyl ether. The reaction was stirred at room temperature over night. The solvent was evaporated under reduced pressure to yield the title compound (70 mg, 100%) as a yellow solid. MS ISP (m/e): 413.4 (100) [(M+H)+]. 1H NMR (DMSO-D6, 300 MHz): δ (ppm)=10.01 (m, 2H), 9.23 (s, 1H), 8.57 (s, 1H), 7.71 (s, 1H), 7.59 (s, 1H), 7.26-7.38 (m, 6H), 7.15 (d, 1H), 4.56 (dd, 1H), 4.37 (m, 2H), 3.64 (m, 1H), 3.42 (m, 1H), 3.38 (s, 3H), 2.32 (s, 3H).

Example 42

1-{2-[3-Methoxy-4-(4-methyl-imidazol-1-yl)-phenylamino]-8-phenyl-7,8-dihydro-5H-pyrido[4,3-d]pyrimidin-6-yl}-ethanone

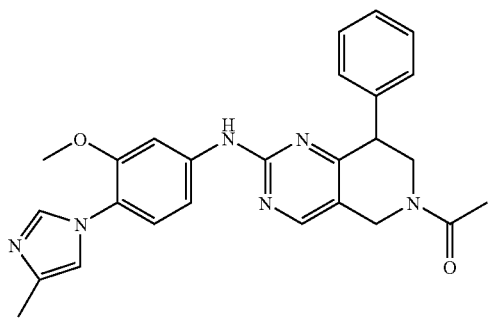

To a suspension of [3-methoxy-4-(4-methyl-imidazol-1-yl)-phenyl]-(8-phenyl-5,6,7,8-tetrahydro-pyrido[4,3-d]pyrimidin-2-yl)-amine hydrochloride (65 mg, 0.15 mmol) in methylen chloride (2 mL) was added at room temperature NN,-diisopropyl ethyl amine (28 mg, 0.22 mmol) and after 2 minutes acetyl chloride (12.5 mg, 0.16 mmol). The reaction was stirred at room temperature over night. The solvent was evaporated under reduced pressure and the residue was purified by column chromatography on silica gel using dichloromethane/methanol (19:1 v/v) as eluent to yield the title compound (20 mg, 30%) as a yellow gum. MS ISP (m/e): 455.3 (100) [(M+H)+]. 1H NMR (CDCl3, 300 MHz): δ (ppm)=8.38 (s, 1H), 7.61 (s, 1H), 7.56 (s, 1H), 7.20-7.33 (m, 3H), 7.05-7.08 (m, 3H), 6.81 (s, 1H), 6.79 (d, 1H), 5.18 (d, 1H), 4.46 (d, 1H), 4.21 (t, 1H), 3.90 (m, 2H), 3.46 (s, 3H), 2.27 (s, 3H), 1.71 (s, 3H).

Example 43

(6-Methanesulfonyl-8-phenyl-5,6,7,8-tetrahydro-pyrido[4,3-d]pyrimidin-2-yl)-[3-methoxy-4-(4-methyl-imidazol-1-yl)-phenyl]-amine

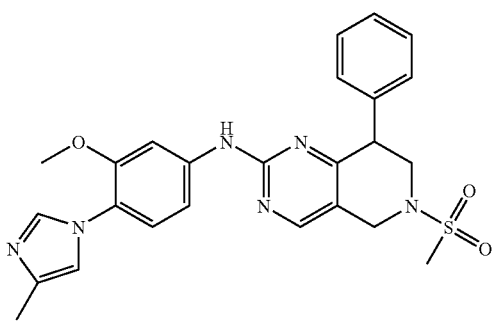

To a suspension of [3-methoxy-4-(4-methyl-imidazol-1-yl)-phenyl]-(8-phenyl-5,6,7,8-tetrahydro-pyrido[4,3-d]pyrimidin-2-yl)-amine hydrochloride (75 mg, 0.17 mmol) in methylen chloride (2 mL) was added at room temperature NN,-diisoprpyl ethyl amine (33 mg, 0.25 mmol) and methanesulfonyl chloride (21.3 mg, 0.18 mmol). The reaction was stirred at room temperature over night. The solvent was evaporated under reduced pressure and the residue was purified by column chromatography on silica gel using dichloromethane/methanol (19:1 v/v) as eluent to yield the title compound (13 mg, 16%) as a yellow solid. MS ISP (m/e): 491.0 (100) [(M+H)+]. 1H NMR (CDCl3, 300 MHz): δ (ppm)=8.33 (s, 1H), 7.70 (s, 1H), 7.59 (s, 1H), 7.26-7.35 (m, 3H), 7.17 (d, 2H), 7.05 (d, 1H), 6.82 (s, 1H), 6.77 (d, 1H), 4.56 (d, 1H), 4.46 (d, 1H), 4.32 (t, 1H), 3.97 (dd, 1H), 3.43 (dd, 1H), 3.38 (s, 3H), 2.80 (s, 3H), 2.30 (s, 3H).

Example 44

(6-Ethyl-8-phenyl-5,6,7,8-tetrahydro-pyrido[4,3-d]pyrimidin-2-yl)-[3-methoxy-4-(4-methyl-imidazol-1-yl)-phenyl]-amine

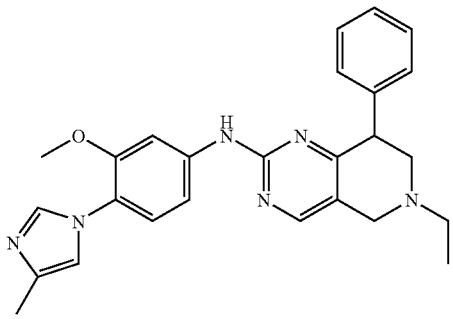

To a suspension of [3-methoxy-4-(4-methyl-imidazol-1-yl)-phenyl]-(8-phenyl-5,6,7,8-tetrahydro-pyrido[4,3-d]pyrimidin-2-yl)-amine hydrochloride (75 mg, 0.17 mmol) in tetrahydrofuran (3.3 mL) was added at room temperature NN,-diisoprpyl ethyl amine (43 mg, 0.33 mmol). After stirring for 5 minutes at room temperature acetaldehyde (8.1 mg, 0.18 mmol), acetic acid (20 mg, 0.33 mmol) and sodium triacetoxyborohydride (106 mg, 0.50 mmol) were added. The reaction was stirred at room temperature over night. The solvent was evaporated under reduced pressure and the residue was purified by column chromatography on silica gel using dichloromethane/methanol (95:5 v/v) as eluent to yield the title compound (45 mg, 61%) as a yellow gum. MS ISN (m/e): 439.6 (100) [(M−H)⁻]. ¹H NMR (CDCl₃, 300 MHz): δ (ppm)=8.24 (s, 1H), 7.62 (s, 1H), 7.54 (s, 1H), 7.20-7.34 (m, 5H), 7.02 (d, 1H), 6.79 (s, 1H), 6.70 (d, 1H), 4.24 (m, 1H), 3.76 (d, 1H), 3.54 (d, 1H), 3.33 (s, 3H), 3.20 (dd, 1H), 2.60 (m, 3H), 2.67 (s, 3H), 1.17 (t, 3H).

Example 45

[3-Methoxy-4-(4-methyl-imidazol-1-yl)-phenyl]-(8-methyl-8-phenyl-5,6,7,8-tetrahydro-quinazolin-2-yl)-amine

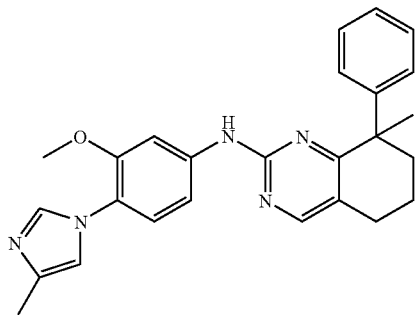

a) 6-[1-Dimethylamino-methylidene]-2-methyl-2-phenylcyclohexanone

A mixture 2-methyl-2-phenylcyclohexanone (94 mg, 0.5 mmol) and tert.-butoxy-bis-(dimethylamino)-methane (0.16 mL, 0.77 mmol) was stirred at 110° C. for 1.5 h, whereupon it was cooled and evaporated under reduced pressure. Toluene (3 mL) was added to the residue and the solution was evaporated again to give the title compound (124 mg) as red oil which was used without further purification. MS ISP (m/e): 244.4 [(M+H)⁺].

b) [3-Methoxy-4-(4-methyl-imidazol-1-yl)-phenyl]-(8-methyl-8-phenyl-5,6,7,8-tetrahydro-quinazolin-2-yl)-amine A mixture of 6-[1-dimethylamino-methylidene]-2-methyl-2-phenylcyclohexanone (103 mg, 0.42 mmol), N-[3-methoxy-4-(4-methyl-imidazol-1-yl)-phenyl]-guanidine dinitrate (157 mg, 0.42 mmol), and triethylamine (0.29 mL, 2.1 mmol) in ethanol (1 mL) was heated at reflux for 18 h. The mixture was cooled, diluted with ethyl acetate (30 mL) and then washed with saturated aqueous sodium carbonate solution (10 mL) and with brine (10 mL). The organic layer was dried over sodium sulfate and evaporated under reduced pressure. The residual material was purified by column chromatography on silica gel using dichloromethane/methanol (20:1 v/v) as eluent to give the title compound (34 mg, 19%). MS ISP (m/e): 426.1 [(M+H)⁺]. mp 207-209° C.

Example 46

[3-Methoxy-4-(4-methyl-imidazol-1-yl)-phenyl]-[8-(3-methoxy-phenyl)-8-propyl-5,6,7,8-tetrahydro-quinazolin-2-yl]-amine

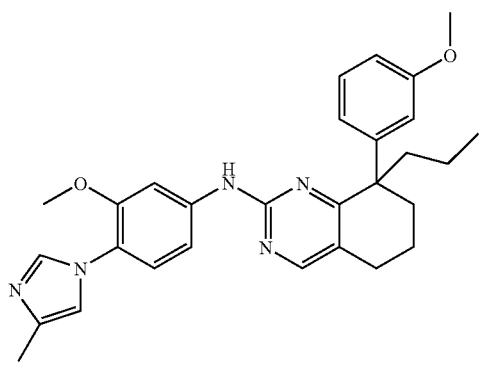

a) 2-(3-Methoxy-phenyl)-2-propyl-cyclohexanone

A solution of 2-(3-methoxy-phenyl)-cyclohexanone (2.04 g, 10.0 mmol) in N,N-dimethylformamide (10 mL) was added over 10 min to a mixture of sodium hydride (0.29 g, 12.0 mmol) in N,N-dimethylformamide (4 mL), the temperature being kept below 30° C. The reaction mixture was stirred at 20-25° C. for 2 h. A solution of 1-iodo-propane (1.17 mL, 12.0 mmol) in N,N-dimethylformamide (2 mL) was added over 10 min at 20-25° C. The mixture was stirred for 18 h, and then, ethanol (2 mL) was slowly added. The mixture was stirred for 0.5 h and then poured onto ice-water. The mixture was extracted with dichloromethane. The organic layer was separated, washed with water, and dried over sodium sulfate. Solvents were removed under reduced pressure and the remaining oil was purified by column chromatography on silica gel using heptane/diethyl ether (4:1, v/v) as eluent to give the title compound (0.74 g, ca. 30%) as pale-yellow oil. MS ISP (m/e): 247.3 [(M+H)⁺].

b) 6-[1-Dimethylamino-methylidene]-2-(3-methoxy-phenyl)-2-propyl-cyclohexanone 2-(3-Methoxy-phenyl)-2-propyl-cyclohexanone (101 mg, 0.41 mmol) was reacted with tert.-butoxy-bis-(dimethylamino)-methane using in analogous manner the procedure described in example 45a) to give crude title compound (124 mg) as red oil which was used directly in the next step. MS ISP (m/e): 302.1 [(M+H)⁺].

c) [3-Methoxy-4-(4-methyl-imidazol-1-yl)-phenyl]-[8-(3-methoxy-phenyl)-8-propyl-5,6,7,8-tetrahydro-quinazolin-2-yl]-amine The title compound was prepared from 6-[1-dimethylamino-methylidene]-2-(3-methoxy-phenyl)-2-propyl-cyclohexanone (101 mg, 0.33 mmol) and N-[3-methoxy-4-(4-methyl-imidazol-1-yl)-phenyl]-guanidine dinitrate (124 mg, 0.33 mmol) using in analogous manner the procedure described in example 45b). Obtained as white solid (24 mg, 15%). MS ISP (m/e): 484.5 [(M+H)⁺]. mp 166-168° C.

Example 47

[3-Methoxy-4-(4-methyl-imidazol-1-yl)-phenyl]-[8-(3-trifluoromethyl-phenyl)-5,6,7,8-tetrahydro-quinazolin-2-yl]-amine

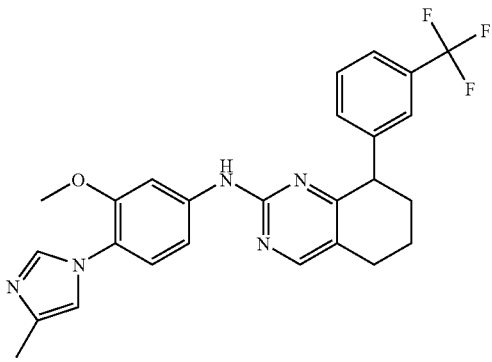

a) 6-[1-Dimethylamino-methylidene]-2-(3-trifluoromethyl-phenyl)-cyclohexanone 2-(3-Trifluoromethyl-phenyl)-cyclohexanone (106 mg, 0.44 mmol) was reacted with tert.-butoxy-bis-(dimethylamino)-methane using in analogous manner the procedure described in example 45a), to give crude title compound (132 mg) as a red oil which was used directly in the next step. MS ISP (m/e): 298.0 [(M+H)$^+$]

b) [3-Methoxy-4-(4-methyl-imidazol-1-yl)-phenyl]-[8-(3-trifluoromethyl-phenyl)-5,6,7,8-tetrahydro-quinazolin-2-yl]-amine The title compound was prepared from 6-[1-dimethylamino-methylidene]-2-(3-trifluoromethyl-phenyl)-cyclohexanone (132 g, 0.44 mmol) and N-[3-methoxy-4-(4-methyl-imidazol-1-yl)-phenyl]-guanidine dinitrate (163 mg, 0.44 mmol) using in analogous manner the procedure described in example 45b). Obtained as an off-white solid (62 mg, 29%). MS ISP (m/e): 480.1 [(M+H)$^-$]. mp 213-215° C.

Example 48

[8-(2,4-Dichloro-phenyl)-5,6,7,8-tetrahydro-quinazolin-2-yl]-[3-methoxy-4-(4-methyl-imidazol-1-yl)-phenyl]-amine

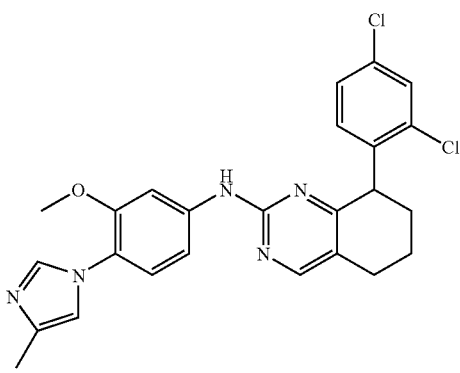

a) 6-[1-Dimethylamino-methylidene]-2-(2,4-dichloro-phenyl)-cyclohexanone 2-(2,4-dichloro-phenyl)-cyclohexanone (101 mg, 0.42 mmol) was reacted with tert.-butoxy-bis-(dimethylamino)-methane using in analogous manner the procedure described in example 45a) to give crude title compound (105 mg) as a red oil which was used directly in the next step. MS ISP (m/e): 298.3 [(M+H)$^+$].

b) [8-(2,4-Dichloro-phenyl)-5,6,7,8-tetrahydro-quinazolin-2-yl]-[3-methoxy-4-(4-methyl-imidazol-1-yl)-phenyl]-amine The title compound was prepared from 6-[1-dimethylamino-methylidene]-2-(2,4-dichloro-phenyl)-cyclohexanone (105 mg, 0.35 mmol) and N-[3-methoxy-4-(4-methyl-imidazol-1-yl)-phenyl]-guanidine dinitrate (131 mg, 0.35 mmol) using in analogous manner the procedure described in example 45b). Obtained as an off-white solid (19 mg, 11%). MS ISP (m/e): 480.1 [(M+H)$^+$]. mp 256-258° C.

Example 49

[8-(3,4-Dichloro-phenyl)-5,6,7,8-tetrahydro-quinazolin-2-yl]-[3-methoxy-4-(4-methyl-imidazol-1-yl)-phenyl]-amine

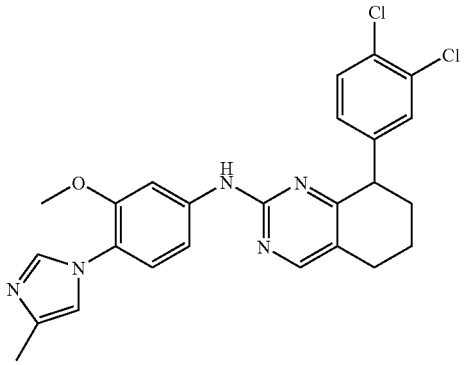

a) 6-[1-Dimethylamino-methylidene]-2-(3,4-dichloro-phenyl)-cyclohexanone (U12a)

2-(3,4-Dichloro-phenyl)-cyclohexanone (101 mg, 0.42 mmol) was reacted with tert.-butoxy-bis-(dimethylamino)-methane using in analogous manner the procedure described in example 45a) to give crude title compound (119 mg) as a red oil which was used directly in the next step. MS ISP (m/e): 298.0 [(M+H)$^+$].

b) [8-(3,4-Dichloro-phenyl)-5,6,7,8-tetrahydro-quinazolin-2-yl]-[3-methoxy-4-(4-methyl-imidazol-1-yl)-phenyl]-amine The title compound was prepared from 6-[1-dimethylamino-methylidene]-2-(3,4-dichloro-phenyl)-cyclohexanone (119 mg, 0.40 mmol) and N-[3-methoxy-4-(4-methyl-imidazol-1-yl)-phenyl]-guanidine dinitrate (148 mg, 0.40 mmol) using in analogous manner the procedure described in example 45b). Obtained as an off-white solid (92 mg, 48%). MS ISP (m/e): 480.0 [(M+H)$^+$]. mp 167-169° C.

Example 50

[8-(4-Chloro-phenyl)-5,6,7,8-tetrahydro-quinazolin-2-yl]-[3-methoxy-4-(4-methyl-imidazol-1-yl)-phenyl]-amine

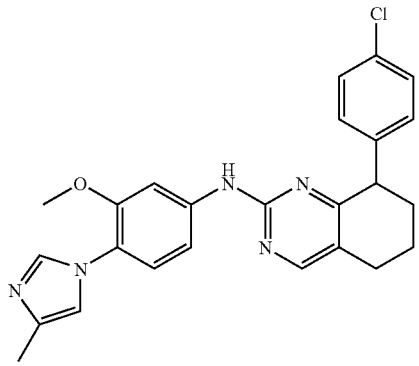

a) 6-[1-Dimethylamino-methylidene]-2-(4-chloro-phenyl)-cyclohexanone (U15a)

2-(4-Chloro-phenyl)-cyclohexanone (104 mg, 0.5 mmol) was reacted with tert.-butoxy-bis-(dimethylamino)-methane using in analogous manner the procedure described in example 45a) to give crude title compound (134 mg) as a red oil which was used directly in the next step. MS ISP (m/e): 264.0 [(M+H)$^+$].

b) [8-(4-Chloro-phenyl)-5,6,7,8-tetrahydro-quinazolin-2-yl]-[3-methoxy-4-(4-methyl-imidazol-1-yl)-phenyl]-amine The title compound was prepared from 6-[1-dimethylamino-methylidene]-2-(4-chloro-phenyl)-cyclohexanone (134 mg, 0.50 mmol) and N-[3-methoxy-4-(4-methyl-imidazol-1-yl)-phenyl]-guanidine dinitrate (186 mg, 0.50 mmol) using in analogous manner the procedure described in example 45b). Obtained as an off-white solid (69 mg, 31%). MS ISP (m/e): 446.1 [(M+H)$^+$]. mp 210-212° C.

Example 51

[8-(4-Fluoro-phenyl)-5,6,7,8-tetrahydro-quinazolin-2-yl]-[3-methoxy-4-(4-methyl-imidazol-1-yl)-phenyl]-amine

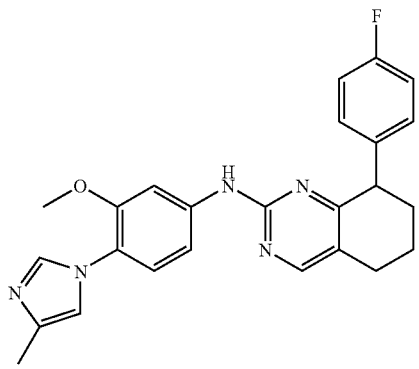

a) 6-[1-Dimethylamino-methylidene]-2-(4-fluoro-phenyl)-cyclohexanone (U11a)

2-(4-Fluoro-phenyl)-cyclohexanone (102 mg, 0.53 mmol) was reacted with tert.-butoxy-bis-(dimethylamino)-methane using in analogous manner the procedure described in example 45a) to give crude title compound (143 mg) as a red oil which was used directly in the next step. MS ISP (m/e): 248.1 [(M+H)$^+$].

b) [8-(4-Fluoro-phenyl)-5,6,7,8-tetrahydro-quinazolin-2-yl]-[3-methoxy-4-(4-methyl-imidazol-1-yl)-phenyl]-amine The title compound was prepared from 6-[1-dimethylamino-methylidene]-2-(4-fluoro-phenyl)-cyclohexanone (143 mg, 0.53 mmol) and N-[3-methoxy-4-(4-methyl-imidazol-1-yl)-phenyl]-guanidine dinitrate (195 mg, 0.53 mmol) using in analogous manner the procedure described in example 45b). Obtained as an off-white solid (71 mg, 31%). MS ISP (m/e): 430.5 [(M+H)$^+$]. mp 191-193° C.

Example 52

{8-(4-Chloro-phenyl)-2-[3-methoxy-4-(4-methyl-imidazol-1-yl)-phenylamino]-5,6,7,8-tetrahydro-quinazolin-8-yl}-acetonitrile

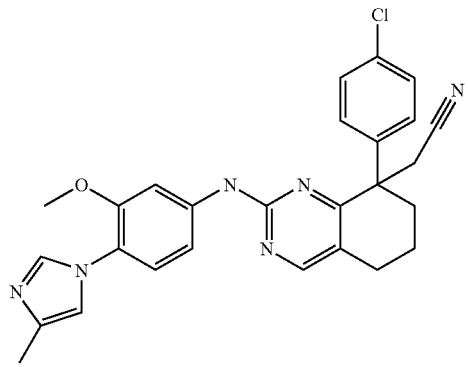

a) [1-(4-Chlorophenyl)-2-oxo-cyclohexyl]-acetonitrile

A solution of 2-(4-chlorophenyl)-cyclohexanone (100 g, 0.48 mol) in N,N-dimethylformamide (0.5 L) was added slowly to a mixture of sodium hydride (13.8 g, 0.78 mol) in N,N-dimethylformamide (0.2 L), the temperature being kept below 40° C. The reaction mixture was stirred at 20-25° C. for 1.5 h when a precipitate was formed. The mixture was diluted with N,N-dimethylformamide (0.2 L), and thereafter, a solution of chloroacetonitrile (43.0 g, 0.57 mol) in N,N-dimethylformamide (0.1 L) was slowly added with cooling over 0.5 h, the temperature being kept below 25° C. The mixture was stirred for 18 h, and then, ethanol (50 mL) was slowly added. The mixture was stirred for 0.5 h and then poured onto ice-water.

Mixture was extracted with dichloromethane. The organic layer was separated, washed with water, and dried over sodium sulfate. Solvents were removed under reduced pressure and the remaining oil was purified by column chromatography on silica gel using heptane/diethyl ether (4:1, v/v) as eluent to give the title compound (40.8 g, 34%) as a white solid (from diethyl ether/hexane). mp. 86-87° C.

b) [1-(4-Chloro-phenyl)-3-[1-dimethylamino-methylidene]-2-oxo-cyclohexyl]-acetonitrile

[1-(4-Chlorophenyl)-2-oxo-cyclohexyl]-acetonitrile (101 mg, 0.43 mmol) was reacted with tert.-butoxy-bis-(dimethylamino)-methane using in analogous manner the procedure described in example 45a) to give crude title compound (149 mg) as a red oil which was used directly in the next step.

c) {8-(4-Chloro-phenyl)-2-[3-methoxy-4-(4-methyl-imidazol-1-yl)-phenylamino]-5,6,7,8-tetrahydro-quinazolin-8-yl}-acetonitrile The title compound was prepared from [1-(4-chloro-phenyl)-3-[1-dimethylamino-methylidene]-2-oxo-cyclohexyl]-acetonitrile (118 mg, 0.39 mmol) and N-[3-methoxy-4-(4-methyl-imidazol-1-yl)-phenyl]-guanidine dinitrate (124 mg, 0.33 mmol) using in analogous manner the procedure described in example 45b). Obtained as an off-white solid (114 mg, 71%). MS ISP (m/e): 485.5 [(M+H)+]. mp 156-158° C.

Example 53

2-[3-Methoxy-4-(4-methyl-imidazol-1-yl)-phenylamino]-6-methyl-8-phenyl-5,6,7,8-tetrahydro-pyrido[4,3-d]pyrimidin-4-ol

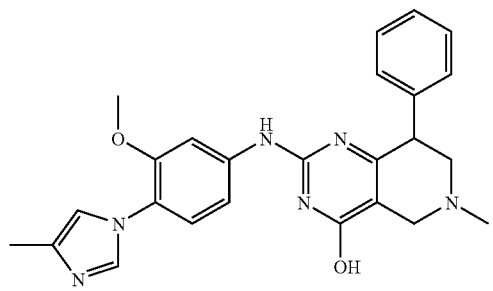

A mixture of 1-methyl-4-oxo-5-phenyl-piperidine-3-carboxylic acid ethyl ester hydrochloride (89 mg, 0.3 mmol), N-[3-methoxy-4-(4-methyl-imidazol-1-yl)-phenyl]-guanidine dinitrate (111 mg, 0.33 mmol), and triethylamine (0.21 mL, 1.5 mmol) in ethanol (2 mL) was heated at 78° C. for 18 h. The mixture was cooled, diluted with ethyl acetate (40 mL), and then washed with saturated aqueous sodium carbonate solution (10 mL) and with brine (10 mL). The organic layer was dried over sodium sulfate and evaporated under reduced pressure. The residual material was purified by column chromatography on silica gel using ethyl acetate/0-30% ethanol as eluent to give the title compound (43 mg, 32%) as a brown solid (from ethyl acetate/cyclohexane). MS ISP (m/e): 443.5 [(M+H)+]. mp 152-155° C.

Example 54

Ethyl 2-[3-methoxy-4-(4-methyl-imidazol-1-yl)-phenylamino]-5,6,7,8-tetrahydro-quinazoline-8-carboxylate

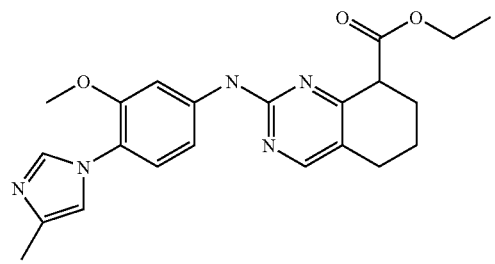

a) Ethyl 3-[1-dimethylamino-methylidene]-2-oxo-cyclohexanecarboxylate

Ethyl 2-oxo-cyclohexanecarboxylate (38 mg, 0.22 mmol) was reacted with tert.-butoxy-bis-(dimethylamino)-methane using in analogous manner the procedure described in example 45a) to give crude title compound (49 mg) as a yellow oil which was used directly in the next step. MS ISP (m/e): 226.1 [(M+H)+].

b) Ethyl 2-[3-methoxy-4-(4-methyl-imidazol-1-yl)-phenylamino]-5,6,7,8-tetrahydro-quinazoline-8-carboxylate The title compound was prepared from ethyl 3-[1-dimethylamino-methylidene]-2-oxo-cyclohexanecarboxylate (49 mg, 0.22 mmol) and N-[3-methoxy-4-(4-methyl-imidazol-1-yl)-phenyl]-guanidine dinitrate (55 mg, 0.15 mmol) using in analogous manner the procedure described in example 45b). Obtained as a pale-yellow solid (8 mg, 10%). MS ISP (m/e): 408.4 [(M+H)+]. mp 162-164° C.

Example 55

Methyl 6,6-ethylendioxy-2-[3-methoxy-4-(4-methyl-imidazol-1-yl)-phenylamino]-5,6,7,8-tetrahydro-quinazoline-8-carboxylate

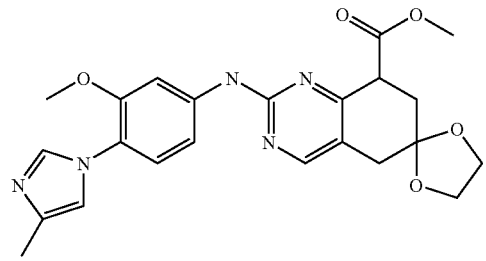

a) Methyl 9-[1-dimethylamino-methylidene]-8-oxo-1,4-dioxa-spiro[4.5]decane-7-carboxylate Methyl 8-oxo-1,4-dioxa-spiro[4.5]decane-7-carboxylate (64 mg, 0.3 mmol) was reacted with tert.-butoxy-bis-(dimethylamino)-methane using in analogous manner the procedure described in example 45a) to give crude title compound (80 mg) as a red oil which was used directly in the next step. MS ISP (m/e): 270.3 [(M+H)+].

b) Methyl 6,6-ethylendioxy-2-[3-methoxy-4-(4-methyl-imidazol-1-yl)-phenylamino]-5,6,7,8-tetrahydro-quinazoline-8-carboxylate The title compound was prepared from methyl 9-[1-dimethylamino-methylidene]-8-oxo-1,4-dioxa-spiro[4.5]decane-7-carboxylic acid methyl ester (80 mg, 0.3 mmol) and N-[3-methoxy-4-(4-methyl-imidazol-1-yl)-phenyl]-guanidine dinitrate (83 mg, 0.22 mmol) using in analogous manner the procedure described in example 45b). Obtained as a pale-yellow solid (37 mg, 27%). MS ISP (m/e): 452.1 [(M+H)⁺]. mp 180-182° C.

Example 56

[3-Fluoro-4-(4-methyl-imidazol-1-yl)-phenyl]-(8-methyl-8-phenyl-5,6,7,8-tetrahydro-quinazolin-2-yl)-amine

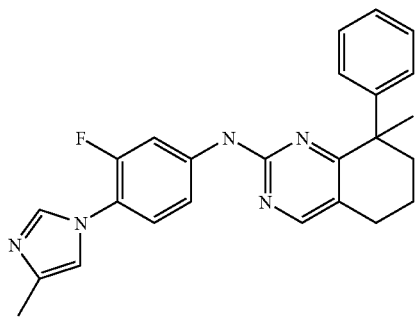

The title compound was prepared from 6-[1-dimethylamino-methylidene]-2-methyl-2-phenylcyclohexanone (117 mg, 0.48 mmol) and N-[3-fluoro-4-(4-methyl-imidazol-1-yl)-phenyl]-guanidine dinitrate (130 mg, 0.36 mmol) using in analogous manner the procedure described in example 48b). Obtained as a pale-yellow solid (44 mg, 30%). MS ISP (m/e): 414.4 [(M+H)⁺]. mp 157-158° C.

Example 57

[3-Fluoro-4-(4-methyl-imidazol-1-yl)-phenyl]-[8-(3-trifluoromethyl-phenyl)-5,6,7,8-tetrahydro-quinazolin-2-yl]-amine

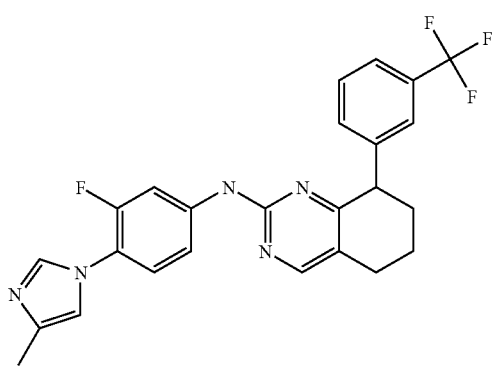

The title compound was prepared from crude 6-[1-dimethylamino-methylidene]-2-(3-trifluoromethyl-phenyl)-cyclohexanone (172 mg, 0.5 mmol) and N-[3-fluoro-4-(4-methyl-imidazol-1-yl)-phenyl]-guanidine dinitrate (134 mg, 0.37 mmol) using in analogous manner the procedure described in example 45b). Obtained as a pale-yellow solid (106 mg, 61%). MS ISP (m/e): 468.3 [(M+H)⁺]. mp 207-209° C.

Example 58

Methyl 2-[3-methoxy-4-(4-methyl-imidazol-1-yl)-phenylamino]-7,8-dihydro-5H-pyrano[4,3-d]pyrimidine-8-carboxylate

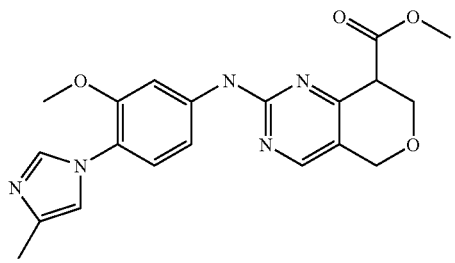

a) Methyl 5-[1-dimethylamino-methylidene]-4-oxo-tetrahydro-pyran-3-carboxylate

Methyl 4-oxo-tetrahydro-pyran-3-carboxylate (74 mg, 0.47 mmol) was reacted with tert.-butoxy-bis-(dimethylamino)-methane using in analogous manner the procedure described in example 45a) to give crude title compound (101 mg) as a red oil which was used directly in the next step. MS ISP (m/e): 214.4 [(M+H)⁺].

b) Methyl 2-[3-methoxy-4-(4-methyl-imidazol-1-yl)-phenylamino]-7,8-dihydro-5H-pyrano[4,3-d]pyrimidine-8-carboxylate The title compound was prepared from crude methyl 5-[1-dimethylamino-methylidene]-4-oxo-tetrahydro-pyran-3-carboxylate (97 mg, 0.45 mmol) and N-[3-methoxy-4-(4-methyl-imidazol-1-yl)-phenyl]-guanidine dinitrate (114 mg, 0.31 mmol) using in analogous manner the procedure described in example 45b). Obtained as a pale-yellow oil (8 mg, 7%). MS ISP (m/e): 396.4 [(M+H)⁺].

Example 59

Ethyl 2-[3-fluoro-4-(4-methyl-imidazol-1-yl)-phenylamino]-5,6,7,8-tetrahydro-quinazoline-8-carboxylate

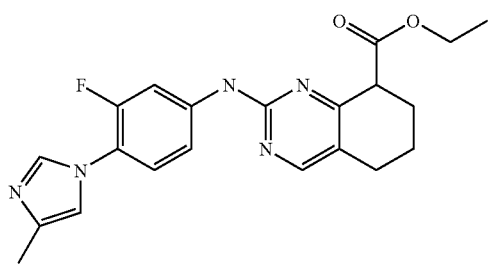

The title compound was prepared from crude ethyl 3-[1-dimethylamino-methylidene]-2-oxo-cyclohexanecarboxylate (165 mg, 0.5 mmol) and N-[3-fluoro-4-(4-methyl-imidazol-1-yl)-phenyl]-guanidine dinitrate (134 mg, 0.37 mmol) using in analogous manner the procedure described in example 45b). Obtained as an off-white solid (27 mg, 18%). MS ISP (m/e): 396.4 [(M+H)$^+$]. mp 142-145° C.

Example 60

[3-Fluoro-4-(4-methyl-imidazol-1-yl)-phenyl]-[8-(4-fluoro-phenyl)-5,6,7,8-tetrahydro-quinazolin-2-yl]-amine

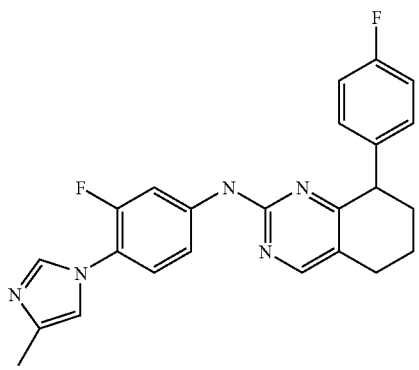

The title compound was prepared from crude 6-[1-dimethylamino-methylidene]-2-(4-fluoro-phenyl)-cyclohexanone (123 mg, ca. 0.5 mmol) and N-[3-methoxy-4-(4-methyl-imidazol-1-yl)-phenyl]-guanidine dinitrate (134 mg, 0.37 mmol) using in analogous manner the procedure described in example 45b). Obtained as a pale-red solid (128 mg, 83%). MS ISP (m/e): 418.3 [(M+H)$^+$]. mp 201-203° C.

Example 61

[8-(3,5-Bis-trifluoromethyl-phenyl)-5,6,7,8-tetrahydro-quinazolin-2-yl]-[3-fluoro-4-(4-methyl-imidazol-1-yl)-phenyl]-amine

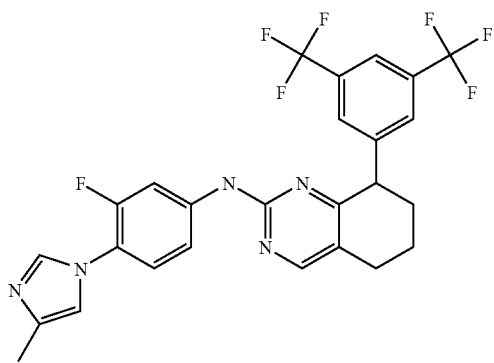

a) 2-(3, 5-Bis-trifluoromethyl-phenyl)-6-[1-dimethylamino-methylidene]-cyclohexanone 2-(3,5-Bis-trifluoromethyl-phenyl)-cyclohexanone (155, 0.5 mmol) was reacted with tert.-butoxy-bis-(dimethylamino)-methane using in analogous manner the procedure described in example 45a) to give crude title compound (184 mg) as a red oil which was used directly in the next step. MS ISP (m/e): 366.1 [(M+H)$^+$].

b) [8-(3,5-Bis-trifluoromethyl-phenyl)-5,6,7,8-tetrahydro-quinazolin-2-yl]-[3-fluoro-4-(4-methyl-imidazol-1-yl)-phenyl]-amine The title compound was prepared from crude 2-(3,5-bis-trifluoromethyl-phenyl)-6-[1-dimethylamino-methylidene]-cyclohexanone (184 mg, 0.5 mmol) and N-[3-methoxy-4-(4-methyl-imidazol-1-yl)-phenyl]-guanidine dinitrate (134 mg, 0.37 mmol) using in analogous manner the procedure described in example 45b). Obtained as a pale-yellow solid (132 mg, 66%). MS ISP (m/e): 536.0 [(M+H)$^+$]. mp 200-202° C.

Example 62

[9-(2,5-Dichloro-phenyl)-6,7,8,9-tetrahydro-5H-cycloheptapyrimidin-2-yl]-[3-methoxy-4-(4-methyl-imidazol-1-yl)-phenyl]-amine

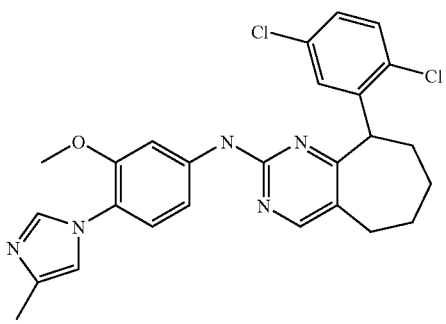

a) 2-(2,5-Dichloro-phenyl)-cycloheptanol 1.6 N Butyllithium-hexane solution (12.5 mL, 20 mmol) was added at −75° C. over 15 min to a solution of 2-bromo-1,4-dichloro-benzene (4.52 g, 20 mmol) in diethyl ether (50 mL). After stirring for 5 min, 8-oxa-bicyclo[5.1.0]octane (2.25 g, 20 mmol) was added, and subsequently, boron trifluoride etherate (2.51 mL, 20 mmol) was added dropwise over 0.5 h to the reaction mixture. Stirring was continued for 0.5 h at −75° C. The temperature was then raised to −30° C. and saturated aqueous ammonium chloride solution was added. After being stirred for 5 min, the mixture was diluted with water. The organic layer was separated, washed with water, and dried over sodium sulfate. Solvents were removed under reduced pressure and the remaining oil was purified by column chromatography on silica gel using heptane/0-20% ethyl acetate as eluent to give the title compound (3.55 g, 68%) as a pale-yellow oil. MS EI (m/e): 258.1 [(M)$^+$].

b) 2-(2,5-Dichloro-phenyl)-cycloheptanone

To a solution of 2-(2,5-dichloro-phenyl)-cycloheptanol (0.6 g, 2.32 mmol) in dichloromethane (40 mL) was added Dess-Martin perjodane (1.22 g, 2.78 mmol). The mixture was stirred at 20° C. for 1 h. A mixture of 10% aq sodium bicarbonate solution (10 mL) and 10% aq sodium thiosulfate solution (10 mL) was added, and stirring was continued for 5 min.

The organic layer was separated and dried over sodium sulfate. Solvents were removed under reduced pressure and the remaining oil was purified by column chromatography on silica gel using heptane/0-20% ethyl acetate as eluent to give the title compound (0.58 g, ca. 100%) as a pale-yellow oil. MS ISP (m/e): 257.1 [(M+H)+].

c) 2-(2,5-Dichloro-phenyl)-7-[1-dimethylamino-methylidene]-cycloheptanone 2-(2,5-Dichloro-phenyl)-cycloheptanone (157 mg, 0.61 mmol) was reacted with tert.-butoxy-bis-(dimethylamino)-methane using in analogous manner the procedure described in example 45a) to give crude title compound (197 mg) as a red solid which was used directly in the next step. MS ISP (m/e): 312.0 [(M+H)+].

d) [9-(2,5-Dichloro-phenyl)-6,7,8,9-tetrahydro-5H-cycloheptapyrimidin-2-yl]-[3-methoxy-4-(4-methyl-imidazol-1-yl)-phenyl]-amine The title compound was prepared from crude ethyl 2-(2,5-dichloro-phenyl)-7-[1-dimethylamino-methylidene]-cycloheptanone (197 mg, ca. 0.61 mmol) and N-[3-methoxy-4-(4-methyl-imidazol-1-yl)-phenyl]-guanidine dinitrate (169 mg, 0.45 mmol) using in analogous manner the procedure described in example 45b). Obtained as a pale-yellow solid (163 mg, 73%). MS ISP (m/e): 494.0 [(M+H)+]. mp 218-220° C.

Example 63

Ethyl 2-[3-methoxy-4-(4-methyl-imidazol-1-yl)-phenylamino]-6,7-dihydro-5H-cyclopentapyrimidine-7-carboxylate

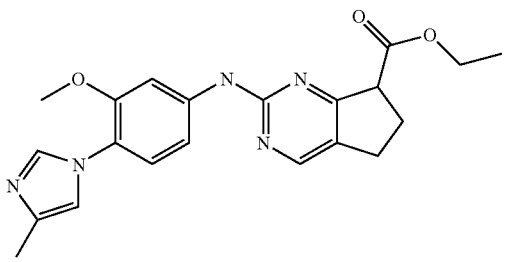

a) Ethyl 3-[1-dimethylamino-methylidene]-2-oxo-cyclopentanecarboxylate

Ethyl 2-oxo-cyclopentanecarboxylicate (48 mg, 0.3 mmol) was reacted with tert.-butoxy-bis-(dimethylamino)-methane using in analogous manner the procedure described in example 45a) to give crude title compound (70 mg) as a pale-yellow oil which was used directly in the next step. MS ISP (m/e): 212.1 [(M+H)+].

b) Ethyl 2-[3-methoxy-4-(4-methyl-imidazol-1-yl)-phenylamino]-6,7-dihydro-5H-cyclopentapyrimidine-7-carboxylate The title compound was prepared from crude ethyl 3-[1-dimethylamino-methylidene]-2-oxo-cyclopentanecarboxylate (70 mg, 0.3 mmol) and N-[3-methoxy-4-(4-methyl-imidazol-1-yl)-phenyl]-guanidine dinitrate (83 mg, 0.22 mmol) using in analogous manner the procedure described in example 45b). Obtained as a pale-yellow solid (5 mg, 6%). MS ISP (m/e): 394.3 [(M+H)+]. mp 150-153° C.

Example 64

[3-Methoxy-4-(4-methyl-imidazol-1-yl)-phenyl]-[8-(3-methyl-[1,2,4]oxadiazol-5-yl)-5,6,7,8-tetrahydro-quinazolin-2-yl]-amine

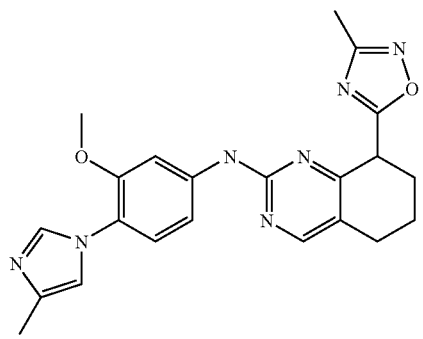

a) 5-(1,4-Dioxa-spiro[4.5]dec-6-yl)-3-methyl-[1,2,4]oxadiazole

A mixture of 1,4-dioxa-spiro[4.5]decane-6-carboxylic acid (3.72 g, 20 mmol), N,N-dicyclohexyl-carbodiimid (2.06 g, 22 mmol) and 1-hydroxy-benzotriazole (3.03 g, 22 mmol) in tetrahydrofuran (40 mL) was stirred at 0° C. for 3.5 h. N-Hydroxy-acetamidine (1.48 g, 20 mmol) was added to the mixture and stirring was continued at 20° C. for 18 h. The reaction mixture was cooled to 0° C. and insoluble material was removed by filtration. The filtrate was evaporated under reduced pressure. Toluene (250 mL) was added to the remaining oil and the mixture was heated at reflux for 5 h, water being removed using a Dean-Stark trap. The solution was cooled, solvents were evaporated under reduced pressure, and the residual material was purified by column chromatography on silica gel (100 g) using heptane/20-80% ethyl acetate as eluent to give the title compound (2.70 g, 60%). Obtained as light-yellow oil. MS ISP (m/e): 225.1 [(M+H)+].

b) 2-(3-Methyl-[1,2,4]oxadiazol-5-yl)-cyclohexanone

A mixture of 5-(1,4-dioxa-spiro[4.5]dec-6-yl)-3-methyl-[1,2,4]oxadiazole (0.67 g, 3.0 mmol), tetrahydrofuran (70 mL), and 3 N hydrochloric acid (35 mL) was stirred at 60° C. for 13 h. The mixture was cooled and extracted with ethyl acetate. The organic layer was successively washed with saturated sodium bicarbonate solution and with brine, dried over sodium sulfate, and evaporated under reduced pressure. The remaining solid was recrystallized from heptane to give the title compound (0.11 g, 20%) as an off-white solid. MS ISP (m/e): 181.1 [(M+H)+]. mp 74-76° C.

c) 2-[1-Dimethylamino-methylidene]-6-(3-methyl-[1,2,4]oxadiazol-5-yl)-cyclohexanone 2-(3-Methyl-[1,2,4]oxadiazol-5-yl)-cyclohexanone (90 mg, 0.5 mmol) was reacted with tert.-butoxy-bis-(dimethylamino)-methane using in analogous manner the procedure described in example 45a) to give crude title compound (123 mg) as a red oil which was used directly in the next step. MS ISP (m/e): 236.1 [(M+H)$^+$].

d) [3-Methoxy-4-(4-methyl-imidazol-1-yl)-phenyl]-[8-(3-methyl-[1,2,4]oxadiazol-5-tetrahydro-quinazolin-2-yl]-amine The title compound was prepared from crude 2-[1-dimethylamino-methylidene]-6-(3-methyl-[1,2,4]oxadiazol-5-yl)-cyclohexanone (123 mg, 0.5 mmol) and N-[3-methoxy-4-(4-methyl-imidazol-1-yl)-phenyl]-guanidine dinitrate (185 mg, 0.5 mmol) using in analogous manner the procedure described in example 45b). Obtained as a pale-yellow solid (96 mg, 62%). MS ISP (m/e): 418.3 [(M+H)$^+$]. mp 212-214° C.

Example 65

Methyl 2-[3-Methoxy-4-(4-methyl-imidazol-1-yl)-phenylamino]-6,7,8,9-tetrahydro-5H-cycloheptapyrimidine-9-carboxylate

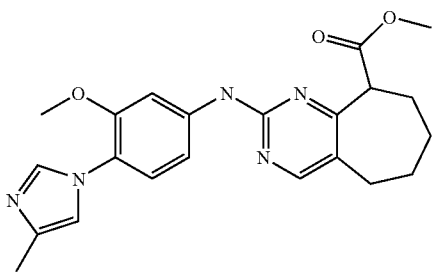

a) Methyl 3-[1-dimethylamino-methylidene]-2-oxo-cycloheptanecarboxylate

Methyl 2-oxo-cycloheptanecarboxylate (51 mg, 0.30 mmol) was reacted with tert.-butoxy-bis-(dimethylamino)-methane using in analogous manner the procedure described in example 45a) to give crude title compound (85 mg) as a yellow oil which was used directly in the next step. MS ISP (m/e): 226.3 [(M+H)$^+$].

b) Methyl 2-[3-Methoxy-4-(4-methyl-imidazol-1-yl)-phenylamino]-6,7,8,9-tetrahydro-5H-cycloheptapyrimidine-9-carboxylate The title compound was prepared from crude methyl 3-[1-dimethylamino-methylidene]-2-oxo-cycloheptanecarboxylate (85 mg, 0.38 mmol) and N-[3-methoxy-4-(4-methyl-imidazol-1-yl)-phenyl]-guanidine dinitrate (83 mg, 0.22 mmol) using in analogous manner the procedure described in example 45b). Obtained as a pale-yellow oil (7 mg, 8%). MS ISP (m/e): 408.5 [(M+H)$^+$].

Example 66

2-(4-Methyl-imidazol-1-yl)-5-(4-phenyl-4,5,6,7-tetrahydro-benzothiazol-2-ylamino)-phenol

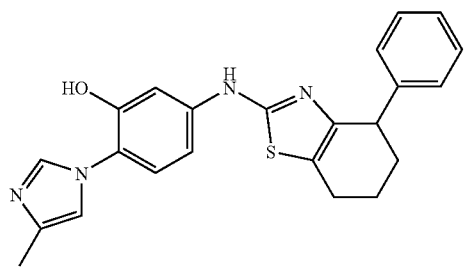

To a suspension of [3-methoxy-4-(4-methyl-imidazol-1-yl)-phenyl]-(4-phenyl-4,5,6,7-tetrahydro-benzothiazol-2-yl)-amine (200 mg, 0.48 mmol) in dichloroethane (4.8 mL) was added under nitrogen at room temperature borontribromide (528 uL, 0.53 mmol) and the reaction was refluxed for 2 hours. The same amount of borontribromide was added and the reaction was refluxed for 2 hours, again the same amount of borontribromide was added and the reaction was refluxed for 1 hour, stirred at room temperature for 3 days. The reaction was set to pH 7 with aqueous sodium hydroxide and extracted three times with ethyl acetate. The combined organic layers were dried over sodium sulfate, filtered and the solvent was removed under reduced pressure. The residue was purified on silica gel using dichloromethane/methanol/concentrated aqueous ammonia (9:1:0.1 v/v/v) as eluent to yield the title compound (70 mg, 36%) as a beige solid. MS ISP (m/e): 403.3 (100) [(M+H)$^+$]. $^1$H NMR (DMSO-D$_6$, 300 MHz): δ (ppm)=10.06 (s, 2H), 7.64 (s, 1H), 7.25-7.31 (m, 2H), 7.17 (t, 1H), 7.00-7.11 (m, 6H), 4.04 (m, 1H), 2.71 (m, 2H), 2.19 (m, 1H), 2.13 (s, 3H), 1.66-1.85 (m, 3H).

Example 67

3-[2-Ethoxy-4-(4-phenyl-4,5,6,7-tetrahydro-benzothiazol-2-ylamino)-phenyl]-1-ethyl-5-methyl-3H-imidazol-1-ium iodide

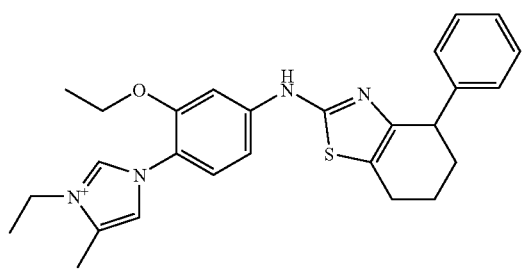

Potassium carbonate (41.5 mg, 0.3 mmol) was added to a solution of 2-(4-methyl-imidazol-1-yl)-5-(4-phenyl-4,5,6,7-tetrahydro-benzothiazol-2-ylamino)-phenol (60.4 mg, 0.15 mmol), iodoethane (15 uL, 0.18 mmol) in acetonitrile (1.5 mL). The reaction was refluxed over night and the solvent was removed under reduced pressure. The residue was purified on silica gel using dichloromethane/methanol/concentrated aqueous ammonia (9:1:0.1 v/v/v) as eluent to yield the title compound (29 mg, 45%) as a beige solid. MS ISP (m/e): 459.4 (100) [(M+H)+]. $^1$H NMR (DMSO-D$_6$, 300 MHz): δ (ppm)=10.39 (s, 1H), 9.31 (s, 1H), 7.83 (s, 1H), 7.67 (s, 1H), 7.34 (d, 1H), 7.29 (t, 2H), 7.14-7.21 (m, 3H), 6.82 (d, 1H), 4.18 (q, 2H), 3.99 (m, 1H), 3.59 (dq, 1H), 3.50 (dq, 1H), 2.64-2.82 (m, 2H), 2.34 (s, 3H), 2.17 (m, 1H), 1.90 (m, 1H), 1.76 (m, 2H), 1.43 (t, 3H), 1.14 (t, 3H).

Example 68

[4-(2-Methyl-oxazol-5-yl)-phenyl]-(4-phenyl-4,5,6,7-tetrahydro-benzothiazol-2-yl)-amine

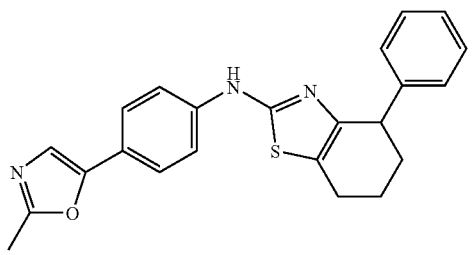

a) [4-(2-Methyl-oxazol-5-yl)-phenyl]-thiourea

To a solution of 4-(2-methyl-oxazol-5-yl)phenylamine (470 mg, 2.7 mmol, CAS 89260-50-4) in tetrahydrofurane (6 mL) was added drop wise under benzoyl isothiocyanate (402 uL, 2.8 mmol). The reaction was stirred at room temperature for 3 hours. The solvent was removed under reduced pressure. The residue was dissolved in methanol (7 mL) and a solution of potassium carbonate (1119 mg, 8.1 mmol) in water (3.6 mL) was added. A solid precipitated and the reaction was stirred over night at room temperature. The solvent was removed under reduced pressure. The residue was dissolved in methanol (20 mL), tetrahydrofurane (10 mL) and 1M aqueous sodium hydroxide solution (8.1 mL). The reaction was stirred over night at room temperature, diluted with water and extracted three times with methylene chloride. The combined organic layers were dried over sodium sulfate, filtered and the solvent was removed under reduced pressure. The residue was suspended in water and extracted three times with methylene chloride. The combined organic layers were washed with brine, dried over sodium sulfate, filtered and the solvent was removed under reduced pressure. The residue was purified on silica gel using methylene chloride and methylene chloride/methanol (19:1 v/v) as eluent to yield the title compound (105 mg, 17%) as a light brown solid. MS ISP (m/e): 234.2 (100) [(M+H)+]. $^1$H NMR (DMSO-D$_6$, 300 MHz): δ (ppm)=9.79 (s, 1H), 7.59 (d, 1H), 7.52 (d, 2H), 7.45 (s, 1H), 2.47 (s, 3H).

b) [4-(2-Methyl-oxazol-5-yl)-phenyl]-(4-phenyl-4,5,6,7-tetrahydro-benzothiazol-2-yl)-amine A solution of [4-(2-methyl-oxazol-5-yl)-phenyl]-thiourea (100 mg, 0.43 mmol) and 2-bromo-6-phenyl-cyclohexanone (114 mg, 0.45 mmol) in ethanol (5 mL) was heated to reflux over night. The solvent was removed under reduced pressure and the residue purified on silica gel using methylene chloride and methylene chloride/methanol (19:1 v/v) as eluent to yield the title compound (73 mg, 44%) as a yellow gum. MS ISP (m/e): 388.2 (100%) [(M+H)+]. $^1$H NMR (DMSO-D$_6$, 300 MHz): δ (ppm)=10.18 (s, 1H), 7.49 (m, 4H), 7.11-7.29 (m, 6H), 4.04 (m, 1H), 2.70 (m, 2H), 2.43 (s, 3H), 2.14 (m, 1H), 1.70-1.93 (m, 3H).

Example 69

[3-Methoxy-4-(4-methyl-imidazol-1-yl)-phenyl]-[8-(3,4,5-trifluoro-phenyl)-5,6,7,8-tetrahydro-quinazolin-2-yl]-amine

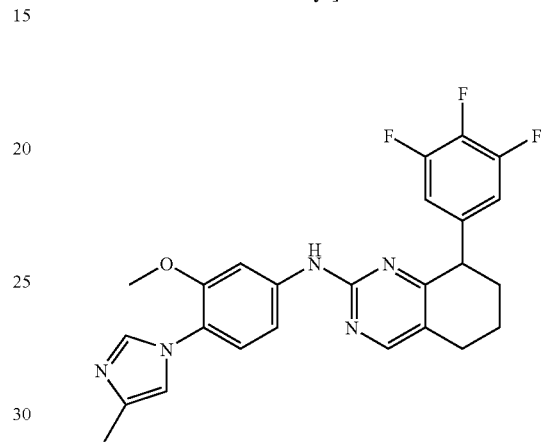

a) 2-(3,4,5-Trifluoro-phenyl)-cyclohexanol

To a solution of 1-bromo-3,4,5-trifluorobenzene (480 mg, 2.2 mmol) in diethyl ether (4.5 mL) was added drop wise at −76° C. under nitrogen butyl lithium (1.6 M in hexane, 1.31 mL, 2.1 mmol) keeping the temperature below −69° C. After 5 minutes cyclohexene oxide (216 uL, 2.1 mmol) was added dropwise keeping the temperature below −73° C. and then boron trifluoro etheroate (268 uL, 1.0 mmol) keeping the temperature below −66° C. The reaction was stirred for 30 minutes at −58° C. and then for 30 minutes at room temperature. Saturated aqueous ammonium chloride solution was added and the reaction was extracted twice with diethyl ether. The combined organic layers were washed with brine, dried over sodium sulfate, filtered and the solvent was removed under reduced pressure. The residue was purified on silica gel using heptane/ethyl acetate (7:3 v/v) as eluent to yield the title compound (221 mg, 43%) as an off-white solid. $^1$H NMR (CDCl$_3$, 300 MHz): δ (ppm)=6.83-6.91 (m, 2H), 3.57 (m, 1H), 2.37 (m, 1H), 2.10 (m, 1H), 1.75-1.86 (m, 3H), 1.26-1.56 (m, 5H).

b) 2-(3,4,5-Trifluoro-phenyl)-cyclohexanone

To a solution of 2-(3,4,5-trifluoro-phenyl)-cyclohexanol (215 mg, 0.93 mmol) dissolved in methylene chloride (15 mL) was added under nitrogen Dess-Martin reagent (475 mg, 1.1 mmol, 15 weight-percent in methylene chloride). The reaction was stirred at room temperature over night. The same amount of Des-Martin reagent was added and the reaction was stirred at room temperature over night. The reaction was poured onto a saturated sodium bicarbonate solution. The organic layer was washed with 10% aqueous sodium thiosulfate solution and brine, dried over sodium sulfate, filtered and the solvent was removed under reduced pressure. The residue was stirred with heptane/ethyl acetate (7:3 v/v) and the solid was filtered off to yield the title compound (202 mg, 95%) as a yellow solid. $^1$H NMR (CDCl$_3$, 300 MHz): δ (ppm)=7.10-7.20 (m, 2H), 3.84 (dd, 1H), 2.28-2.33 (m, 2H), 1.65-2.12 (m, 6H).

c) 2-[1-Dimethylamino-meth-(Z)-ylidene]-6-(3,4,5-trifluoro-phenyl)-cyclohexanone 2-(3,4,5-Trifluoro-phenyl)-cyclohexanone (100 mg, 0.44 mmol) was reacted with tert.-butoxy-bis-(dimethylamino)-methane using in analogous manner the procedure described in example 45a) to give crude title compound (123 mg) as a brown oil which was used directly in the next step. MS ISP (m/e): 284.2 (100) [(M+H)$^+$].

d) [3-Methoxy-4-(4-methyl-imidazol-1-yl)-phenyl]-[8-(3,4,5-trifluoro-phenyl)-5,6,7,8-tetrahydro-quinazolin-2-yl]-amine The title compound was prepared from crude 2-[1-dimethylamino-meth-(Z)-ylidene]-6-(3,4,5-trifluoro-phenyl)-cyclohexanone (120 mg, 0.42 mmol) and N-[3-methoxy-4-(4-methyl-imidazol-1-yl)-phenyl]-guanidine dinitrate (131 mg, 0.35 mmol) using in analogous manner the procedure described in example 45b). Obtained as a yellow solid (64 mg, 64%). MS ISP (m/e): 466.2 (100) [(M+H)$^+$]. $^1$H NMR (DMSO-D$_6$, 300 MHz): δ (ppm)=9.57 (s, 1H), 8.36 (s, 1H), 7.60 (m, 2H), 7.01-7.18 (m, 4H), 6.98 (s, 1H), 4.18 (m, 1H), 3.55 (s, 3H), 2.73 (m, 2H), 2.13 (s, 3H), 1.70-2.20 (m, 4H).

Example 70

(8-tert-Butyl-5,6,7,8-tetrahydro-quinazolin-2-yl)-[3-methoxy-4-(4-methyl-imidazol-1-yl)-phenyl]-amine

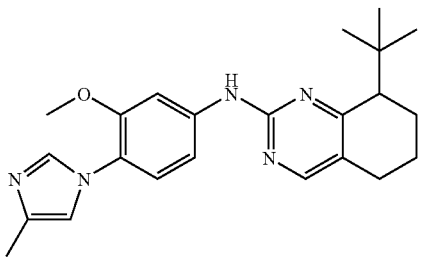

a) 2-tert-Butyl-6-[1-dimethylamino-meth-(E)-ylidene]-cyclohexanone 2-tert-Butylcyclohexanone (93 mg, 0.60 mmol) was reacted with tert.-butoxy-bis-(dimethylamino)-methane using in analogous manner the procedure described in example 45a) to give crude title compound (105 mg) as a yellow oil which was used directly in the next step. MS ISP (m/e): 210.2 (100) [(M+H)$^+$].

b) (8-tert-Butyl-5,6,7,8-tetrahydro-quinazolin-2-yl)-[3-methoxy-4-(4-methyl-imidazol-1-yl)-phenyl]-amine The title compound was prepared from crude 2-tert-butyl-6-[1-dimethylamino-meth-(E)-ylidene]-cyclohexanone (100 mg, 0.48 mmol) and N-[3-methoxy-4-(4-methyl-imidazol-1-yl)-phenyl]-guanidine dinitrate (111 mg, 0.30 mmol) using in analogous manner the procedure described in example 45b). Obtained as a yellow solid (59 mg, 50%). MS ISP (m/e): 392.3 (100) [(M+H)$^+$]. $^1$H NMR (DMSO-D$_6$, 300 MHz): δ (ppm)=9.43 (s, 1H), 8.22 (s, 1H), 7.76 (s, 1H), 7.64 (s, 1H), 7.43 (d, 1H), 7.19 (d, 1H), 7.02 (s, 1H), 3.78 (s, 3H), 2.51-2.65 (m, 2H), 2.14 (s, 3H), 1.91 (m, 2H), 1.73 (m, 1H), 1.40 (m, 1H), 1.03 (s, 9H).

Example 71

(8-Cyclohexyl-5,6,7,8-tetrahydro-quinazolin-2-yl)-[3-methoxy-4-(4-methyl-imidazol-1-yl)-phenyl]-amine

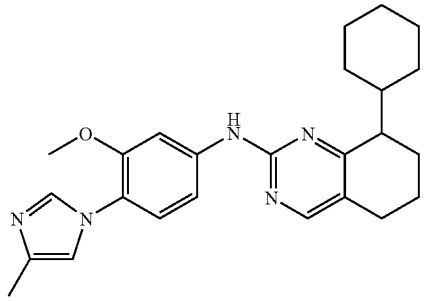

a) 3-[1-Dimethylamino-meth-(E)-ylidene]-bicyclohexyl-2-one

2-Cyclohexylcyclohexanone (99 mg, 0.55 mmol) was reacted with tert.-butoxy-bis-(dimethylamino)-methane using in analogous manner the procedure described in example 45a) to give crude title compound (116 mg) as a brown solid which was used directly in the next step. MS ISP (m/e): 236.2 (100) [(M+H)$^+$].

b) (8-Cyclohexyl-5,6,7,8-tetrahydro-quinazolin-2-yl)-[3-methoxy-4-(4-methyl-imidazol-1-yl)-phenyl]-amine The title compound was prepared from crude 3-[1-dimethylamino-meth-(E)-ylidene]-bicyclohexyl-2-one (84 mg, 0.36 mmol) and N-[3-methoxy-4-(4-methyl-imidazol-1-yl)-phenyl]-guanidine dinitrate (111 mg, 0.30 mmol) using in analogous manner the procedure described in example 45b). Obtained as yellow crystals (61 mg, 49%). MS ISP (m/e): 418.3 (100) [(M+H)$^+$]. $^1$H NMR (DMSO-D$_6$, 300 MHz): δ (ppm)=9.57 (s, 1H), 8.21 (s, 1H), 7.90 (s, 1H), 7.65 (s, 1H), 7.39 (d, 1H), 7.21 (d, 1H), 7.03 (s, 1H), 3.82 (s, 3H), 2.51-2.65 (m, 2H), 2.14 (s, 3H), 1.72-1.94 (m, 3H), 1.52-1.70 (m, 5H), 1.02-1.35 (m, 7H).

Example 72

[8-(3-Chloro-benzenesulfonyl)-5,6,7,8-tetrahydro-quinazolin-2-yl]-[3-methoxy-4-(4-methyl-imidazol-1-yl)-phenyl]-amine

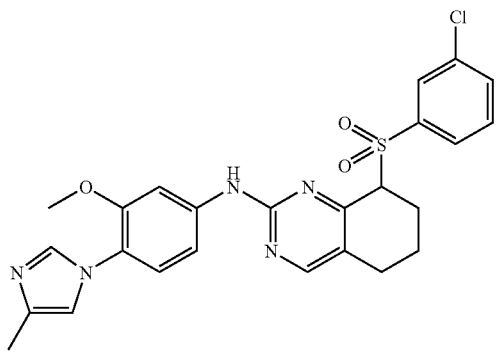

a) 2-(3-Chloro-benzenesulfonyl)-6-[1-dimethylamino-meth-(E)-ylidene]-cyclohexanone 2-(3-Chloro-benzenesulfonyl)-cyclohexanone (98 mg, 0.36 mmol, obtained by oxidation of the corresponding sulfide (CAS 1044049-34-4) with 2.2 eq MCPBA in dichloromethane at room temperature) was reacted with tert.-butoxy-bis-(dimethylamino)-methane using in analogous manner the procedure described in example 45a) to give crude title compound (111 mg) as a brown solid which was used directly in the next step. MS ISP (m/e): 328.2/330.2 (100/52) [(M+H)$^+$].

b) [8-(3-Chloro-benzenesulfonyl)-5,6,7,8-tetrahydro-quinazolin-2-yl]-[3-methoxy-4-(4-methyl-imidazol-1-yl)-phenyl]-amine The title compound was prepared from crude 2-(3-chloro-benzenesulfonyl)-6-[1-dimethylamino-meth-(E)-ylidene]-cyclohexanone (108 mg, 0.33 mmol) and N-[3-methoxy-4-(4-methyl-imidazol-1-yl)-phenyl]-guanidine dinitrate (111 mg, 0.30 mmol) using in analogous manner the procedure described in example 45b). Obtained as a yellow solid (46 mg, 30%). MS ISP (m/e): 510.3/512.2 (100/39) [(M+H)$^+$]. $^1$H NMR (DMSO-D$_6$, 300 MHz): δ (ppm)=9.59 (s, 1H), 8.39 (s, 1H), 7.66-7.70 (m, 3H), 7.58 (d, 1H), 7.47-7.52 (m, 2H), 7.02-7.04 (m, 2H), 6.96 (d, 1H), 4.89 (m, 1H), 3.68 (s, 3H), 2.51-2.65 (m, 2H), 2.16 (s, 3H), 2.00-2.16 (m, 3H), 1.76 (m, 1H).

Example 73

{2-[3-Methoxy-4-(4-methyl-imidazol-1-yl)-phenylamino]-5,6,7,8-tetrahydro-quinazolin-8-yl}-acetic acid ethyl ester

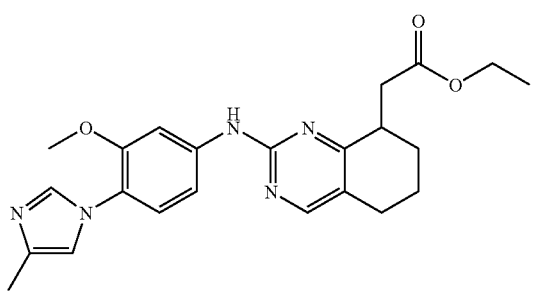

a) {3-[1-Dimethylamino-meth-(E)-ylidene]-2-oxo-cyclohexyl}-acetic acid ethyl ester Ethyl 2-cyclohexanoneacetate (100 mg, 0.54 mmol) was reacted with tert.-butoxy-bis-(dimethylamino)-methane using in analogous manner the procedure described in example 45a) to give crude title compound (116 mg) as a brown oil which was used directly in the next step. MS ISP (m/e): 194.2 (100) [(M-EtOH+H)$^+$], 240.2 (90) [(M+H)$^+$].

b) {2-[3-Methoxy-4-(4-methyl-imidazol-1-yl)-phenylamino]-5,6,7,8-tetrahydro-quinazolin-8-yl}-acetic acid ethyl ester The title compound was prepared from crude {3-[1-dimethylamino-meth-(E)-ylidene]-2-oxo-cyclohexyl}-acetic acid ethyl ester (108 mg, 0.33 mmol) and N-[3-methoxy-4-(4-methyl-imidazol-1-yl)-phenyl]-guanidine dinitrate (111 mg, 0.30 mmol) using in analogous manner the procedure described in example 45b). Obtained as yellow crystals (83 mg, 66%). MS ISP (m/e): 422.2 (100) [(M+H)$^+$]. $^1$H NMR (DMSO-D$_6$, 300 MHz): δ (ppm)=9.60 (s, 1H), 8.25 (s, 1H), 7.88 (s, 1H), 7.65 (s, 1H), 7.27 (d, 1H), 7.20 (d, 1H), 7.02 (s, 1H), 4.06 (q, 2H), 3.79 (s, 3H), 3.10 (m, 2H), 2.60-2.70 (m, 3H), 2.14 (s, 3H), 2.02 (m, 1H), 1.86 (m, 1H), 1.65 (m, 2H), 1.15 (t, 3H).

Example 74

[8-(tert-Butyl-dimethyl-silanyloxy)-5,6,7,8-tetrahydro-quinazolin-2-yl]-[3-methoxy-4-(4-methyl-imidazol-1-yl)-phenyl]-amine

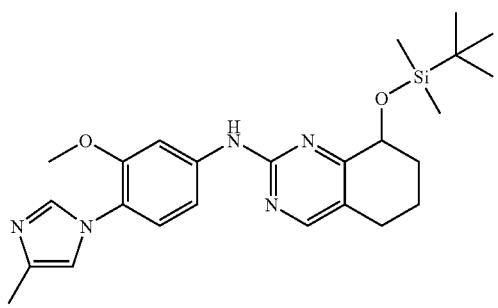

a) 2-(tert-Butyl-dimethyl-silanyloxy)-6-[1-dimethylamino-meth-(E)-ylidene]-cyclohexanone 2-(tert.-Butyldimethylsiloxy)cyclohexanone (118 mg, 0.50 mmol) was reacted with tert.-butoxy-bis-(dimethylamino)-methane using in analogous manner the procedure described in example 45a) to give crude title compound (85 mg) as a brown oil which was used directly in the next step. MS ISP (m/e): 284.2 (100) [(M+H)$^+$].

b) [8-(tert-Butyl-dimethyl-silanyloxy)-5,6,7,8-tetrahydro-quinazolin-2-yl]-[3-methoxy-4-(4-methyl-imidazol-1-yl)-phenyl]-amine The title compound was prepared from crude 2-(tert-butyl-dimethyl-silanyloxy)-6-[1-dimethylamino-meth-(E)-ylidene]-cyclohexanone (80 mg, 0.28 mmol) and N-[3-methoxy-4-(4-methyl-imidazol-1-yl)-phenyl]-guanidine dinitrate (74 mg, 0.20 mmol) using in analogous manner the procedure described in example 45b). Obtained as an orange gum (27 mg, 29%). MS ISP (m/e): 466.3 (100) [(M+H)+]. $^1$H NMR (DMSO-D$_6$, 300 MHz): δ (ppm)=9.49 (s, 1H), 8.32 (s, 1H), 7.72 (d, 1H), 7.65 (s, 1H), 7.54 (s, 1H), 7.18 (d, 1H), 7.02 (s, 1H), 4.60 (m, 1H), 3.78 (s, 3H), 2.60-2.70 (m, 1H), 2.14 (s, 3H), 1.86 (m, 3H), 1.72 (m, 1H), 0.85 (s, 9H), 0.20 (s, 3H), 0.05 (s, 3H).

Example 75

2-[3-Methoxy-4-(4-methyl-imidazol-1-yl)-phenylamino]-8-pyridin-3-yl-5,6,7,8-tetrahydro-quinazolin-8-ol

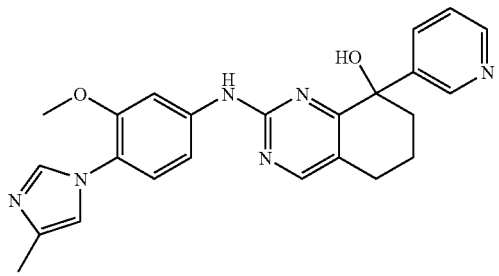

a) 6-[1-Dimethylamino-meth-(E)-ylidene]-2-hydroxy-2-pyridin-3-yl-cyclohexanone 2-Hydroxy-2-pyridin-3yl-cyclohexanone (394 mg, 2 mmol) was reacted with tert.-butoxy-bis-(dimethylamino)-methane using in analogous manner the procedure described in example 45a) to give crude title compound (582 mg) as a brown oil which was used directly in the next step. MS ISP (m/e): 247.2 (100) [(M+H)+].

b) 2-[3-Methoxy-4-(4-methyl-imidazol-1-yl)-phenylamino]-8-pyridin-3-yl-5,6,7,8-tetrahydro-quinazolin-8-ol The title compound was prepared from crude 6-[1-dimethylamino-meth-(E)-ylidene]-2-hydroxy-2-pyridin-3-yl-cyclohexanone (59 mg, 0.24 mmol) and N-[3-methoxy-4-(4-methyl-imidazol-1-yl)-phenyl]-guanidine dinitrate (74 mg, 0.20 mmol) using in analogous manner the procedure described in example 45b). Obtained as a yellow solid (54 mg, 63%). MS ISP (m/e): 429.3 (100) [(M+H)+]. $^1$H NMR (DMSO-D$_6$, 300 MHz): δ (ppm)=9.63 (s, 1H), 8.51 (s, 1H), 8.42 (m, 2H), 7.72 (s, 1H), 7.68 (d, 1H), 7.62 (s, 1H), 7.33 (dd, 1H), 7.04 (s, 2H), 6.97 (s, 1H), 5.95 (s, 1H), 5.76 (s, 1H), 3.39 (s, 3H), 2.75 (m, 3H), 2.12 (s, 3H), 2.02 (m, 3H), 1.75 (m, 1H).

Example 76

Methanesulfonic acid 2-[3-methoxy-4-(4-methyl-imidazol-1-yl)-phenylamino]-5,6,7,8-tetrahydro-quinazolin-8-yl ester

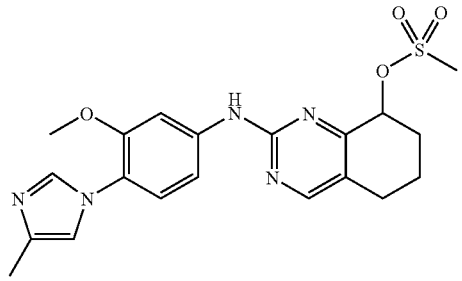

a) 2-[3-Methoxy-4-(4-methyl-imidazol-1-yl)-phenylamino]-5,6,7,8-tetrahydro-quinazolin-8-ol A solution of crude 6-[1-dimethylamino-meth-(E)-ylidene]-2-hydroxy-2-pyridin-3-yl-cyclohexanone (1002 mg, 2.7 mmol), N-[3-methoxy-4-(4-methyl-imidazol-1-yl)-phenyl]-guanidine dinitrate (948 mg, 3.3 mmol) and triethyl amine (546 mg, 5.4 mmol) in ethanol (13.5 mL) was heated to 160° C. for 30 minutes in a microwave oven. The reaction was concentrated under reduced pressure. The residue was partitioned between water and ethyl acetate. The aqueous layer was extracted twice with ethyl acetate. The combined organic layers were washed with water and brine, dried over sodium sulfate, filtered and the solvent was removed under reduced pressure to yield 1340 mg of crude intermediate. This was dissolve in tetrahydrofuran (13.5 mL) and under nitrogen 1M TBAF solution in tetrahydrofuran (4.0 mL) was added. The reaction was stirred at room temperature over night and was concentrated under reduced pressure. The residue was partitioned between water and ethyl acetate. The aqueous layer was extracted twice with ethyl acetate. The combined organic layers were washed with brine, dried over sodium sulfate, filtered and the solvent was removed under reduced pressure. The residue was purified on silica gel using dichloromethane/methanol (9:1 v/v) as eluent to yield the title compound (765 mg, 81%) as a brown foam. MS ISP (m/e): 352.3 (100) [(M+H)+]. $^1$H NMR (DMSO-D$_6$, 300 MHz): δ (ppm)=9.67 (s, 1H), 8.30 (s, 1H), 7.98 (s, 1H), 7.65 (s, 1H), 7.38 (d, 1H), 7.20 (d, 1H), 7.03 (s, 1H), 5.24 (d, 1H), 4.44 (m, 1H), 3.79 (s, 3H), 2.55-2.65 (m, 2H), 2.14 (s, 3H), 1.65-1.95 (m, 4H).

b) Methanesulfonic acid 2-[3-methoxy-4-(4-methyl-imidazol-1-yl)-phenylamino]-5,6,7,8-tetrahydro-quinazolin-8-yl ester To a solution of 2-[3-methoxy-4-(4-methyl-imidazol-1-yl)-phenylamino]-5,6,7,8-tetrahydro-quinazolin-8-ol (105 mg, 0.3 mmol) dissolved in methylene chloride (3 mL) was added under nitrogen at 0° C. triethyl amine (35 mg, 0.36 mmol) und mesylchloride (39 mg, 0.33 mmol). The solution was stirred at room temperature over night. The reaction was diluted with methylene chloride, washed with water and brine, dried over sodium sulfate, filtered and the solvent was removed under reduced pressure. The residue was purified on silica gel using dichloromethane/methanol (19:1 v/v) as eluent to yield the title compound (69 mg, 54%) as a yellow foam. MS ISP (m/e): 430.3 (100) [(M+H)+], 334.3 (25) [(M-MesOH+H)+]. ¹H NMR (DMSO-D₆, 300 MHz): δ (ppm)=9.74 (s, 1H), 8.45 (s, 1H), 7.69 (s, 1H), 7.66 (s, 1H), 7.48 (d, 1H), 7.21 (d, 1H), 7.04 (s, 1H), 5.57 (t, 1H), 3.80 (s, 3H), 3.32 (s, 3H), 3.30 (m, 1H), 2.51-2.78 (m, 2H), 2.14 (s, 3H), 2.14 (m, 1H), 1.72 (m, 3H).

Example 77

[3-Methoxy-4-(4-methyl-imidazol-1-yl)-phenyl]-(8-pyrrolidin-1-yl-5,6,7,8-tetrahydro-quinazolin-2-yl)-amine

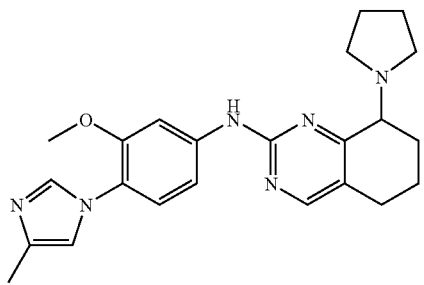

To a suspension of methanesulfonic acid 2-[3-methoxy-4-(4-methyl-imidazol-1-yl)-phenylamino]-5,6,7,8-tetrahydro-quinazolin-8-yl ester (61 mg, 0.14 mmol) in tetrahydrofurane (1.4 mL) was added under nitrogen at 0° C. pyrrolidine (20 mg, 0.28 mmol) and triethyl amine (29 mg, 0.28 mmol). The reaction was stirred at room temperature over night, heated to reflux for 2 hours. A few drops of dimethylformamide were added and the reaction was stirred at room temperature for 2 hours. The reaction was concentrated under reduced pressure, dissolved in water and extracted twice with ethyl acetate. The combined organic layers were washed with dried over sodium sulfate, filtered and the solvent was removed under reduced pressure. The residue was purified on silica gel using dichloromethane/methanol/concentrated aqueous ammonia (19:1:0.2 v/v/v) as eluent to yield the title compound (24 mg, 42%) as a yellow solid. MS ISP (m/e): 234.3 (100), 334 (24), 405.3 (69) [(M+H)+]. ¹H NMR (DMSO-D₆, 300 MHz): δ (ppm)=9.61 (s, 1H), 8.29 (s, 1H), 7.95 (s, 1H), 7.64 (s, 1H), 7.38 (d, 1H), 7.20 (d, 1H), 7.02 (s, 1H), 3.80 (s, 3H), 2.55-2.80 (m, 4H), 2.14 (s, 3H), 2.04 (m, 2H), 1.60-1.80 (m, 6H).

Example 78

[3-Methoxy-4-(4-methyl-imidazol-1-yl)-phenyl]-(8-methoxy-5,6,7,8-tetrahydro-quinazolin-2-yl)-amine formiate

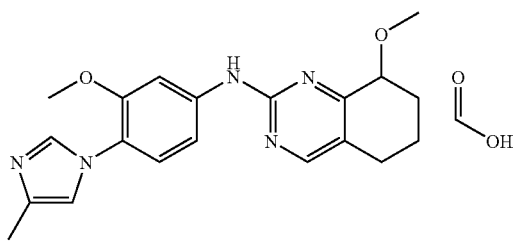

To a solution of methanesulfonic acid 2-[3-methoxy-4-(4-methyl-imidazol-1-yl)-phenylamino]-5,6,7,8-tetrahydro-quinazolin-8-yl ester (86 mg, 0.2 mmol) in methanol (2 mL) was added sodium ethanolate (17 mg, 0.3 mmol). The reaction was stirred at room temperature over night under nitrogen, heated to reflux for 1 hour. The reaction was diluted with water and extracted twice with ethyl acetate. The combined organic layers were washed with dried over sodium sulfate, filtered and the solvent was removed under reduced pressure. The residue was purified by reversed phase preparative HPLC using a mixture of water containing formic acid and acetonitrile to yield the title compound (23 mg, 28%) as a yellow gum. MS ISP (m/e): 366.2 (100) [(M+H)+]. ¹H NMR (CDCl₃, 300 MHz): δ (ppm)=8.35 (s, 1H), 8.26 (s, 1H), 7.85 (d, 1H), 7.75 (s, 1H), 7.16 (d, 1H), 7.09 (d, 1H), 6.88 (s, 1H), 4.19 (t, 1H), 3.88 (s, 3H), 3.58 (s, 3H), 2.55-2.80 (m, 2H), 2.33 (s, 3H), 2.15 (m, 1H), 1.72-2.05 (m, 3H).

Example 79

[3-Methoxy-4-(4-methyl-imidazol-1-yl)-phenyl]-(8-piperidin-1-yl-5,6,7,8-tetrahydro-quinazolin-2-yl)-amine

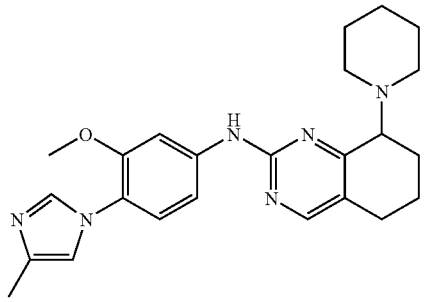

To a suspension of methanesulfonic acid 2-[3-methoxy-4-(4-methyl-imidazol-1-yl)-phenylamino]-5,6,7,8-tetrahydro-quinazolin-8-yl ester (76 mg, 0.18 mmol) in dimethylformamide (2 mL) was added under nitrogen at 0° C. piperidine (30 mg, 0.35 mmol) and triethyl amine (36 mg, 0.35 mmol). The reaction was stirred at room temperature over night. Piperidine (30 mg, 0.35 mmol) was added and the reaction stirred at room temperature for 3 hours. The reaction was diluted with water and extracted twice with diethyl ether. The combined organic layers were washed with dried over sodium sulfate, filtered and the solvent was removed under reduced pressure. The residue was purified on silica gel using dichloromethane/methanol/concentrated aqueous ammonia (19:1:0.2 v/v/v) as eluent to yield the title compound (13 mg, 18%) as an orange solid. MS ISP (m/e): 334.3 (27), 419.3 (100) [(M+H)+]. ¹H NMR (DMSO-D₆, 300 MHz): δ (ppm)=9.60 (s, 1H), 8.26 (s, 1H), 7.82 (s, 1H), 7.65 (s, 1H), 7.60 (d, 1H), 7.19 (d, 1H), 7.03 (s, 1H), 3.80 (s, 3H), 3.63 (m, 1H), 3.05 (m, 1H), 2.55-2.80 (m, 2H), 2.25 (m, 2H), 2.14 (s, 3H), 1.89 (m, 2H), 1.38-1.68 (m, 8H).

Example 80

(6-Isopropyl-8-phenyl-5,6,7,8-tetrahydro-pyrido[4,3-#d!]pyrimidin-2-yl)-[3-methoxy-4-(4-methyl-imidazol-1-yl)-phenyl]-amine

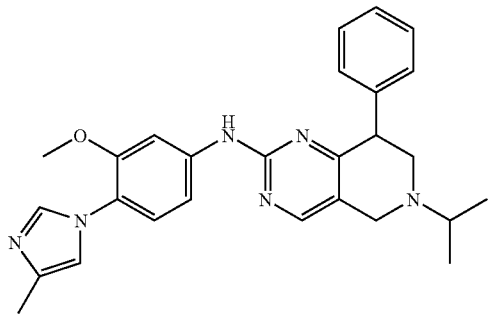

To a solution of [3-methoxy-4-(4-methyl-imidazol-1-yl)-phenyl]-(8-phenyl-5,6,7,8-tetrahydro-pyrido[4,3-d]pyrimidin-2-yl)-amine hydrogen chloride (75 mg, 0.17 mmol) in tetrahydrofurane (3.3 mL) was added ethyldiisopropyl amine (57 uL, 0.33 mmol). The reaction was stirred for 45 minutes at room temperature. Acetone (14 uL, 0.19 mmol), acetic acid (19 uL, 0.33 mmol) and sodium triacetoxyborohydride (106 mg, 0.5 mmol) were added and the reaction was stirred at room temperature over night. The solvent was removed under reduced pressure. The residue was purified on silica gel using dichloromethane/methanol/concentrated aqueous ammonia (9:1:0.1 v/v/v) as eluent to yield the title compound (32 mg, 42%) as a beige gum. MS ISP (m/e): 455.3 (100) [(M+H)$^+$]. $^1$H NMR (CDCl$_3$, 300 MHz): δ (ppm)=8.24 (s, 1H), 7.63 (s, 1H), 7.55 (s, 1H), 7.21-7.33 (m, 5H), 7.12 (d, 1H), 6.79 (s, 1H), 6.69 (d, 1H), 4.20 (m, 1H), 3.75 (dd, 2H), 3.34 (s, 3H), 3.19 (dd, 1H), 2.98 (sept, 1H), 2.69 (dd, 1H), 2.27 (s, 3H), 1.12 (d, 3H), 1.08 (d, 3H).

Example 81

[3-Methoxy-4-(4-methyl-imidazol-1-yl)-phenyl]-(8-morpholin-4-yl-5,6,7,8-tetrahydro-quinazolin-2-yl)-amine

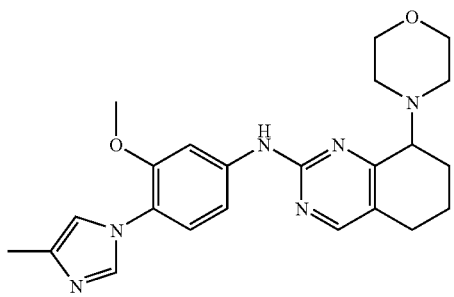

a) 2-[1-Dimethylamino-methylidene]-6-morpholin-4-yl-cyclohexanone

2-Morpholin-4-yl-cyclohexanone (183 mg, 1.0 mmol) was reacted with tert.-butoxy-bis-(dimethylamino)-methane using in analogous manner the procedure described in example 45a) to give crude title compound (260 mg) as a yellow oil which was used directly in the next step.

b) 3-Methoxy-4-(4-methyl-imidazol-1-yl)-phenyl]-(8-morpholin-4-yl-5,6,7,8-tetrahydro-quinazolin-2-yl)-amine The title compound was prepared from 2-[1-dimethylamino-methylidene]-6-morpholin-4-yl-cyclohexanone (260 mg, 1.0 mmol) and N-[3-methoxy-4-(4-methyl-imidazol-1-yl)-phenyl]-guanidine dinitrate (223 mg, 0.60 mmol) using in analogous manner the procedure described in example 45b). Obtained as a white solid (38 mg, 15%). MS ISP (m/e): 421.1 (100) [(M+H)$^+$]. mp 214-216° C.

Example 82

2-[3-Methoxy-4-(4-methyl-imidazol-1-yl)-phenylamino]-5,6,7,8-tetrahydro-quinazolin-8-ol

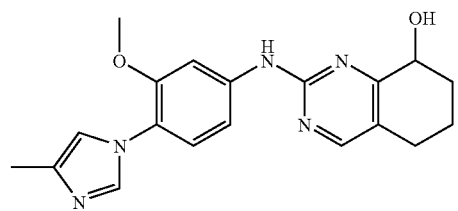

a) 2-[1-Dimethylamino-methylidene]-6-hydroxy-cyclohexanone

2-Hydroxy-cyclohexanone (114 mg, 1.0 mmol) was reacted with tert.-butoxy-bis-(dimethylamino)-methane using in analogous manner the procedure described in example 45a) to give crude title compound (188 mg) as a yellow oil which was used directly in the next step.

b) 2-[3-Methoxy-4-(4-methyl-imidazol-1-yl)-phenylamino]-5,6,7,8-tetrahydro-quinazolin-8-ol The title compound was prepared from 2-[1-dimethylamino-methylidene]-6-hydroxy-cyclohexanone (188 mg, 1 mmol) and N-[3-methoxy-4-(4-methyl-imidazol-1-yl)-phenyl]-guanidine dinitrate (223 mg, 0.60 mmol) using in analogous manner the procedure described in example 45b). Obtained as a white solid (36 mg, 17%). MS ISP (m/e): 352.3 (100) [(M+H)$^+$].

Example 83

(8-Ethoxy-5,6,7,8-tetrahydro-quinazolin-2-yl)-[3-methoxy-4-(4-methyl-imidazol-1-yl)-phenyl]-amine

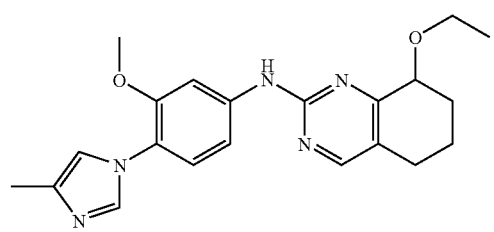

a) 2-[1-Dimethylamino-methylidene]-6-ethoxy-cyclohexanone

2-Ethoxy-cyclohexanone (142 mg, 1.0 mmol) was reacted with tert.-butoxy-bis-(dimethylamino)-methane using in analogous manner the procedure described in example 45a) to give crude title compound (232 mg) as a yellow oil which was used directly in the next step.

b) (8-Ethoxy-5,6,7,8-tetrahydro-quinazolin-2-yl)-[3-methoxy-4-(4-methyl-imidazol-1-yl)-phenyl]-amine The title compound was prepared from 2-[1-dimethylamino-methylidene]-6-ethoxy-cyclohexanone (232 mg, 1.0 mmol) and N-[3-methoxy-4-(4-methyl-imidazol-1-yl)-phenyl]-guanidine dinitrate (223 mg, 0.60 mmol) using in analogous manner the procedure described in example 45b). Obtained as a white solid (50 mg, 22%). MS ISP (m/e): 380.4 (100) [(M+H)$^+$].

Example 84

[3-Methoxy-4-(4-methyl-imidazol-1-yl)-phenyl]-(8-pyridin-2-yl-5,6,7,8-tetrahydro-quinazolin-2-yl)-amine

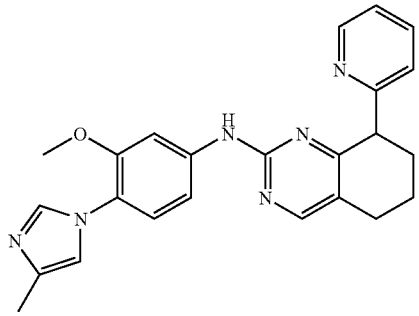

a) 2-[1-Dimethylamino-methylidene]-6-pyridin-2-yl-cyclohexanone

2-Pyridin-2-yl-cyclohexanone (175 mg, 1.0 mmol) was reacted with tert.-butoxy-bis-(dimethylamino)-methane using in analogous manner the procedure described in example 45a) to give crude title compound (226 mg) as a yellow solid which was used directly in the next step. MS ISP (m/e): 231.4 (100) [(M+H)$^+$].

b) (8-Ethoxy-5,6,7,8-tetrahydro-quinazolin-2-yl)-[3-methoxy-4-(4-methyl-imidazol-1-yl)-phenyl]-amine The title compound was prepared from ethyl 2-[1-dimethylamino-methylidene]-6-pyridin-2-yl-cyclohexanone (226 mg, 1.0 mmol) and N-[3-methoxy-4-(4-methyl-imidazol-1-yl)-phenyl]-guanidine dinitrate (137 mg, 0.37 mmol) using in analogous manner the procedure described in example 45b).

Obtained as a yellow solid (64 mg, 42%). MS ISP (m/e): 413.3 (100) [(M+H)$^+$]. mp 181-183° C.

Example 85

{2-[3-Methoxy-4-(4-methyl-imidazol-1-yl)-phenylamino]-5,6,7,8-tetrahydro-quinazolin-8-yl}-morpholin-4-yl-methanone

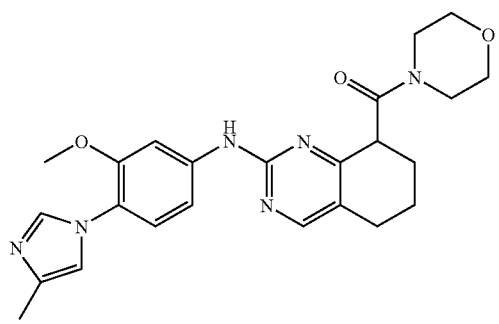

a) 1,4-Dioxa-spiro[4.5]decane-6-carbonyl chloride

To a solution of 1,4-dioxa-spiro[4.5]decane-6-carboxylic acid (2.42 g, 13 mmol) in methanol (6 mL) was added a 5.4 N solution of sodium methoxide in methanol (2.41 mL). The mixture was stirred at 20° C. for 20 min and the solvent was then evaporated under reduced pressure. Toluene (20 mL) was added to the residue and the solvent was evaporated under reduced pressure. The white solid obtained (2.5 g) was suspended in toluene (13 mL) and thionyl chloride (1 mL, 13.8 mmol) was added to the stirred solution at 20° C. over 10 min. Stirring was continued at 40° C. for 1 h when gas evolution stopped to give a ca 1 M solution of 1,4-dioxa-spiro[4.5]decane-6-carbonyl chloride in toluene.

b) (1,4-Dioxa-spiro[4.5]dec-6-yl)-morpholin-4-yl-methanone

Morpholine (0.22 mL, 2.5 mmol) was added at 0° C. to a 1 M solution of 1,4-dioxa-spiro[4.5]decane-6-carbonyl chloride in toluene (1 mL, 1 mmol). The mixture was stirred at 20° C. for 1 h, then diluted with ethyl acetate (40 mL), and washed successively with water (10 mL), saturated aqueous sodium carbonate solution (10 mL), 1 N hydrochloric acid, and with brine (10 mL). The organic layer was dried over sodium sulfate and evaporated under reduced pressure to give the title compound (59 mg, 23%) as white solid. MS ISP (m/e): 256.3 (100) [(M+H)$^+$].

c) 2-(Morpholine-4-carbonyl)-cyclohexanone

To a solution of (1,4-dioxa-spiro[4.5]dec-6-yl)-morpholin-4-yl-methanone (59 mg, 0.23 mmol) in 60% aqueous ethanol (1.1 mL) were added 2 drops of conc. sulfuric acid (20 uL) and the mixture was heated to 80° C. for 2 h. The mixture was cooled to 20° C., diluted with ethyl acetate (20 mL) and washed with saturated aqueous sodium carbonate solution (10 mL), and with brine (10 mL). The organic layer was dried over sodium sulfate and evaporated under reduced pressure to give the title compound (17 mg, 35%) as a white solid. MS ISP (m/e): 211.9 (100) [(M+H)$^+$].

d) 2-[1-Dimethylamino-methylidene]-6-(morpholine-4-carbonyl)-cyclohexanone 2-(Morpholine-4-carbonyl)-cyclohexanone (17 mg, 0.08 mmol) was reacted with tert.-butoxy-bis-(dimethylamino)-methane using in analogous manner the procedure described in example 45a) to give crude title compound (16 mg) as a yellow oil which was used directly in the next step. MS ISP (m/e): 267.5 (100) [(M+H)$^+$].

e) {2-[3-Methoxy-4-(4-methyl-imidazol-1-yl)-phenylamino]-5,6,7,8-tetrahydro-quinazolin-8-yl}-morpholin-4-yl-methanone The title compound was prepared from 2-[1-dimethylamino-methylidene]-6-(morpholine-4-carbonyl)-cyclohexanone (16 mg, 0.06 mmol) and N-[3-methoxy-4-(4-methyl-imidazol-1-yl)-phenyl]-guanidine dinitrate (17 mg, 0.045 mmol) using in analogous manner the procedure described in example 45b). Obtained as a yellow solid (5 mg, 25%). MS ISP (m/e): 449.4 (100) [(M+H)$^+$].

c) 2-[1-Dimethylamino-methylidene]-6-(morpholine-4-carbonyl)-cyclohexanone

2-Oxo-cyclohexanecarboxylic acid dimethylamide (31 mg, 0.18 mmol) was reacted with tert.-butoxy-bis-(dimethylamino)-methane using in analogous manner the procedure described in example 45a) to give crude title compound (25 mg) as a yellow solid which was used directly in the next step. MS ISP (m/e): 225.1 (100) [(M+H)$^+$].

d) 2-[3-Methoxy-4-(4-methyl-imidazol-1-yl)-phenylamino]-5,6,7,8-tetrahydro-quinazoline-8-carboxylic acid dimethylamide The title compound was prepared from 2-[1-dimethylamino-methylidene]-6-(morpholine-4-carbonyl)-cyclohexanone (25 mg, 0.11 mmol) and N-[3-methoxy-4-(4-methyl-imidazol-1-yl)-phenyl]-guanidine dinitrate (31 mg, 0.084 mmol) using in analogous manner the procedure described in example 45b). Obtained as a white solid (23 mg, 67%). MS ISP (m/e): 407.4 (100) [(M+H)$^+$]. mp 150-152° C.

Example 86

2-[3-Methoxy-4-(4-methyl-imidazol-1-yl)-phenylamino]-5,6,7,8-tetrahydro-quinazoline-8-carboxylic acid dimethylamide

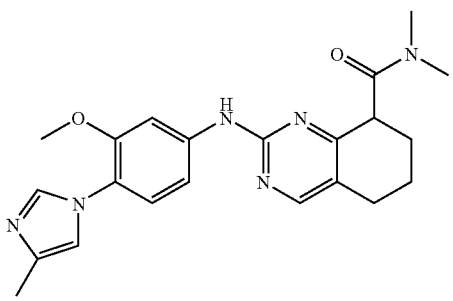

Example 87

{2-[3-Methoxy-4-(4-methyl-imidazol-1-yl)-phenylamino]-5,6,7,8-tetrahydro-quinazolin-8-yl}-pyrrolidin-1-yl-methanone

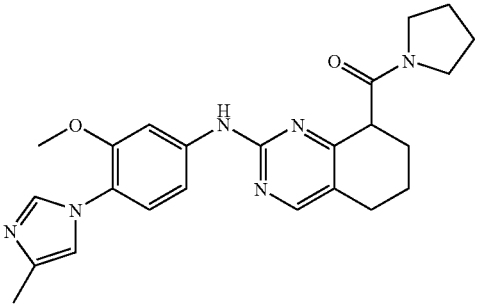

a) 1,4-Dioxa-spiro[4.5]decane-6-carboxylic acid dimethylamide

To a 1 M solution of 1,4-dioxa-spiro[4.5]decane-6-carbonyl chloride in toluene (1 mL, 1 mmol) was added at 0° C. a 7.9 M solution of dimethylamine in water (1.27 mL, 10 mmol). The mixture was stirred at 20° C. for 1 h, then diluted with ethyl acetate (40 mL), and washed successively with water (10 mL), saturated aqueous sodium carbonate solution (10 mL), 1 N hydrochloric acid, and with brine (10 mL). The organic layer was dried over sodium sulfate and evaporated under reduced pressure to give the title compound (69 mg, 32%) as colorless oil. MS ISP (m/e): 214.3 (100) [(M+H)$^+$].

b) 2-Oxo-cyclohexanecarboxylic acid dimethylamide

Using in analogous manner the procedure described in example 85c), 1,4-dioxa-spiro[4.5]decane-6-carboxylic acid dimethylamide (69 mg, 0.32 mmol) was hydrolyzed to give the title compound (31 mg, 57%) as a colorless oil. MS ISP (m/e): 170.3 (100) [(M+H)$^+$].

a) (1,4-Dioxa-spiro[4.5]dec-6-yl)-pyrrolidin-1-yl-methanone

Pyrrolidine (0.21 mL, 2.5 mmol) was added at 0° C. to a 1 M solution of 1,4-dioxa-spiro[4.5]decane-6-carbonyl chloride in toluene (1 mL, 1 mmol). The mixture was stirred at 20° C. for 1 h, then diluted with ethyl acetate (40 mL), and washed successively with water (10 mL), saturated aqueous sodium carbonate solution (10 mL), 1 N hydrochloric acid, and with brine (10 mL). The organic layer was dried over sodium sulfate and evaporated under reduced pressure to give the title compound (97 mg, 41%) as a white solid. MS ISP (m/e): 240.3 (100) [(M+H)$^+$].

b) 2-(Pyrrolidine-1-carbonyl)-cyclohexanone

Using in analogous manner the procedure described in example 85c), (1,4-dioxa-spiro[4.5]dec-6-yl)-pyrrolidin-1-yl-methanone (74 mg, 0.31 mmol) was hydrolyzed to give the title compound (56 mg, 93%) as a white solid. MS ISP (m/e): 196.3 (100) [(M+H)$^+$].

c) 2-[1-Dimethylamino-methylidene]-6-(pyrrolidine-1-carbonyl)-cyclohexanone 2-(Pyrrolidine-1-carbonyl)-cyclohexanone (56 mg, 0.29 mmol) was reacted with tert.-butoxy-bis-(dimethylamino)-methane using in analogous manner the procedure described in example 45a) to give crude title compound (58 mg) as a yellow oil which was used directly in the next step. MS ISP (m/e): 251.3 (100) [(M+H)$^+$].

d) {2-[3-Methoxy-4-(4-methyl-imidazol-1-yl)-phenylamino]-5,6,7,8-tetrahydro-quinazolin-8-yl}-pyrrolidin-1-yl-methanone The title compound was prepared from 2-[1-dimethylamino-methylidene]-6-(pyrrolidine-1-carbonyl)-cyclohexanone (58 mg, 0.23 mmol) and N-[3-methoxy-4-(4-methyl-imidazol-1-yl)-phenyl]-guanidine dinitrate (64 mg, 0.17 mmol) using in analogous manner the procedure described in example 45b). Obtained as a yellow solid (55 mg, 73%). MS ISP (m/e): 433.3 (100) [(M+H)$^+$]. mp 94-95° C.

Example 88

[3-Methoxy-4-(4-methyl-imidazol-1-yl)-phenyl]-[4-(3-methyl-[1,2,4]oxadiazol-5-yl)-4,5,6,7-tetrahydro-benzothiazol-2-yl]-amine

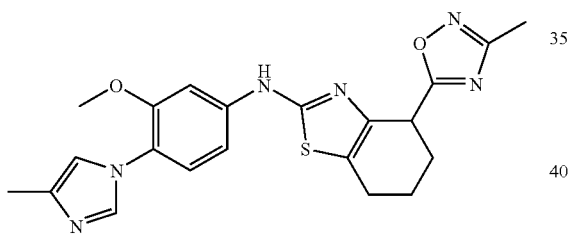

a) 2-Bromo-6-(3-methyl-[1,2,4]oxadiazol-5-yl)-cyclohexanone 2-(3-Methyl-[1,2,4]oxadiazol-5-yl)-cyclohexanone (90 mg, 0.5 mmol) was brominated using in analogous manner the procedure described in example 30a) to give crude title compound (173 mg) as a brown oil which was used directly in the next step.

b) 3-Methoxy-4-(4-methyl-imidazol-1-yl)-phenyl]-[4-(3-methyl-[1,2,4]oxadiazol-5-yl)-tetrahydro-benzothiazol-2-yl]-amine The title compound was prepared from [3-methoxy-4-(4-methyl-imidazol-1-yl)-phenyl]-thiourea (70 mg, 0.27 mmol) and crude 2-bromo-6-(3-methyl-[1,2,4]oxadiazol-5-yl)-cyclohexanone (173 mg, ca. 0.5 mmol) using in analogous manner the procedure described in example 1b). Obtained as a light-brown foam (25 mg, 22%). MS ISP (m/e): 423.1 (100) [(M+H)$^+$].

Example 89

[3-Methoxy-4-(3-methyl-[1,2,4]oxadiazol-5-yl)-phenyl]-(4-phenyl-4,5,6,7-tetrahydro-benzothiazol-2-yl)-amine

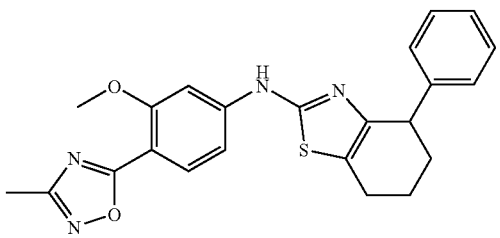

A solution of 4-(4-phenyl-4,5,6,7-tetrahydro-benzothiazol-2-yl)amino)-benzoic acid (120 mg, 0.32 mmol) and 1,1'-carbonyldiimidazol (60 mg, 0.36 mmol) in dimethylformamide (2 mL) was stirred for 50 minutes at 50° C. Acetamidoxmine (24 mg, 0.32 mmol) was added and the solution was stirred for 5 hours at 95° C. and then at 120° C. over night. The solution was diluted with ethyl acetate and washed four times with water, once with brine, dried over magnesium sulfate and the solvent was removed under reduced pressure. The residue was purified on silica gel using dichloromethane with 3% methanol as eluent to yield the title compound (19 mg, 14%) as a light beige solid. mp 228-231° C. MS ISP (m/e): 419.1 (100) [(M+H)$^+$].

Example 90

2-Methoxy-4-(4-phenyl-4,5,6,7-tetrahydro-benzothiazol-2-ylamino)-benzonitrile

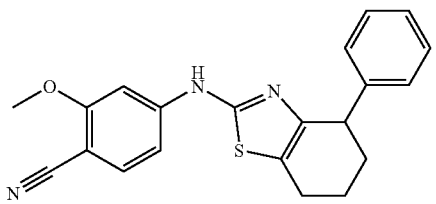

a) 2-Methoxy-4-(4-phenyl-4,5,6,7-tetrahydro-benzothiazol-2-ylamino)-benzamide

A solution of 4-(4-phenyl-4,5,6,7-tetrahydro-benzothiazol-2-ylamino)-benzoic acid (810 mg, 2.1 mmol) and 1,1'-carbonyldiimidazol (463 mg, 2.8 mmol) in dimethylformamide (15 mL) was stirred for 30 minutes at 50° C. The solution was cooled to 0° C. and 25% aqueous ammonium hydroxide solution (1.6 mL, 21.3 mmol) was added slowly. The reaction mixture was stirred for 45 minutes at room temperature. The reaction was poured onto water, stirred for 15 minutes and the solid was filtered off, washed with water and dried to yield the title compound (661 mg, 82%) as an off-white solid. mp 243-246° C. MS ISP (m/e): 380.4 (100) [(M+H)⁺].

b) 2-Methoxy-4-(4-phenyl-4,5,6,7-tetrahydro-benzothiazol-2-ylamino)-benzonitrile Trifluoroacetic acid anhydride (257 uL, 1.83 mmol) was added slowly to a cooled suspension of 2-methoxy-4-(4-phenyl-4,5,6,7-tetrahydro-benzothiazol-2-ylamino)-benzamide (625 mg, 1.65 mmol) in dioxane (2 mL) and pyridine (292 uL, 3.6 mmol). The white suspension was stirred for 30 minutes under cooling and then for 2 hours at 50° C. and for 3 hours at 80° C. Additional trifluoroacetic acid anhydride (300 uL), pyridine (400 uL) and dioxane (5 mL) were added and the reaction was stirred at 80° C. for 2 hours resulting in a clear brown solution. The solvent was removed under reduced pressure and the residue was partitioned between ethyl acetate and water. The organic layer was washed twice with saturated aqueous sodium hydrogen carbonate, brine, dried over magnesium sulfate, filtered and the solvent was removed under reduced pressure. The residue was purified on silica gel using dichloromethane with 4% methanol as eluent to yield the title compound (236 mg, 40%) as a beige foam. MS ISP (m/e): 362.3 (100) [(M+H)⁺].

Example 91

[3-Methoxy-4-(1-methyl-1H-pyrazol-4-yl)-phenyl]-(4-phenyl-4,5,6,7-tetrahydro-benzothiazol-2-yl)-amine

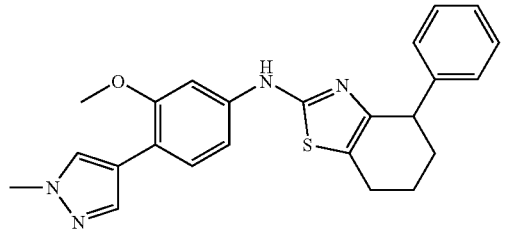

a) (4-Bromo-3-methoxy-phenyl)-(4-phenyl-4,5,6,7-tetrahydro-benzothiazol-2-yl)-amine (4-Bromo-3-methoxy-phenyl)-thiourea (1.20 g, 4.59 mmol) and 2-bromo-6-phenyl-cyclohexanone (1.29 g, 5.10 mmol) in 20 ml ethanol were stirred overnight at reflux. The brown solution was evaporated to dryness; the brown residue was dissolved in chloroform, washed three times with water and dried with magnesium sulfate. The solvent was evaporated in vacuo. Column chromatography (70 g silica, dichloromethane) afforded the title compound (1.18 g, 62%) as a light brown foam. MS ISP (m/e): 417.1 (100) [(M+H)⁺]. ¹H NMR (CDCl₃, 300 MHz): □ (ppm)=7.25 (m, 7H), 6.90 (s broad, 1H), 6.50 (dd, 1H), 4.04 (m broad, 1H), 3.58 (s, 3H), 2.75 (m broad, 2H), 2.20 (m broad, 1H), 1.77 (m broad, 3H).

b) [3-Methoxy-4-(1-methyl-1H-pyrazol-4-yl)-phenyl]-(4-phenyl-4,5,6,7-tetrahydro-benzothiazol-2-yl)-amine In a microwave vial a mixture of (4-bromo-3-methoxyphenyl)-(4-phenyl-4,5,6,7-tetrahydro-benzothiazol-2-yl)-amine (120 mg, 0.289 mmol), 1-methyl-4-(4,4,5,5-tetramethyl-1,3,2-dioxaborolan-2-yl)-1H-pyrazole (185 mg, 0.88 mmol), palladium (II) acetate (6 mg 0.027 mmol) and potassium fluoride (51 mg, 0.867 mmol) in 6 ml methanol was purged with nitrogen. The vial was sealed and the mixture was irradiated for ½ h at 140° C. in a microwave oven. The reaction mixture was filtered and the filtrate was concentrated, the residue was dissolved in dichloromethane, washed three times with water, dried and evaporated in vacuo. Column chromatography (12 g silica, dichloromethane+1.8% methanol v/v) afforded the title compound (19 mg, 16%) as a light brown wax. MS ISP (m/e): 417.1 (100) [(M+H)⁺]. ¹H NMR (CDCl₃, 300 MHz): δ (ppm)=7.79 (s, 1H), 7.75 (s, 1H), 7.38 (d, 1H), 7.22 (m, 6H), 6.97 (s, broad, 1H), 6.65 (dd, 1H), 4.05 (s broad, 1H), 3.92 (s, 3H), 3.68 (s, 3H), 2.75 (m broad, 2H), 2.20 (m broad, 1H), 1.88 (m broad, 3H).

Example 92

[3-Methoxy-4-(2-methyl-thiazol-5-yl)-phenyl]-(4-phenyl-4,5,6,7-tetrahydro-benzothiazol-2-yl)-amine

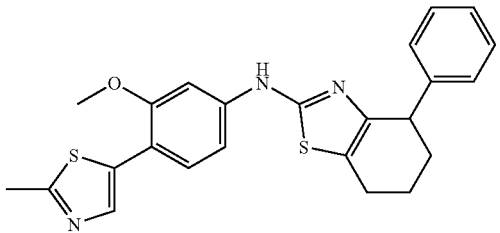

a) 5-(2-methoxy-4-nitro-phenyl)-2-methyl-thiazole

In a microwave vial a mixture of 2-bromo-5-nitroanisole (800 mg, 3.38 mmol), potassium acetate (503 mg, 5.07 mmol) and tetrakis(triphenylphosphine)-palladium(0) (197 mg, 0.17 mmol) in N,N-dimethylacetamide (12 mL) was flushed with argon while 2-methylthiazole (1.71 g, 16.9 mmol) was added. The tube was sealed and the mixture was irradiated 2 times for 30 minutes in a microwave oven at 160° C. The red-brown mixture was partitioned between ethyl acetate and water. The water layer was re-extracted with ethyl acetate. The combined organic phases were washed three times with water, once with brine, dried with magnesium sulfate and evaporated to dryness. Column chromatography (70 g silica, heptane/ethyl acetate 7:3 v/v) afforded the title compound (360 mg, 42%) as a yellow solid. MS ISP (m/e): 251.1 (100) [(M+H)⁺]. ¹H NMR (CDCl₃, 300 MHz): δ (ppm)=8.15 (s, 1H), 7.90 (dd, 1H), 7.84 (s, 1H), 7.72 (d, 1H), 4.05 (s, 3H), 2.76 (s, 3H). mp 114-117° C.

b) 3-Methoxy-4-(2-methyl-thiazol-5-yl)-phenylamine

A suspension of 5-(2-methoxy-4-nitro-phenyl)-2-methyl-thiazole (330 mg, 1.32 mmol) and anhydrous stannous chloride (1.28 g, 6.59 mmol) in ethanol (21 mL) was stirred at reflux for 1 hour. The yellow solution is evaporated and the residue dissolved in ethyl acetate. This solution is washed twice with 2N aqueous sodium hydroxide solution, with brine, dried with magnesium sulfate and evaporated to dryness to afford the title compound (266 mg, 91%) as an orange solid. MS ISP (m/e): 221.2 (100) [(M+H)]. ¹H NMR (CDCl₃, 300 MHz): δ(ppm)=7.81 (s, 1H), 7.33 (d, 1H), 6.31 (m, 2H), 3.87 (s, 3H), 3.83 (m, 2H), 2.69 (s, 3H). mp 125-129° C.

c) [3-Methoxy-4-(2-methyl-thiazol-5-yl)-phenyl]-thiourea

To a solution of 3-methoxy-4-(2-methyl-thiazol-5-yl)-phenylamine (100 mg, 0.45 mmol) in tetrahydrofurane (4 mL) was added drop wise under stirring and under an atmosphere benzoyl isothiocyanate (67.7 ul, 0.48 mmol). The reaction was stirred at room temperature for 3 hours and the solvent was removed under reduced pressure. The residue was dissolved in methanol (6 mL) and a solution of potassium carbonate (188 mg, 1.36 mmol) in water (3 mL) was added. The resulting suspension was stirred at room temperature over night. The precipitate was filtered off, washed with water and diethyl ether to yield the title compound as a pale yellow solid (113 mg, 89%). MS ISP (m/e): 280.1 (100%) [(M+H)+]. $^1$H NMR (DMSO-D$_6$, 300 MHz): δ (ppm)=9.82 (s, 1H, NH), 8.02 (s, 1H), 7.62 (d, 1H), 7.40 (s, 1H), 7.01 (s, 1H), 3.87 (s, 3H), 2.64 (s, 3H).

d) [3-Methoxy-4-(2-methyl-thiazol-5-yl)-phenyl]-(4-phenyl-4,5,6,7-tetrahydro-benzothiazol-2-yl)-amine A solution of [3-methoxy-4-(2-methyl-thiazol-5-yl)-phenyl]-thiourea (110 mg, 0.39 mmol) and 2-bromo-6-phenyl-cyclohexanone (105 mg, 0.41 mmol) in ethanol (4 ml) was heated to reflux over night. The precipitated solid was filtered off after cooling to room temperature and dried to yield the title compound (160 mg, 94%) as a yellow solid. MS ISP (m/e): 434.3 (100) [(M+H)+]. $^1$H NMR (DMSO-D$_6$, 300 MHz): δ (ppm)=10.32 (br s, 1H, NH), 8.10 (s, 1H), 7.61 (s, 1H), 7.56 (d, 1H), 7.29 (t, 2H), 7.15-7.21 (m, 3H), 6.85 (d, 1H), 4.00 (m, 1H), 3.48 (s, 3H), 2.75 (m, 2H), 2.68 (s, 3H), 2.14 (m, 1H), 1.70-1.94 (m, 3H).

Example 93

[4-(2,4-Dimethyl-thiazol-5-yl)-3-methoxy-phenyl]-(4-phenyl-4,5,6,7-tetrahydro-benzothiazol-2-yl)-amine

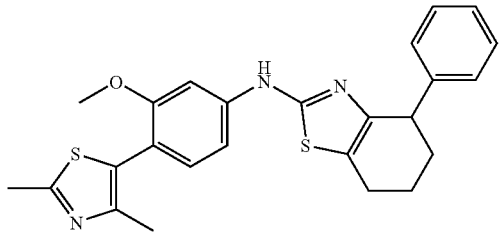

a) 5-(2-Methoxy-4-nitro-phenyl)-2,4-dimethyl-thiazole

In a microwave vial a mixture of 2-bromo-5-nitroanisole (600 mg, 2.53 mmol), potassium acetate (377 mg, 3.80 mmol) and tetrakis(triphenylphosphine)-palladium(0) (148 mg, 0.13 mmol) in N,N-dimethylacetamide (8 mL) was flushed with nitrogene while 2,4-dimethylthiazole (1.47 g, 12.7 mmol) was added. The tube was sealed and the mixture irradiated for 30 minutes at 170° C. The red-brown mixture was partitioned between ethyl acetate and water. The aqueous layer was re-extracted with ethyl acetate. The combined organic phases were washed with water, with brine, dried with magnesium sulfate and the solvent was evaporated to dryness. Column chromatography (40 g silica, heptane/ethyl acetate 7:3 v/v) afforded the title compound (415 mg, 62%) as a yellow solid. MS ISP (m/e): 265.1 (100) [(M+H)+]. $^1$H NMR (CDCl$_3$, 300 MHz): δ (ppm)=7.90 (dd, 1H), 7.81 (d, 1H), 7.45 (d, 1H), 3.95 (s, 3H), 2.71 (s, 3H), 2.35 (s, 3H). mp 123-125° C.

b) 4-(2,4-Dimethyl-thiazol-5-yl)-3-methoxy-phenylamine

A suspension of 5-(2-methoxy-4-nitro-phenyl)-2,4-dimethyl-thiazole (415 mg, 1.6 mmol) and anhydrous stannous chloride (1.52 g, 7.9 mmol) in ethanol (25 mL) was stirred at reflux for 3 hours. The yellow solution was evaporated and the residue dissolved in ethyl acetate. This solution was washed with 1N aqueous sodium hydroxide solution, twice with water, with brine, dried with magnesium sulfate and the solvent was evaporated to dryness. Column chromatography (50 g silica, heptane/ethyl acetate 30-60% v/v) afforded the title compound (276 mg, 75%) as a pale yellow solid. MS ISP (m/e): 235.2 (100) [(M+H)+]. $^1$H NMR (CDCl$_3$, 300 MHz): δ (ppm)=7.04 (d, 1H), 6.31 (m, 2H), 3.80 (s broad, 2H), 3.78 (s, 3H), 2.66 (s, 3H), 2.29 (s, 3H). mp 112-115° C.

c) [4-(2,4-Dimethyl-thiazol-5-yl)-3-methoxy-phenyl]-thiourea

To a solution of 4-(2,4-dimethyl-thiazol-5-yl)-3-methoxy-phenylamine (100 mg, 0.43 mmol) in tetrahydrofurane (4 mL) was added drop wise under stirring and under an atmosphere benzoyl isothiocyanate (63.6 ul, 0.45 mmol). The reaction was stirred at room temperature for 3 hours and the solvent was removed under reduced pressure. The residue was dissolved in methanol (6 mL) and a solution of potassium carbonate (177 mg, 1.28 mmol) in water (3 mL) was added. The resulting suspension was stirred at room temperature over night. The precipitate was filtered off, washed with water and diethyl ether to yield the title compound as a pale yellow solid (90 mg, 72%). MS ISP (m/e): 294.1 (100) [(M+H)+]. $^1$H NMR (DMSO-D$_6$, 300 MHz): δ (ppm)=9.81 (s, 1H, NH), 7.35 (s, 1H), 7.21 (d, 1H), 7.01 (s, 1H), 3.76 (s, 3H), 2.59 (s, 3H), 2.20 (s, 3H).

d) [4-(2,4-Dimethyl-thiazol-5-yl)-3-methoxy-phenyl]-(4-phenyl-4,5,6,7-tetrahydro-benzothiazol-2-yl)-amine A solution of [4-(2,4-dimethyl-thiazol-5-yl)-3-methoxy-phenyl]-thiourea (88 mg, 0.30 mmol) and 2-bromo-6-phenyl-cyclohexanone (80 mg, 0.32 mmol) in ethanol (3 ml) was heated to reflux over night. The precipitated solid was filtered off after cooling to room temperature and dried to yield the title compound (100 mg, 100%) as a yellow solid. MS ISP (m/e): 448.2 (100) [(M+H)+]. $^1$H NMR (DMSO-D$_6$, 300 MHz): δ (ppm)=10.27 (br s, 1H, NH), 7.59 (s, 1H), 7.28 (t, 2H), 7.12-7.19 (m, 4H), 6.85 (d, 1H), 4.00 (m, 1H), 3.37 (s, 3H), 2.74 (m, 2H), 2.66 (s, 3H), 2.20 (s, 2H), 2.13 (m, 1H), 1.70-1.93 (m, 3H).

Example 94

(4-Phenyl-4,5,6,7-tetrahydro-benzothiazol-2-yl)-(4-pyridin-4-yl-phenyl)-amine

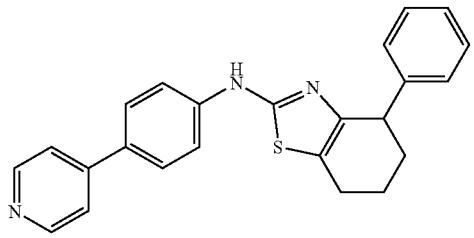

a) (4-Pyridin-4-yl-phenyl)-thiourea

To a solution of 4-pyridin-4-yl-phenylamine (142 mg, 0.83 mmol) in tetrahydrofurane (5 mL) was added drop wise under benzoyl isothiocyanate (124 uL, 0.88 mmol). The reaction was stirred at room temperature for 3 hours. The solvent was removed under reduced pressure. The residue was dissolved in methanol (6 mL) and a solution of potassium carbonate (346 mg, 2.5 mmol) in water (3 mL) was added. The resulting suspension was stirred at room temperature over night. The precipitate was filtered off, washed with water and diethyl ether to yield the title compound as a pale yellow solid (291 mg, 152%). MS ISP (m/e): 230.2 (56) [(M+H)$^+$], 213.0 (100) [(M-NH$_3$+H)$^+$]. $^1$H NMR (DMSO-D$_6$, 300 MHz): δ (ppm)=9.86 (s, 1H, NH), 8.61 (d, 2H), 7.79 (d, 2H), 7.69 (d, 1H), 7.61 (d, 2H).

b) (4-Phenyl-4,5,6,7-tetrahydro-benzothiazol-2-yl)-(4-pyridin-4-yl-phenyl)-amine A solution of (4-pyridin-4-yl-phenyl)-thiourea (100 mg, 0.44 mmol) and 2-bromo-6-phenyl-cyclohexanone (116 mg, 0.46 mmol) in ethanol (5 ml) was heated to reflux over night. The solvent was removed under reduced pressure and the residue was purified by column chromatography on silica gel using methylene chloride and methylene chloride/methanol (19:1 v/v) as the eluent to yield the title compound (34 mg, 20%) as a yellow solid. MS ISP (m/e): 384.2 (100) [(M+H)$^+$]. $^1$H NMR (DMSO-D$_6$, 300 MHz): δ (ppm)=8.61 (d, 2H), 7.59 (d, 2H), 7.46 (d, 1H), 7.18-7.33 (m, 5H), 7.13 (d, 2H), 4.08 (m, 1H), 2.75 (m, 2H), 2.18 (m, 1H), 1.7-1.98 (m, 3H).

Example 95

[4-(2-Ethyl-oxazol-5-yl)-phenyl]-(4-phenyl-4,5,6,7-tetrahydro-benzothiazol-2-yl)-amine

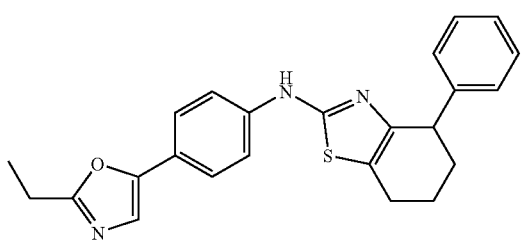

a) [4-(2-Ethyl-oxazol-5-yl)-phenyl]-thiourea

To a solution of 4-(2-ethyl-oxazol-5-yl)-phenylamine (470 mg, 2.5 mmol, CAS 73286-36-9) in tetrahydrofurane (20 mL) was added benzoyl isothiocyanate (449 mg, 2.8 mmol). The reaction was stirred at room temperature for 2 hours. The solvent was removed under reduced pressure and the residue was suspended in methanol (30 mL). Potassium carbonate (1036 mg, 7.5 mmol) dissolved in water (15 mL) was added drop wise to the suspension. The reaction was stirred at room temperature over night. The resulting solution was evaporated and the residue was stirred with water. The precipitate was filtered off, washed twice with water and twice with diethyl ether. The residue was dissolved in tetrahydrofurane and the solvent was removed under reduced pressure to yield the title compound as a light yellow solid (270 mg, 44%). MS ISP (m/e): 248.1 (100) [(M+H)$^+$]. $^1$H NMR (DMSO-D$_6$, 300 MHz): δ=9.80 (s, 1H, NH), 7.61 (d, 2H), 7.52 (d, 2H), 7.46 (s, 1H), 3.80 (q, 2H), 1.28 (t, 3H).

b) [4-(2-Ethyl-oxazol-5-yl)-phenyl]-(4-phenyl-4,5,6,7-tetrahydro-benzothiazol-2-yl)-amine A solution of [4-(2-ethyl-oxazol-5-yl)-phenyl]-thiourea (124 mg, 0.50 mmol) and 2-bromo-6-phenyl-cyclohexanone (139 mg, 0.55 mmol) in ethanol (5 ml) was heated to reflux over night. The solvent was evaporated under reduced pressure and the residue was purified by column chromatography on silica gel using methylene chloride and methylene chloride/methanol (19:1 v/v) as eluent to yield the title compound (170 mg, 85%) as a brown solid. MS ISP (m/e): 402.3 (100) [(M+H)$^+$]. $^1$H NMR (DMSO-D$_6$, 300 MHz): δ (ppm)=10.18 (br s, 1H, NH), 7.49 (s, 4H), 7.26-7.30 (m, 3H), 7.19 (t, 1H), 7.12 (d, 1H), 4.05 (m, 1H), 2.77 (q, 2H), 2.75 (m, 2H), 2.12 (m, 1H), 1.70-1.88 (m, 3H), 1.25 (t, 3H).

Example 96

[4-(2,4-Dimethyl-oxazol-5-yl)-phenyl]-(4-phenyl-4,5,6,7-tetrahydro-benzothiazol-2-yl)-amine

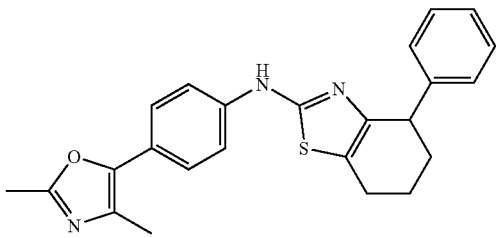

a) [4-(2,4-dimethyl-oxazol-5-yl)-phenyl]-thiourea

To a solution of 4-(2,4-dimethyl-oxazol-5-yl)-phenylamine (470 mg, 2.5 mmol, CAS 100060-02-41) in tetrahydrofurane (20 mL) was added benzoyl isothiocyanate (449 mg, 2.8 mmol). The reaction was stirred at room temperature for 2 hours. The solvent was removed under reduced pressure and the residue was suspended in methanol (30 mL). Potassium carbonate (1036 mg, 7.5 mmol) dissolved in water (15 mL) was added drop wise to the suspension. The reaction was stirred at room temperature over night. The resulting solution was evaporated and the residue was stirred with water. The precipitate was filtered off, washed twice with water and twice with diethyl ether. The residue was dissolved in tetrahydrofurane and the solvent was removed under reduced pressure to yield the title compound as an off-white solid (420 mg, 68%). MS ISP (m/e): 248.1 (100) [(M+H)$^+$]. $^1$H NMR (DMSO-D$_6$, 300 MHz): δ (ppm)=9.80 (s, 1H, NH), 7.55 (d, 2H), 7.50 (d, 2H), 2.41 (s, 3H), 2.29 (s, 3H).

b) [4-(2,4-Dimethyl-oxazol-5-yl)-phenyl]-(4-phenyl-4,5,6,7-tetrahydro-benzothiazol-2-yl)-amine A solution of [4-(2,4-dimethyl-oxazol-5-yl)-phenyl]-thiourea (124 mg, 0.50 mmol) and 2-bromo-6-phenyl-cyclohexanone (139 mg, 0.55 mmol) in ethanol (5 ml) was heated to reflux over night. The precipitated solid was filtered off after cooling to room temperature and dried to yield the title compound (170 mg, 85%) as a light brown solid. MS ISP (m/e): 402.2 (100) [(M+H)$^+$]. $^1$H NMR (DMSO-D$_6$, 300 MHz): δ (ppm)=10.37 (br s, 1H, NH), 7.53 (d, 2H), 7.42 (d, 2H), 7.30 (t, 2H), 7.20 (t, 1H), 7.12 (d, 1H), 4.05 (m, 1H), 2.72 (m, 2H), 2.39 (s, 3H), 2.24 (s, 3H), 2.12 (m, 1H), 1.70-1.88 (m, 3H).

Example 97

[4-(3-Methyl-[1,2,4]thiadiazol-5-yl)-phenyl]-(4-phenyl-4,5,6,7-tetrahydro-benzothiazol-2-yl)-amine

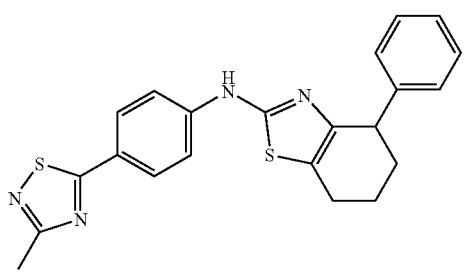

a) 4-(3-Methyl-[1,2,4]thiadiazol-5-yl)-phenylamine

To a suspension of 3-methyl-5-(4-nitro-phenyl)-[1,2,4]thiadiazole (104 mg, 0.423 mmol, CAS 800408-77-9) in ethanol (4.3 mL) was added tin(II) chloride (401 mg, 2.1 mmol) and the reaction was heated to 70° C. for 4 hours. The yellow solution was poured onto saturated aqueous sodium hydrogen carbonate solution and the mixture was stirred for 30 minutes. The precipitate was filtered off, washed with water. The solid was heated 3 times with tetrahydrofurane and filtered. The collected organic layers were evaporated to yield crude title compound (110 mg, quant.) as a yellow solid. MS ISP (m/e): 192.2 (100) [(M+H)$^+$]. $^1$H NMR (DMSO-D$_6$, 300 MHz): δ (ppm)=7.64 (d, 2H), 6.63 (d, 2H), 6.01 (br s, 2H), 2.54 (s, 3H).

b) [4-(3-Methyl-[1,2,4]thiadiazol-5-yl)-phenyl]-thiourea

To a solution of 4-(3-methyl-[1,2,4]thiadiazol-5-yl)-phenylamine (81 mg, 0.42 mmol) in tetrahydrofurane (6.4 mL) was added benzoyl isothiocyanate (76 mg, 0.44 mmol). The reaction was stirred at room temperature for 3 hours. The solvent was removed under reduced pressure and the residue was suspended in methanol (10.6 mL). Potassium carbonate (175 mg, 1.27 mmol) dissolved in water (5.3 mL) was added drop wise to the suspension. The reaction was stirred at room temperature over night. The resulting solution was evaporated and the residue was stirred with water. The precipitate was filtered off, washed with water and with diethyl ether to yield the title compound as a yellow solid (75 mg, 71%). MS ISP (m/e): 251.0 (100) [(M+H)$^+$], 501.1 (83) [(2M+H)$^+$]. $^1$H NMR (DMSO-D$_6$, 300 MHz): δ (ppm)=10.04 (br s, 1H), 7.94 (d, 2H), 7.72 (d, 2H), 2.63 (s, 3H).

c) [4-(3-Methyl-[1,2,4]thiadiazol-5-yl)-phenyl]-(4-phenyl-4,5,6,7-tetrahydro-benzothiazol-2-yl)-amine A solution of [4-(3-methyl-[1,2,4]thiadiazol-5-yl)-phenyl]-thiourea (75 mg, 0.3 mmol) and 2-bromo-6-phenyl-cyclohexanone (84 mg, 0.33 mmol) in ethanol (3 ml) was heated to reflux over night. The precipitated solid, unreacted thiourea, was filtered off after cooling to room temperature and washed with ethanol. The filtrate was evaporated under reduced pressure and the residue was purified on silica gel using heptane/ethyl acetate (4:1 v/v) as the eluent to yield the title compound (12 mg, 10%) as a yellow solid. MS ISP (m/e): 405.2 (100) [(M+H)$^+$]. $^1$H NMR (DMSO-D$_6$, 300 MHz): δ (ppm)=10.51 (br s, 1H, NH), 7.82 (d, 2H), 7.58 (d, 2H), 7.28 (t, 2H), 7.19 (t, 1H), 7.13 (d, 1H), 4.07 (m, 1H), 2.72 (m, 2H), 2.58 (s, 3H), 2.13 (m, 1H), 1.70-1.90 (m, 3H).

The invention claimed is:

1. A compound of formula I

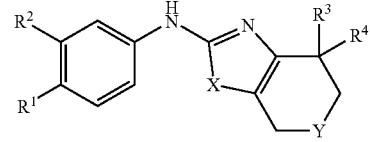

I wherein
R$^1$ is —C(O)O-lower alkyl or cyano or is selected from the group consisting of pyridine-4-yl, thiazole-5-yl, oxazol-5-yl, [1,2,4]triazol-1-yl, imidazol-1-yl, pyrazol-4-yl, [1,2,4]oxadiazol-5-yl, [1,3,4]-oxadiazol-2-yl, and [1,2,4]-thiadiazol-5-yl,
optionally substituted by R';
R' is halogen, lower alkyl, lower alkyl substituted by halogen, lower alkoxy or lower alkoxy substituted by halogen;
R$^2$ is hydrogen, lower alkoxy, lower alkyl, halogen or cyano;
R$^3$ is —(CH$_2$)$_n$—C(O)O-lower alkyl, lower alkoxy, hydroxy, —O—Si(CH$_3$)$_2$-lower alkyl, —C(O)—N(lower alkyl)$_2$, —O—S(O)$_2$-lower alkyl, C$_{3-7}$-cycloalkyl, S(O)$_2$-aryl, or is heterocyclyl or —C(O)-heterocyclyl, wherein the heterocyclyl group is pyrrolidinyl, piperidinyl, or morpholinyl, or is aryl or hetaryl, wherein aryl is phenyl, hetaryl is pyridyl or [1,2,4]oxadiazole-5-yl and wherein the aryl and hetaryl rings are optionally substituted by one or more R';
R$^4$ is hydrogen, lower alkyl, hydroxy or CH$_2$CN;
X is S or —N═C(R$^5$)—;
R$^5$ is hydrogen, lower alkyl or hydroxy,
Y is a bond, —O—, —CH$_2$—, —CH$_2$—CH$_2$—,

or —N(R)—;
R is hydrogen, lower alkyl, C(O)O-lower alkyl, C(O)-lower alkyl, S(O)$_2$-lower alkyl, or benzyl; and
n is 0 or 1;
or a pharmaceutically active acid addition salt thereof.

2. The compound of claim 1 having formula I-A

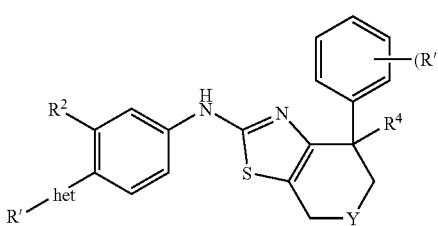

I-A wherein
het is selected from the group consisting of pyridine-4-yl, thiazole-5-yl, oxazol-5-yl, [1,2,4]triazol-1-yl, imidazol-1-yl, pyrazol-4-yl, [1,2,4]oxadiazol-5-yl, [1,3,4]-oxadiazol-2-yl, and [1,2,4]-thiadiazol-5-yl, R' is hydrogen, halogen, lower alkyl, lower alkyl substituted by halogen, lower alkoxy or lower alkoxy substituted by halogen;

$R^2$ is hydrogen, lower alkoxy, hydroxy, lower alkyl, halogen or cyano;

$R^4$ is hydrogen, lower alkyl, hydroxy or $CH_2CN$;

Y is a bond, —O—, —$CH_2$—, —$CH_2$—$CH_2$—,

or —N(R)—;

R is hydrogen, lower alkyl, C(O)O-lower alkyl, C(O)-lower alkyl, S(O)$_2$-lower alkyl, or benzyl; and m is 0, 1, or 2;

or a pharmaceutically active acid addition salt thereof.

3. The compound of claim 2, wherein Y is —$CH_2$—.

4. The compound of claim 3, selected from the group consisting of
(3-methoxy-4-oxazol-5-yl-phenyl)-(4-phenyl-4,5,6,7-tetrahydro-benzothiazol-2-yl)-amine;
[3-fluoro-4-(4-methyl-imidazol-1-yl)-phenyl]-(4-phenyl-4,5,6,7-tetrahydro-benzothiazol-2-yl)-amine;
[3-methoxy-4-(4-methyl-imidazol-1-yl)-phenyl]-(4-phenyl-4,5,6,7-tetrahydro-benzothiazol-2-yl)-amine;
[3-methoxy-4-(4-methyl-imidazol-1-yl)-phenyl]-[4-(2-methoxy-phenyl)-4,5,6,7-tetrahydro-benzothiazol-2-yl]-amine;
[3-methoxy-4-(4-methyl-imidazol-1-yl)-phenyl]-[4-(4-methyl-3-trifluoromethyl-phenyl)-4,5,6,7-tetrahydro-benzothiazol-2-yl]-amine;
[3-methoxy-4-(4-methyl-imidazol-1-yl)-phenyl]-[4-(4-trifluoromethoxy-phenyl)-4,5,6,7-tetrahydro-benzothiazol-2-yl]-amine;
[4-(2,5-difluoro-phenyl)-4,5,6,7-tetrahydro-benzothiazol-2-yl]-[3-methoxy-4-(4-methyl-imidazol-1-yl)-phenyl]-amine;
[4-(2,5-dimethyl-phenyl)-4,5,6,7-tetrahydro-benzothiazol-2-yl]-[3-methoxy-4-(4-methyl-imidazol-1-yl)-phenyl]-amine;
[4-(2-chloro-phenyl)-4,5,6,7-tetrahydro-benzothiazol-2-yl]-[3-methoxy-4-(4-methyl-imidazol-1-yl)-phenyl]-amine;
[4-(3-fluoro-4-methyl-phenyl)-4,5,6,7-tetrahydro-benzothiazol-2-yl]-[3-methoxy-4-(4-methyl-imidazol-1-yl)-phenyl]-amine; and
[4-(4-chloro-3-trifluoromethyl-phenyl)-4,5,6,7-tetrahydro-benzothiazol-2-yl]-[3-methoxy-4-(4-methyl-imidazol-1-yl)-phenyl]-amine.

5. The compound of claim 3, selected from the group consisting of
[4-(4-methyl-imidazol-1-yl)-phenyl]-(4-phenyl-4,5,6,7-tetrahydro-benzothiazol-2-yl)-amine;
{4-(4-chloro-phenyl)-2-[3-methoxy-4-(4-methyl-imidazol-1-yl)-phenylamino]-4,5,6,7-tetrahydro-benzothiazol-4-yl}-acetonitrile;
2-(4-methyl-imidazol-1-yl)-5-(4-phenyl-4,5,6,7-tetrahydro-benzothiazol-2-ylamino)-benzonitrile;
[4-(2,4-dichloro-phenyl)-4,5,6,7-tetrahydro-benzothiazol-2-yl]-[3-methoxy-4-(4-methyl-imidazol-1-yl)-phenyl]-amine;
[4-(2,5-dichloro-phenyl)-4,5,6,7-tetrahydro-benzothiazol-2-yl]-[3-methoxy-4-(4-methyl-imidazol-1-yl)-phenyl]-amine;
[4-(3,5-dichloro-phenyl)-4,5,6,7-tetrahydro-benzothiazol-2-yl]-[3-methoxy-4-(4-methyl-imidazol-1-yl)-phenyl]-amine;
[4-(3,5-difluoro-phenyl)-4,5,6,7-tetrahydro-benzothiazol-2-yl]-[3-methoxy-4-(4-methyl-imidazol-1-yl)-phenyl]-amine;
[4-(3,5-trifluoromethyl-phenyl)-4,5,6,7-tetrahydro-benzothiazol-2-yl]-[3-methoxy-4-(4-methyl-imidazol-1-yl)-phenyl]-amine;
[3-methoxy-4-(4-methyl-imidazol-1-yl)-phenyl]-(4-methyl-4-phenyl-4,5,6,7-tetrahydro-benzothiazol-2-yl)-amine;
[3-fluoro-4-(4-methyl-imidazol-1-yl)-phenyl]-[4-(4-methyl-3-trifluoromethyl-phenyl)-4,5,6,7-tetrahydro-benzothiazol-2-yl]-amine; and
[4-(2-chloro-phenyl)-4,5,6,7-tetrahydro-benzothiazol-2-yl]-[3-fluoro-4-(4-methyl-imidazol-1-yl)-phenyl]-amine.

6. A compound selected from the group consisting of
[3-fluoro-4-(4-methyl-imidazol-1-yl)-phenyl]-[4-(2-methoxy-phenyl)-4,5,6,7-tetrahydro-benzothiazol-2-yl]-amine;
[4-(2,4-dichloro-phenyl)-4,5,6,7-tetrahydro-benzothiazol-2-yl]-[3-fluoro-4-(4-methyl-imidazol-1-yl)-phenyl]-amine;
2-(4-methyl-imidazol-1-yl)-5-(4-phenyl-4,5,6,7-tetrahydro-benzothiazol-2-ylamino)-phenol;
[4-(2-methyl-oxazol-5-yl)-phenyl]-(4-phenyl-4,5,6,7-tetrahydro-benzothiazol-2-yl)-amine;
[3-methoxy-4-(1-methyl-1H-pyrazol-4-yl)-phenyl]-(4-phenyl-4,5,6,7-tetrahydro-benzothiazol-2-yl)-amine;
[3-methoxy-4-(2-methyl-thiazol-5-yl)-phenyl]-(4-phenyl-4,5,6,7-tetrahydro-benzothiazol-2-yl)-amine;
[4-(2,4-dimethyl-thiazol-5-yl)-3-methoxy-phenyl]-(4-phenyl-4,5,6,7-tetrahydro-benzothiazol-2-yl)-amine;
(4-phenyl-4,5,6,7-tetrahydro-benzothiazol-2-yl)-(4-pyridin-4-yl-phenyl)-amine;
[4-(2-ethyl-oxazol-5-yl)-phenyl]-(4-phenyl-4,5,6,7-tetrahydro-benzothiazol-2-yl)-amine;
[4-(2,4-dimethyl-oxazol-5-yl)-phenyl]-(4-phenyl-4,5,6,7-tetrahydro-benzothiazol-2-yl)-amine; and
[4-(3-methyl-[1,2,4]thiadiazol-5-yl)-phenyl]-(4-phenyl-4,5,6,7-tetrahydro-benzothiazol-2-yl)-amine.

7. The compound of claim 2, wherein Y is —N(R)—.

8. The compound of claim 7, selected from the group consisting of

[5-benzyl-7-(2-chloro-phenyl)-4,5,6,7-tetrahydro-thiazolo[5,4-c]pyridin-2-yl]-[3-methoxy-4-(4-methyl-imidazol-1-yl)-phenyl]-amine and

[5-benzyl-7-(4-chloro-3-fluorophenyl)-4,5,6,7-tetrahydro-thiazolo[5,4-c]pyridin-2-yl]-[3-methoxy-4-(4-methyl-imidazol-1-yl)-phenyl]-amine.

9. The compound of claim 1 having formula I-B

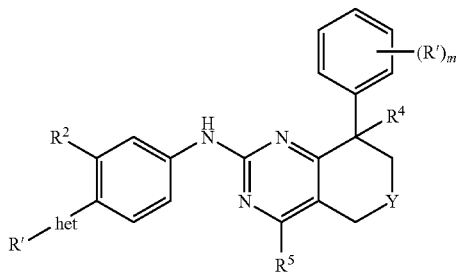

I-B wherein
het is imidazol-1-yl;
R' is hydrogen, halogen, lower alkyl, lower alkyl substituted by halogen, lower alkoxy or lower alkoxy substituted by halogen;
$R^2$ is hydrogen, lower alkoxy, hydroxy, lower alkyl, halogen or cyano;
$R^4$ is hydrogen, lower alkyl, hydroxy or $CH_2CN$;
$R^5$ is hydrogen, lower alkyl or hydroxy,
Y is a bond, —O—, —$CH_2$—, —$CH_2$—$CH_2$—,

or —N(R)—;
R is hydrogen, lower alkyl, C(O)O-lower alkyl, C(O)-lower alkyl, S(O)$_2$-lower alkyl, or benzyl; and
m is 0, 1, or 2;
or a pharmaceutically active acid addition salt thereof.

10. The compound of claim 9, wherein Y is —$CH_2$—.

11. The compound of claim 10, selected from the group consisting of
[3-fluoro-4-(4-methyl-imidazol-1-yl)-phenyl]-(8-phenyl-5,6,7,8-tetrahydro-quinazolin-2-yl)-amine;
[3-methoxy-4-(4-methyl-imidazol-1-yl)-phenyl]-(8-phenyl-5,6,7,8-tetrahydro-quinazolin-2-yl)-amine;
[8-(4-chloro-phenyl)-5,6,7,8-tetrahydro-quinazolin-2-yl]-[3-methoxy-4-(4-methyl-imidazol-1-yl)-phenyl]-amine;
[3-fluoro-4-(4-methyl-imidazol-1-yl)-phenyl]-[8-(4-fluoro-phenyl)-5,6,7,8-tetrahydro-quinazolin-2-yl]-amine;
2-[3-methoxy-4-(4-methyl-imidazol-1-yl)-phenylamino]-8-pyridin-3-yl-5,6,7,8-tetrahydro-quinazolin-8-ol;
[3-methoxy-4-(4-methyl-imidazol-1-yl)-phenyl]-(8-pyridin-2-yl-5,6,7,8-tetrahydro-quinazolin-2-yl)-amine; and
[3-methoxy-4-(4-methyl-imidazol-1-yl)-phenyl]-[8-(3,4,5-trifluoro-phenyl)-5,6,7,8-tetrahydro-quinazolin-2-yl]-amine.

12. The compound of claim 9, wherein Y is —N(R)—.

13. The compound of claim 12, selected from the group consisting of
2-[3-methoxy-4-(4-methyl-imidazol-1-yl)-phenylamino]-8-phenyl-7,8-dihydro-5H-pyrido[4,3-d]pyrimidine-6-carboxylic acid tert.-butyl ester;
[3-methoxy-4-(4-methyl-imidazol-1-yl)-phenyl]-(8-phenyl-5,6,7,8-tetrahydro-pyrido[4,3-d]pyrimidin-2-yl)-amine hydrochloride;
1-{2-[3-methoxy-4-(4-methyl-imidazol-1-yl)-phenylamino]-8-phenyl-7,8-dihydro-5H-pyrido[4,3-d]pyrimidin-6-yl}-ethanone;
(6-ethyl-(8-phenyl)-5,6,7,8-tetrahydro-pyrido[4,3-d]pyrimidin-2-yl)-[3-methoxy-4-(4-methyl-imidazol-1-yl)-phenyl]-amine; and
(6-isopropyl-(8-phenyl)-5,6,7,8-tetrahydro-pyrido[4,3-d]pyrimidin-2-yl)-[3-methoxy-4-(4-methyl-imidazol-1-yl)-phenyl]-amine.

14. A pharmaceutical composition comprising a therapeutically effective amount of a compound of formula I

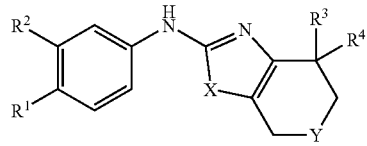

I wherein
$R^1$ is —C(O)O-lower alkyl or cyano or is selected from the group consisting of pyridine-4-yl, thiazole-5-yl, oxazol-5-yl, [1,2,4]triazol-1-yl, imidazol-1-yl, pyrazol-4-yl, [1,2,4]oxadiazol-5-yl, [1,3,4]-oxadiazol-2-yl, and [1,2,4]-thiadiazol-5-yl, optionally substituted by R';
R' is halogen, lower alkyl, lower alkyl substituted by halogen, lower alkoxy or lower alkoxy substituted by halogen;
$R^2$ is hydrogen, lower alkoxy, lower alkyl, halogen or cyano;
$R^3$ is —$(CH_2)_n$—C(O)O-lower alkyl, lower alkyl, lower alkoxy, hydroxy, —O—Si(CH$_3$)$_2$-lower alkyl, —C(O)—N(lower alkyl)$_2$, —O—S(O)$_2$-lower alkyl, $C_{3-7}$-cycloalkyl, S(O)$_2$-aryl, or is heterocyclyl or —C(O)-heterocyclyl, wherein the heterocyclyl group is pyrrolidinyl, piperidinyl, or morpholinyl, or is aryl or hetaryl, wherein aryl is phenyl, hetaryl is pyridyl or [1,2,4]oxadiazole-5-yl and wherein the aryl and hetaryl rings are optionally substituted by one or more R';
$R^4$ is hydrogen, lower alkyl, hydroxy or $CH_2CN$;
X is S or —N=C($R^5$)—;
$R^5$ is hydrogen, lower alkyl or hydroxy,
Y is a bond, —O—, —$CH_2$—, —$CH_2$—$CH_2$—,

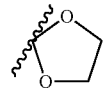

or —N(R)—;
R is hydrogen, lower alkyl, C(O)O-lower alkyl, C(O)-lower alkyl, S(O)$_2$-lower alkyl, or benzyl; and
n is 0 or 1;
or a pharmaceutically active acid addition salt thereof and a pharmaceutically acceptable carrier.

* * * * *